(12) United States Patent
Madge et al.

(10) Patent No.: US 7,371,729 B2
(45) Date of Patent: *May 13, 2008

(54) BORONIC ACID SALTS USEFUL IN PARENTERAL FORMULATIONS

(75) Inventors: David Jonathan Madge, London (GB); Mark Dolman, London (GB); Sophie Marie Combe-Marzelle, London (GB); John Joseph Deadman, Melbourne (AU); Anthony James Kennedy, London (GB); Sanjay Kumar Kakkar, London (GB)

(73) Assignee: Trigen Limited, London (GB)

( * ) Notice: Subject to any disclaimer, the term of this patent is extended or adjusted under 35 U.S.C. 154(b) by 235 days.

This patent is subject to a terminal disclaimer.

(21) Appl. No.: 10/658,971

(22) Filed: Sep. 9, 2003

(65) Prior Publication Data

US 2004/0138175 A1    Jul. 15, 2004

(30) Foreign Application Priority Data

| Sep. 9, 2002 | (GB) | .................................. | 0220764.5 |
| Sep. 9, 2002 | (GB) | .................................. | 0220822.1 |
| Apr. 4, 2003 | (GB) | .................................. | 0307817.7 |
| May 16, 2003 | (GB) | .................................. | 0311237.2 |
| Jul. 4, 2003 | (GB) | .................................. | 0315691.6 |

(51) Int. Cl.
   *A61K 38/04* (2006.01)
   *A61K 31/69* (2006.01)
(52) U.S. Cl. ......................................... 514/19; 514/64
(58) Field of Classification Search ................ 514/310, 514/391, 18, 2, 19, 64
   See application file for complete search history.

(56) References Cited

U.S. PATENT DOCUMENTS

| 2,934,556 | A | 4/1960 | Hoffmann et al. |
| 4,499,082 | A | 2/1985 | Shenvi et al. |
| 4,701,545 | A | 10/1987 | Matteson et al. |
| 4,935,493 | A | 6/1990 | Bachovchin et al. |
| 4,963,655 | A | 10/1990 | Kinder et al. |
| 5,169,841 | A | 12/1992 | Kleeman et al. |
| 5,187,157 | A | 2/1993 | Kettner et al. |
| 5,444,049 | A | 8/1995 | de Nanteuil et al. |
| 5,462,964 | A | 10/1995 | Fevig et al. |
| 5,563,127 | A | 10/1996 | Amparo et al. |
| 5,574,014 | A | 11/1996 | Claeson et al. |
| 5,585,360 | A | 12/1996 | de Nanteuil et al. |
| 5,596,123 | A | 1/1997 | Elgendy et al. |
| 5,639,739 | A | 6/1997 | Dominguez et al. |
| 5,658,885 | A | 8/1997 | Lee et al. |
| 5,681,978 | A | 10/1997 | Matteson et al. |
| 5,731,439 | A | 3/1998 | Carini et al. |
| 5,780,454 | A | 7/1998 | Adams et al. |
| 5,814,622 | A | 9/1998 | de Nanteuil et al. |
| 6,066,730 | A | 5/2000 | Adams et al. |
| 6,083,903 | A | 7/2000 | Adams et al. |
| 6,114,308 | A | 9/2000 | Claeson et al. |
| 6,297,217 | B1 | 10/2001 | Adams et al. |
| 6,313,096 | B1 | 11/2001 | Claeson et al. |
| 6,417,174 | B1 | 7/2002 | Shoichet et al. |
| 6,617,317 | B1 | 9/2003 | Adams et al. |
| 6,699,835 | B2 | 3/2004 | Plamondon et al. |
| 6,713,446 | B2 | 3/2004 | Gupta et al. |
| 6,747,150 | B2 | 6/2004 | Adams et al. |
| 7,112,590 | B2 | 9/2006 | Kikelj et al. |
| 2004/0147453 | A1 | 7/2004 | Deadman et al. |
| 2005/0119226 | A1 | 6/2005 | Walter et al. |
| 2005/0176651 | A1 | 8/2005 | Madge et al. |
| 2005/0282757 | A1 | 12/2005 | Combe-Marzelle et al. |
| 2005/0288253 | A1 | 12/2005 | Madge et al. |
| 2006/0084592 | A1 | 4/2006 | Boucher |
| 2006/0172920 | A1 | 8/2006 | Scully et al. |
| 2006/0172978 | A1 | 8/2006 | Russell et al. |
| 2006/0229257 | A1 | 10/2006 | Deadman et al. |

FOREIGN PATENT DOCUMENTS

| EP | 0 235 692 | 2/1987 |
| EP | 0471651 | 2/1992 |
| EP | 0 599 633 | 11/1993 |
| WO | WO 89/09612 | 10/1989 |
| WO | WO 92/07869 | 5/1992 |
| WO | WO 94/21650 | 9/1994 |
| WO | WO 94/21668 | 9/1994 |
| WO | WO 94/25049 | 11/1994 |
| WO | WO 95/09634 | 4/1995 |
| WO | WO 95/09858 | 4/1995 |
| WO | WO 95/09859 | 4/1995 |
| WO | WO 96/12499 | 5/1996 |
| WO | WO 96/13266 | 5/1996 |

(Continued)

OTHER PUBLICATIONS

"Cardiovasuclar Disease: Treatment for Stroke", Standford Hospital & Clinics, 2003.*

(Continued)

*Primary Examiner*—Brian Kwon
(74) *Attorney, Agent, or Firm*—Sterne, Kessler, Goldstein & Fox P.L.L.C.

(57) ABSTRACT

Salts of a peptide boronic acid drug, for example of Cbz-(R)-Phe-(S)-Pro-(R)-Mpg-B(OH)$_2$. The counter-ion to the boronate may be an alkali metal or derived from a strongly basic organic nitrogen-containing compound.

48 Claims, 2 Drawing Sheets

FOREIGN PATENT DOCUMENTS

| WO | WO 96/20689 | 7/1996 |
|---|---|---|
| WO | WO 97/05161 | 2/1997 |
| WO | WO 98/00443 | 1/1998 |
| WO | WO 98/31688 | 7/1998 |
| WO | WO 99/26652 | 6/1999 |
| WO | WO 00/35904 | 6/2000 |
| WO | WO 00/35905 | 6/2000 |
| WO | WO 00/41715 | 7/2000 |
| WO | WO 01/02424 | 1/2001 |
| WO | WO 01/41796 | 6/2001 |
| WO | WO 02/36157 | 5/2002 |
| WO | WO 02/059130 | 8/2002 |
| WO | WO 02/059131 | 8/2002 |
| WO | WO 03/007984 | 1/2003 |
| WO | WO 2005/084685 A2 | 9/2005 |
| WO | WO 2005/084686 A2 | 9/2005 |

OTHER PUBLICATIONS

"Heart Diseases", Charlotte E. Grayson, WebMD, 2004.*
"Acute Congestive Heart Failure", Thosmas N. Levin, Postgraduate Medicine, vol. 101, No. 1, 1997.*
"Chronic Renal Failure", University of Pennsylvania Health System, 2005.*
Bastin et al., "Salt Selection and Optimisation Procedures for Pharmaceutical New Chemical Entities," *Organic Process Research & Development* 4:427-235, 2000.
Brikh et al., "Boronated thiophenols: a preparation of 4-mercaptophenylboronic acid and derivatives," *Journal of Organometallic Chemistry* 581:82-86, 1999.
Davies et al., "Peroxides of Elements other than Carbon. Part XII. The Autoxidation of Optically Active 1-Phenylethylboronic Acid," *J Chem Soc* pp. 17-22, 1967.
Elgendy et al., "Design of a novel class of bifunctional thrombin inhibitors, synthesised by the first application of peptide boronates of solid phase chemistry," *Tetrahedron Letters* 38(18):3305-3308, 1997.
Hsiao et al., "A Facile Synthesis of tert-Butyl 2-[Benzyloxycarbonyl)amino]-3-(4,4,5,5-tetramethyl-1,3,2-dioxaborolan-2-yl)propionate: An Orthogonally Protected Boronic Acid Analog of Aspartic Acid," *Synthesis* 7:1043-1046, 1998.
Kettner et al., "Inhibition of the Serine Proteases Leukocyte Elastase, Pancreatic Elastase, Cathepsin G, and Chymotrypsin by Peptide Boronic Acids," *The Journal of Biological Chemistry* 259(24)15106-15114, 1984.
Kettner et al., "The Selective Inhibition of Thrombin of Peptides of Boroarginine," *The Journal of Biological Chemistry* 265(30):18289-18297, 1990.
Lappert, "Organic Compounds of Boron," *Chem. Review* 56:959-1064, 1956.
Martichonok et al., "Cysteine Proteases such as Papain are not Inhibited by Substrate Analogue Peptidyl Boronic Acids," *Bioorganic and Medicinal Chemistry* 5(4):679-684, 1997.
Skordalakes et al., "Crystallographic Structures of Human α-Thrombin Complexed to Peptide Boronic Acids Lacking a Positive Charge of P1. Evidence of Novel Interactions," *J. Am. Chem. Soc.* 119:9935-9936, 1997.
Snyder et al., "Organoboron Compounds, and the Study of Reaction Mechanisms. Primary Aliphatic Boronic Acids," *Am Chem Soc* 60:105-111, 1938.
Snyder et al., "Aryl Boronic Acids. II. Aryl Boronic Anhydrides and their Amine Complexes," *Am Chem Soc* 80:3611-3615, 1958.
Wityak et al., "Synthesis of Thrombin Inhibitor DuP 714," *J. Org. Chem.* 60:3717-3722, 1995.
Davies, *The Pharmaceutical Journal* 266:322-323, 2001.
Claeson et al., *Thromb Haemostas*, vol. 65, p. 1289, 1991.
Claeson et al., "Novel peptide mimetics as highly efficient inhibitors of thrombin based on modified D-Phe-Pro-Arg sequences," *in Peptides, Chemistry and Biology*, Smith J A, Rivier J E, Eds., Escom: Leiden pp. 824-825, 1992.
Claeson et al., *Biochem J.* 290:309-312, 1993.
Claeson et al., *The Design of Synthetic Inhibitors of Thrombin* 340:83-89, 1993.
Claeson, *Blood Coagulation and Fibrinolysis* 5:411-436, 1994.
Coburn, *Exp. Opin. Ther. Patents* 11(5):721-738, 2001.
Contreras et al., *J. Org. Chem.* 246:213-217, 1983.
Deadman et al., *J. Medicinal Chemistry* 38:1511-1522, 1995.
Deadman et al., *J. Enzyme Inhibition* 9:29-41, 1995.
Elgendy et al., *Thromb Haemostas* 65:775, 1991.
Elgendy et al., *Tetrahedron Letters* 33(29):4209-4212, 1992.
Elgendy et al., *The Design of Synthetic Inhibitors of Thrombin* 340:173-178, 1993.
Elgendy et al., *Tetrahedron* 50(12):3803-3812, 1994.
Esmail et al., *Thrombosis and Haemostasis* 6:1318, 1995.
Esmail et al., *Thrombosis and Haemostasis* 5:91-92, 1997.
Esmail et al., *Thrombosis and Haemostasis* 5:498-499, 1997.
Gerrard et al., *Thrombosis and Haemostasis* 6:1307, 1995.
Gustafsson et al., *Thrombosis Research* 101:171-181, 2001.
Katz et al., *Biochemistry* 34(26):8264-8280, 1995.
Martichonok et al., *J. Am. Chem. Soc.* 118:950-958, 1996.
Matt et al., *Bioorg. Med. Chem.* 8:2291-2303, 2000.
Matteson, *Chem. Rev.* 89:1535-1551, 1989.
Matteson et al., *J. Org. Chem.* 61:6047-6051, 1996.
Metternich et al., *Naunyn-Schmiedeberg's Arch Pharmacol* 97:345, 1992.
Philipp et al., *The Design of Synthetic Inhibitors of Thrombin* 340:67-77, 1993.
Rewinkel et al., *Current Pharmaceutical Design* 5:1043-1075, 1999.
Saitoh et al., *Pharmaceutical Research* 16(11):1786-1789, 1999.
Sanderson et al., *Current Medicinal Chemistry* 5:289-304, 1998.
Skordalakes et al., *Biochemistry* 37(41):14420-14427, 1998.
Spencer et al., *Tetrahedron* 58:1551-1556, 2002.
Stahl et al., *Handbook of Pharmaceutical Salts Properties, Selection, and Use*, Verlag Helvetica Chimica Acta, Postfach, CH-8042 Züirch, Switzerland, 2002.
Tapparelli et al., *The Journal of Biological Chemistry* 268(7):4734-4741, 1993.
Tapparelli et al., *Trends Pharmacol. Sci.* 14:366-376, 1993.
Trigen Limited, *TRI 50b Non Confidential Information* pp. 1-12, Jul. 2002.
Trigen Limited, "Looking for a career in Biotechnology?" poster exhibited at XVIIth International Symposium on Medicinal Chemistry, Barcelona, Spain, Sep. 5, 2002.
Tripathy et al., *Synthesis* pp. 200-206, 1990.
Wu et al., *Journal of Pharmaceutical Sciences* 89(6):758-765, Jun. 2000.
Yang et al., *Pharmaceutical Research* 16(9):1331-1343, 1999.
Yang et al., *Medicinal Research Reviews* 23(3):346-368, 2003.
Berge et al., "Pharmaceutical Salts," *Journal of Pharmaceutical Sciences* 66(1):1-19, 1977.
Office Action mailed Nov. 9, 2007 in U.S. Appl. No. 11/078,097, Combe-Marzelle, S.M., et al., filed Mar. 9, 2005.
Office Action mailed Nov. 9, 2007 in U.S. Appl. No. 11/077,620, Boucher, O.V.A., et al., filed Mar. 9, 2005.
Office Action mailed Nov. 29, 2007 in U.S. Appl. No. 11/077,620, Boucher, O.V.A., et al., filed Mar. 9, 2005.
Office Action mailed Sep. 19, 2007 in U.S. Appl. No. 10/937,854, Madge, D.J., filed Sep. 8, 2004.
Office Action mailed on Aug. 9, 2007 in U.S. Appl. No. 10/937,181, Madge, D.J., et al., filed Sep. 9, 2003.
Co-pending U.S. Appl. No. 10/591,962, inventors Patrick et al., filed Sep. 8, 2006 (Not Published).
Co-pending U.S. Appl. No. 10/592,265, inventors Combe-Marzelle et al., filed Mar. 9, 2005 (Not Published).
Office Action mailed on May 23, 2007 in U.S. Appl. No. 10/659,178, Madge, D.J., et al., filed Sep. 9, 2003.
Office Action mailed on Feb. 5, 2007 in U.S. Appl. No. 10/659,178, Madge, D.J., et al., filed Sep. 9, 2003.

* cited by examiner

BORONIC ACID SALTS USEFUL IN PARENTERAL FORMULATIONS

BACKGROUND

The present disclosure relates to pharmaceutically useful products obtainable from organoboronic acids. The disclosure also relates to the use of members of the aforesaid class of products, to their formulation, their preparation, their synthetic intermediates and to other subject matter.

The disclosure further relates to parenteral pharmaceutical formulations containing the described products.

Boronic Acid Compounds

It has been known for some years that boronic acid compounds and their derivatives, e.g. esters, have biological activities, notably as inhibitors or substrates of proteases. For example, Koehler et al. *Biochemistry* 10:2477, 1971 report that 2-phenylethane boronic acid inhibits the serine protease chymotrypsin at millimolar levels. The inhibition of chymotrypsin and subtilisin by arylboronic acids (phenylboronic acid, m-nitro-phenylboronic acid, m-aminophenylboronic acid, m-bromophenylboronic acid) is reported by Phillip et al, *Proc. Nat. Acad. Sci. USA* 68:478-480, 1971. A study of the inhibition of subtilisin Carlsberg by a variety of boronic acids, especially phenyl boronic acids substituted by Cl, Br, $CH_3$, $H_2N$, MeO and others, is described by Seufer-Wasserthal et al, *Biorg. Med. Chem.* 2(1):35-48, 1994.

In describing inhibitors or substrates of proteases, P1, P2, P3, etc. designate substrate or inhibitor residues which are amino-terminal to the scissile peptide bond, and S1, S2, S3, etc., designate the corresponding subsites of the cognate protease in accordance with: Schechter, I. and Berger, A. On the Size of the Active Site in Proteases, *Biochem.Biophys. Res.Comm.*, 27:157-162, 1967. In thrombin, the S1 binding site or "specificity pocket" is a well defined slit in the enzyme, whilst the S2 and S3 binding subsites (also respectively called the proximal and distal hydrophobic pockets) are hydrophobic and interact strongly with, respectively, Pro and (R)—Phe, amongst others.

Pharmaceutical research into serine protease inhibitors has moved from the simple arylboronic acids to boropeptides, i.e. peptides containing a boronic acid analogue of an α-amino carboxylic acid. The boronic acid may be derivatised, often to form an ester. Shenvi (EP-A-145441 and U.S. Pat. No. 4,499,082) disclosed that peptides containing an α-aminoboronic acid with a neutral side chain were effective inhibitors of elastase and has been followed by numerous patent publications relating to boropeptide inhibitors of serine proteases. Specific, tight binding boronic acid inhibitors have been reported for elastase ($K_i$, 0.25 nM), chymotrypsin ($K_i$, 0.25 nM), cathepsin G ($K_i$, 21 nM), α-lytic protease ($K_i$, 0.25 nM), dipeptidyl aminopeptidase type IV ($K_i$, 16 pM) and more recently thrombin (Ac-D-Phe-Pro-boroArg-OH (DuP 714 initial $K_i$ 1.2 nM).

Claeson et al (U.S. Pat. No. 5,574,014 and others) and Kakkar et al (WO 92/07869 and family members including U.S. Pat. No. 5,648,338) disclose thrombin inhibitors having a neutral C-terminal side chain, for example an alkyl or alkoxyalkyl side chain.

Modifications of the compounds described by Kakkar et al are included in WO 96/25427, directed to peptidyl serine protease inhibitors in which the P2-P1 natural peptide linkage is replaced by another linkage. As examples of non-natural peptide linkages may be mentioned —$CO_2$—, —$CH_2O$—, —NHCO—, —$CHYCH_2$—, —CH=CH—, —CO$(CH_2)_p$CO— where p is 1, 2 or 3, —COCHY—, —$CO_2$—$CH_2NH$—, —CHY—NX—, —N(X)$CH_2$—N(X)CO—, —CH=C(CN)CO—, —CH(OH)—NH—, —CH(CN)—NH—, —CH(OH)—$CH_2$— or —NH—CHOH—, where X is H or an amino protecting group and Y is H or halogen, especially F. Particular non-natural peptide linkages are —$CO_2$— or —$CH_2O$—.

Metternich (EP 471651 and U.S. Pat. No. 5,288,707, the latter being assigned to Trigen Limited) discloses variants of Phe—Pro—BoroArg boropeptides in which the P3 Phe is replaced by an unnatural hydrophobic amino acid such as trimethylsilylalanine, p-tert.butyl-diphenyl-silyloxymethyl-phenylalanine or p-hydroxymethylphenylalanine and the P1 side chain may be neutral (alkoxyalkyl, alkylthioalkyl or trimethylsilylalkyl).

The replacement of the P2 Pro residue of borotripeptide thrombin inhibitors by an N-substituted glycine is described in Fevig J M et al *Bioorg. Med. Chem.* 8: 301-306 and Rupin A et al *Thromb. Haemost.* 78(4): 1221-1227, 1997. See also U.S. Pat. No. 5,585,360 (de Nanteuil et al).

Amparo (WO 96/20698 and family members including U.S. Pat. No. 5,698,538) discloses peptidomimetics of the structure Aryl-linker-Boro(Aa), where Boro(Aa) may be an aminoboronate residue with a non-basic side chain, for example BoroMpg. The linker is of the formula —$(CH_2)_m$CONR— (where m is 0 to 8 and R is H or certain organic groups) or analogues thereof in which the peptide linkage —CONR— is replaced by —CSNR—, —$SO_2$NR—, —$CO_2$—, —C(S)O— or —$SO_2$O—. Aryl is phenyl, naphthyl or biphenyl substituted by one, two or three moieties selected from a specified group. Most typically these compounds are of the structure Aryl-$(CH_2)_n$—CONH—CHR$^2$—BY$^1$Y$^2$, where R$^2$ is for example a neutral side chain as described above and n is 0 or 1.

Non-peptide boronates have been proposed as inhibitors of proteolytic enzymes in detergent compositions. WO 92/19707 and WO 95/12655 report that arylboronates can be used as inhibitors of proteolytic enzymes in detergent compositions. WO 92/19707 discloses compounds substituted meta to the boronate group by a hydrogen bonding group, especially acetamido (—$NHCOCH_3$), sufonamido (—$NHSO_2CH_3$) and alkylamino. WO 95/12655 teaches that ortho-substituted compounds are superior.

Boronate enzyme inhibitors have wide application, from detergents to bacterial sporulation inhibitors to pharmaceuticals. In the pharmaceutical field, there is patent literature describing boronate inhibitors of serine proteases, for example thrombin, factor Xa, kallikrein, elastase, plasmin as well as other serine proteases like prolyl endopeptidase and Ig AI Protease. Thrombin is the last protease in the coagulation pathway and acts to hydrolyse four small peptides form each molecule of fibrinogen, thus deprotecting its polymerisation sites. Once formed, the linear fibrin polymers may be cross-linked by factor XIIIa, which is itself activated by thrombin. In addition, thrombin is a potent activator of platelets, upon which it acts at specific receptors. Thrombin also potentiates its own production by the activation of factors V and VIII.

Other aminoboronate or peptidoboronate inhibitors or substrates of serine proteases are described in:

U.S. Pat. No. 4,935,493
EP 341661
WO 94/25049
WO 95/09859
WO 96/12499
WO 96/20689
Lee S-L et al, *Biochemistry* 36:13180-13186, 1997

Dominguez C et al, *Bioorg. Med. Chem. Lett.* 7:79-84, 1997
EP 471651
WO 94/20526
WO 95/20603
WO 97/05161
U.S. Pat. No. 4,450,105
U.S. Pat. No. 5,106,948
U.S. Pat. No. 5,169,841.

Peptide boronic acid inhibitors of hepatic C virus protease are described in WO 01/02424.

Matteson D S *Chem. Rev.* 89: 1535-1551, 1989 reviews the use of α-halo boronic esters as intermediates for the synthesis of inter alia amino boronic acids and their derivatives. Matteson describes the use of pinacol boronic esters in non-chiral synthesis and the use of pinanediol boronic esters for chiral control, including in the synthesis of amino and amido boronate esters.

Contreras et al *J. Organomet. Chem.* 246: 213-217, 1983 describe how intramolecular N→B coordination was demonstrated by spectroscopic studies on cyclic boronic esters prepared by reacting Me$_2$CHCMe$_2$—BH$_2$ with diethanolamines.

Boronic acid and ester compounds have displayed promise as inhibitors of the proteasome, a multicatalytic protease responsible for the majority of intracellular protein turnover. Ciechanover, *Cell*, 79:13-21, 1994, teaches that the proteasome is the proteolytic component of the ubiquitin-proteasome pathway, in which proteins are targeted for degradation by conjugation to multiple molecules of ubiquitin. Ciechanover also teaches that the ubiquitin-proteasome pathway plays a key role in a variety of important physiological processes.

Adams et al, U.S. Pat. No. 5,780,454 (1998), U.S. Pat. No. 6,066,730 (2000), U.S. Pat. No. 6,083,903 (2000) and equivalent WO 96/13266, and U.S. Pat. No. 6,297,217 (2001) describe peptide boronic ester and acid compounds useful as proteasome inhibitors. These documents also describe the use of boronic ester and acid compounds to reduce the rate of muscle protein degradation, to reduce the activity of NF-$_\kappa$B in a cell, to reduce the rate of degradation of p53 protein in a cell, to inhibit cyclin degradation in a cell, to inhibit the growth of a cancer cell, to inhibit antigen presentation in a cell, to inhibit NF-$_\kappa$B dependent cell adhesion, and to inhibit HIV replication. Brand et al, WO 98/35691, teaches that proteasome inhibitors, including boronic acid compounds, are useful for treating infarcts such as occur during stroke or myocardial infarction. Elliott et al, WO 99/15183, teaches that proteasome inhibitors are useful for treating inflammatory and autoimmune diseases.

Unfortunately, organoboronic acids can be relatively difficult to obtain in analytically pure form. Thus, alkylboronic acids and their boroxines are often air-sensitive. Korcek et al, *J. Chem. Soc. Perkin Trans.* 2:242, 1972, teaches that butylboronic acid is readily oxidized by air to generate 1-butanol and boric acid.

It is known that derivatisation of boronic acids as cyclic esters provides oxidation resistance. For example, Martichonok V et al *J. Am. Chem. Soc.* 118: 950-958, 1996 state that diethanolamine derivatisation provides protection against possible boronic acid oxidation.

Wu et al, *J. Pharm. Sci.*, 89:758-765, 2000, discuss the stability of the compound N-(2-pyrazine) carbonyl-phenylalanine-leucine boronic acid (LDP-341, also known as bortezomib), an anti-cancer agent. It is described how "during an effort to formulate [LDP-341] for parenteral administration, the compound showed erratic stability behaviour".

The degradation pathways were investigated and it was concluded that the degradation was oxidative, the initial oxidation being attributed to peroxides or molecular oxygen and its radicals.

WO 02/059131 discloses boronic acid products which are described as stable. In particular, these products are certain boropeptides and/or boropeptidomimetics in which the boronic acid group has been derivatised with a sugar. The disclosed sugar derivatives, which have hydrophobic amino acid side chains, are of the formula

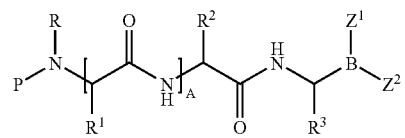

wherein:

P is hydrogen or an amino-group protecting moiety;

R is hydrogen or alkyl;

A is 0, 1 or 2;

R$^1$, R$^2$ and R$^3$ are independently hydrogen, alkyl, cycloalkyl, aryl or —CH$_2$—R$^5$;

R$^5$, in each instance, is one of aryl, aralkyl, alkaryl, cycloalkyl, heterocyclyl, heteroaryl, or -W-R$^6$, where W is a chalcogen and R$^6$ is alkyl;

where the ring portion of any of said aryl, aralkyl, alkaryl, cycloalkyl, heterocyclyl, or heteroaryl in R$^1$, R$^2$, R$^3$ or R$^5$ can be optionally substituted; and Z$^1$ and Z$^2$ together form a moiety derived from a sugar, wherein the atom attached to boron in each case is an oxygen atom.

Some of the disclosed compounds are sugar derivatives of LDP-341 (see above).

Many drugs comprise an active moiety which is a carboxylic acid. There are a number of differences between carboxylic acids and boronic acids, whose effects on drug delivery, stability and transport (amongst others) have not been investigated. One feature of trivalent boron compounds is that the boron atom is sp$^2$ hybridised, which leaves an empty 2p$_z$ orbital on the boron atom. A molecule of the type BX$_3$ can therefore act as an electron-pair acceptor, or Lewis acid. It can use the empty 2p$_z$ orbital to pick up a pair of nonbonding electrons from a Lewis base to form a covalent bond. BF$_3$ therefore reacts with Lewis bases such as NH$_3$ to form acid-base complexes in which all of the atoms have a filled shell of valence electrons.

Boric acid, accordingly, can act as a Lewis add, accepting OH$^-$:

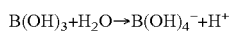

Further, boronic acids of the type RB(OH)$_2$ are dibasic and have two pKa's. Another point of distinction about boron compounds is the unusually short length of bonds to boron, for which three factors may be responsible:

1. Formation of pπ-pπ bonds;
2. Ionic-covalent resonance;
3. Reduced repulsions between non-bonding electrons.

The presumed equilibria of boronic and carboxylic acids in aqueous KOH are shown below (excluding formation of RBO$_2$$^{2-}$):

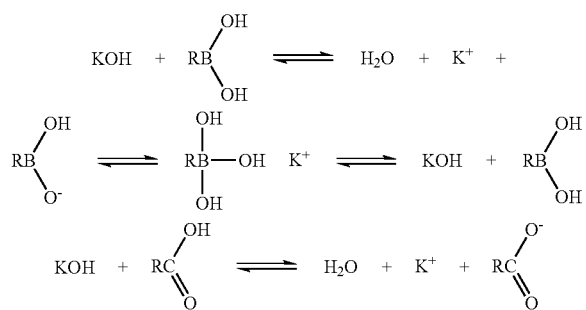

Thrombosis

Hemostasis is the normal physiological condition of blood in which its components exist in dynamic equilibrium. When the equilibrium is disturbed, for instance following injury to a blood vessel, certain biochemical pathways are triggered leading, in this example, to arrest of bleeding via clot formation (coagulation). Coagulation is a dynamic and complex process in which proteolytic enzymes such as thrombin play a key role. Blood coagulation may occur through either of two cascades of zymogen activations, the extrinsic and intrinsic pathways of the coagulation cascade. Factor VIIa in the extrinsic pathway, and Factor IXa in the intrinsic pathway are important determinants of the activation of factor X to factor Xa, which itself catalyzes the activation of prothrombin to thrombin, whilst thrombin in turn catalyses the polymerization of fibrinogen monomers to fibrin polymer. The last protease in each pathway is therefore thrombin, which acts to hydrolyze four small peptides (two FpA and two FpB) from each molecule of fibrinogen, thus deprotecting its polymerization sites. Once formed, the linear fibrin polymers may be cross-linked by factor XIIIa, which is itself activated by thrombin. In addition, thrombin is a potent activator of platelets, upon which it acts at specific receptors. Thrombin activation of platelets leads to aggregation of the cells and secretion of additional factors that further accelerate the creation of a hemostatic plug. Thrombin also potentiates its own production by the activation of factors V and VIII (see Hemker and Beguin in: Jolles, et. al., "Biology and Pathology of Platelet Vessel Wall Interactions," pp. 219-26 (1986), Crawford and Scrutton in: Bloom and Thomas, "Haemostasis and Thrombosis," pp. 47-77, (1987), Bevers, et. al., *Eur. J. Biochem.* 122:429-36, 1982, Mann, *Trends Biochem. Sci.* 12:229-33, 1987).

Proteases are enzymes which cleave proteins at specific peptide bonds. Cuypers et al., *J. Biol. Chem.* 257:7086, 1982, and the references cited therein, classify proteases on a mechanistic basis into five classes: serine, cysteinyl or thiol, acid or aspartyl, threonine and metalloproteases. Members of each class catalyse the hydrolysis of peptide bonds by a similar mechanism, have similar active site amino acid residues and are susceptible to class-specific inhibitors. For example, all serine proteases that have been characterised have an active site serine residue.

The coagulation proteases thrombin, factor Xa, factor VIIa, and factor IXa are serine proteases having trypsin-like specificity for the cleavage of sequence-specific Arg—Xxx peptide bonds. As with other serine proteases, the cleavage event begins with an attack at the active site serine on the scissile bond of the substrate, resulting in the formation of a tetrahedral intermediate. This is followed by collapse of the tetrahedral intermediate to form an acyl enzyme and release of the amino terminus of the cleaved sequence. Hydrolysis of the acyl enzyme then releases the carboxy terminus.

As indicated above, platelets play two important roles in normal hemostasis. First, by aggregating, they constitute the initial hemostatic plug which immediately curtails bleeding from broken blood vessels. Secondly, the platelet surface can become activated and potentiate blood clotting, a property referred to as platelet procoagulant activity. This may be observed as an increase in the rate of activation of prothrombin by factor Xa in the presence of factor Va and $Ca^{2+}$, referred to as the prothrombinase reaction. Normally, there are few (if any) clotting factors on the surface of unstimulated platelets but, when platelets are activated, negatively charged phospholipids (phosphatidylserine and phospatidylinositol) that are normally on the cytoplasmic side of the membrane become available and provide a surface on which two steps of the coagulation sequence occur. The phospholipid on the surface of activated platelets profoundly accelerates the reactions leading to the formation of thrombin, so that thrombin can be generated at a rate faster than its neutralisation by antithrombin III. The reactions that occur on the platelet surfaces are not easily inhibited by the natural anticoagulants in blood such as antithrombin III, either with or without heparin. (See Kelton and Hirsch in: Bloom and Thomas, "Haemostasis and Thrombosis," pp. 737-760, (1981); Mustard et al in: Bloom and Thomas, "Haemostasis and Thrombosis," pp. 503526, (1981); Goodwin et al; *Biochem. J.* 308:15-21, 1995).

A thrombus can be considered as an abnormal product of a normal mechanism and can be defined as a mass or deposit formed from blood constituents on a surface of the cardiovascular system, for example of the heart or a blood vessel. Thrombosis can be regarded as the pathological condition wherein improper activity of the hemostatic mechanism results in intravascular thrombus formation. Three basic types of thrombi are recognised:

the white thrombus which is usually seen in arteries and consists chiefly of platelets;

the red thrombus which is found in veins and is composed predominantly of fibrin and red cells;

the mixed thrombus which is composed of components of both white and red thrombi.

The composition of thrombi is influenced by the velocity of blood flow at their sites of formation. In general white platelet-rich thrombi form in high flow systems, while red coagulation thrombi form in regions of stasis. The high shear rate in arteries prevents the accumulation of coagulation intermediates on the arterial side of the circulation: only platelets have the capacity to form thrombi binding to the area of damage via von Willebrand factor. Such thrombi composed only of platelets are not stable and disperse. If the stimulus is strong then the thrombi will form again and then disperse continually until the stimulus has diminished. For the thrombus to stabilise, fibrin must form. In this respect, small amounts of thrombin can accumulate within the platelet thrombus and activate factor Va and stimulate the platelet procoagulant activity. These two events lead to an overall increase in the rate of activation of prothrombin by factor Xa of 300,000 fold. Fibrin deposition stabilises the platelet thrombus. Indirect thrombin inhibitors, for example heparin, are not clinically effective at inhibiting stimulation of platelet procoagulant activity. Accordingly, a therapeutic agent which inhibits platelet procoagulant activity would be useful for treating or preventing arterial thrombotic conditions.

On the venous side of circulation, the thrombus is comprised of fibrin: thrombin can accumulate because of the slower flow on the venous side and platelets play only a minor role.

Thrombosis is thus not considered to be a single indication but, rather, is a class of indications embracing distinct sub-classes for which differing therapeutic agents and/or protocols may be appropriate. Thus, regulatory authorities treat disorders such as, for example, deep vein thrombosis, cerebrovascular arterial thrombosis and pulmonary embolism as distinct indications for the purposes of licensing medicines. Two main sub-classes of thrombosis are arterial thrombosis and venous thrombosis. Arterial thrombosis includes such specific disorders as acute coronary syndromes [for example acute myocardial infarction (heart attack, caused by thrombosis in a coronary artery)], cerebrovascular arterial thrombosis (stroke, caused by thrombosis in the cerebrovascular arterial system) and peripheral arterial thrombosis. Examples of conditions caused by venous thrombosis are deep vein thrombosis and pulmonary embolism.

The management of thrombosis commonly involves the use of antiplatelet drugs (inhibitors of platelet aggregation) to control future thrombogenesis and thrombolytic agents to lyse the newly formed clot, either or both such agents being used in conjunction or combination with anticoagulants. Anticoagulants are used also preventatively (prophylactically) in the treatment of patients thought susceptible to thrombosis.

Currently, two of the most effective classes of drugs in clinical use as anticoagulants are the heparins and the vitamin K antagonists. The heparins are ill-defined mixtures of sulfated polysaccharides that bind to, and thus potentiate, the action of antithrombin III. Antithrombin III is a naturally occurring inhibitor of the activated clotting factors IXa, Xa, XIa, thrombin and probably XIIa (see Jaques, *Pharmacol. Rev.* 31:99-166, 1980). The vitamin K antagonists, of which warfarin is the most well-known example, act indirectly by inhibiting the post-ribosomal carboxylations of the vitamin K dependent coagulation factors II, VII, IX and X (see Hirsch, *Semin. Thromb. Hemostasis*12:1-11, 1986). While effective therapies for the treatment of thrombosis, heparins and vitamin K antagonists have the unfortunate side effects of bleeding, heparin-induced thrombocytopenia (in the case of heparin) and marked interpatient variability, resulting in a small and unpredictable therapeutic safety margin.

The use of direct acting inhibitors of thrombin and other serine protease enzymes of the coagulation system is expected to alleviate these problems. To that end, a wide variety of serine protease inhibitors have been tested, including boropeptides, i.e. peptides containing a boronic acid analogue of an α-amino acid. Whilst direct acting boronic acid thrombin inhibitors have been discussed earlier in this specification, they are further described in the following section.

Neutral P1 Residue Boropeptide Thrombin Inhibitors

Claeson et al (U.S. Pat. No. 5,574,014 and others) and Kakkar et al (WO 92/07869 and family members including U.S. Pat. No. 5,648,338) disclose lipophilic thrombin inhibitors having a neutral (uncharged) C-terminal (P1) side chain, for example an alkoxyalkyl side chain.

The Claeson et al and Kakkar et al patent families disclose boronate esters containing the amino acid sequence D-Phe-Pro-BoroMpg [(R)-Phe-Pro-BoroMpg], which are highly specific inhibitors of thrombin. Of these compounds may be mentioned in particular Cbz-(R)-Phe-Pro-BoroMpg-OPinacol (also known as TRI 50b). The corresponding free boronic acid is known as TRI 50c. For further information relating to TRI 50b and related compounds, the reader is referred to the following documents:

Elgendy S et al., in *The Design of Synthetic Inhibitors of Thrombin*, Claeson G et al Eds, Advances in Expedimental Medidne, 340:173-178, 1993.

Claeson G et al, *Biochem J.* 290:309-312, 1993

Tapparelli C et al, *J Biol Chem*, 268:4734-4741, 1993

Claeson G, in *The Design of Synthetic Inhibitors of Thrombin*, Claeson G et al Eds, Advances in Experimental Medicine, 340:83-91, 1993

Phillip et al, in *The Design of Synthetic Inhibitors of Thrombin*, Claeson G et al Eds, Advances in Experimental Medicine, 340:67-77, 1993

Tapparelli C et al, *Trends Pharmacol. Sci.* 14:366-376, 1993

Claeson G. Blood *Coagulation and Fibrinolysis* 5:411-436, 1994

Elgendy et al, *Tetrahedron* 50:3803-3812, 1994

Deadman J et al, *J. Enzyme Inhibition* 9:29-41, 1995

Deadman J et al, *J. Medicinal Chemistry* 38:1511-1522, 1995.

The tripeptide sequence of TRI 50b has three chiral centres. The Phe residue is considered to be of (R)-configuration and the Pro residue of natural (S)-configuration, at least in compounds with commercially useful inhibitor activity; the Mpg residue is believed to be of (R)-configuration in isomers with commercially useful inhibitor activity. Thus, the active, or most active, TRI 50b stereoisomer is considered to be of R,S,R configuration and may be represented as:

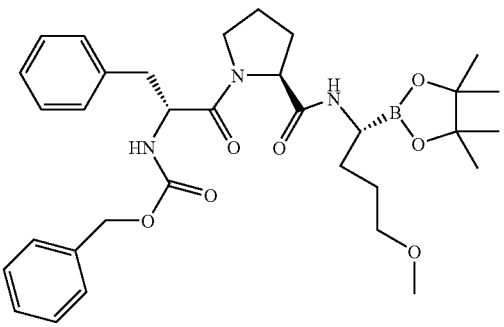

(R,S,R)-TRI 50b: Cbz-(R)-Phe-(S)-Pro-(R)-boroMpg-Pinacol

Whilst indirect acting thrombin inhibitors have been found useful parenterally for the treatment of patients susceptible to or suffering from venous thrombosis, the same is not true of arterial thrombosis, because it would be necessary to raise the dosage used in the treatment of venous thrombosis by many times in order to treat (prevent) arterial thrombosis. Such raised dosages typically cause bleeding, which makes indirect acting thrombin inhibitors unsuitable or less preferable for treating arterial thrombosis. Heparin and its low molecular weight derivatives are indirect thrombin inhibitors, and so are unsuitable to treat arterial thrombosis. Oral direct thrombin inhibitors are in development for arterial indications but may have lower than desirable therapeutic indices, i.e. may have higher than desirable levels of bleeding at therapeutic doses. Many organoboronic acid compounds may be classified as lipophilic or hydrophobic. Typically, such compounds include amongst others:

- boropepudes of which all or a majority of the amino acids are hydrophobic
- boropeptides of which at least half of the amino acids are hydrophobic and which have a hydrophobic N-terminal substituent (amino protecting group)
- non-peptides based on hydrophobic moieties.

BRIEF SUMMARY OF THE DISCLOSURE

It has been discovered that TRI 50b tends to hydrolyse. Thus in acid conditions, for example of an HPLC assay, TRI 50b is converted to the acid form with a short half life, which implies potential hydrolysis in parenteral preparations containing water into species, comprising the free acid and its corresponding boronate anions in equilibrium therewith, taught in the literature to be unstable to degradation via de-boronation (carbon-boron bond cleavage), by an oxidative pathway (see e.g. Wu et al, discussed above).

The instability of TRI 50b to hydrolysis also presents potential disadvantages in preparation of the compound and its formulation, as well as in the storage of pharmaceutical formulations containing it.

TRI 50c suffers further from instability, in that there is a problematic tendency for the boropeptide moiety itself to degrade via de-boronation (carbon-boron bond cleavage), such deboronation being taught by the literature to be oxidative (eg Wu et al, discussed above). The level of degradation can be remarkably high.

The properties discussed above of TRI 50b and TRI 50c will not be restricted to such compounds but will be shared by other boropeptide esters and acids, even if the properties of such other boropeptides differ quantitatively.

The present disclosure provides a solution to the problem of boronate diol ester and especially TRI50b instability which also provides the corresponding boronic acid with resistance to deboronation.

The present disclosure is predicated on, amongst other things, the finding that certain organoboronic acid products are indicated to be of enhanced stability.

The benefits of the present disclosure include a solution to the problem of boronate diol ester and especially TRI 50b instability, that is to say the presently disclosed products provide inter alia pharmacologically active compounds which are more stable than TRI 50b and other comparable esters in the sense of stability to hydrolysis. The disclosure further includes a solution to the problem of organoboronic acid instability, that is to say the presently disclosed products provide inter alia pharmacologically active compounds which are more stable to deboronation than TRI 50c. The stability provided within the framework of the disclosure is not absolute but is improved relative to the comparator compounds. The benefits offered by the disclosure further include the provision of products which have an unexpected usefulness in parenteral formulations.

There is disclosed an amino boronic acid derivative which avoids the disadvantages of pinacol esters. The disclosure further includes a peptide boronic acid derivative which is indicated to be of enhanced stability. In particular, the disclosure includes amongst other subject matter boronic acid derivatives which are of relative stability to hydrolysis and deboronation and are useful in parenteral formulations for inhibiting thrombin.

The disclosure concerns a pharmaceutically acceptable base addition salt of certain organoboronic acid drugs, specifically hydrophobic boropeptides (e.g di- or tri-peptides), and more specifically thrombin inhibitors having a non-basic P1 group. As a class, such salts are not only contrary to the direction of the prior art but additionally have an improved level of stability which cannot be explained or predicted on the basis of known chemistry.

In one aspect, the disclosure relates to pharmaceutically acceptable base addition salt s of boronic acids which have a neutral aminoboronic acid residue capable of binding to the thrombin Si subsite linked through a peptide linkage to a hydrophobic moiety capable of binding to the thrombin S2 and S3 subsites. In a first embodiment, there is disclosed a parenteral pharmaceutical formulation that includes a pharmaceutically acceptable base addition salt of a boronic acid of, for example, formula (I):

(I)

wherein

Y comprises a hydrophobic moiety which, together with the aminoboronic acid residue —$NHCH(R^9)$—$B(OH)_2$, has affinity for the substrate binding site of thrombin; and $R^9$ is a straight chain alkyl group interrupted by one or more ether linkages (e.g. 1 or 2) and in which the total number of oxygen and carbon atoms is 3, 4, 5 or 6 (e.g. 5) or $R^9$ is —$(CH_2)_m$-W where m is 2, 3, 4 or 5 (e.g. 4) and W is —OH or halogen (F, Cl, Br or I). $R^9$ is an alkoxyalkyl group in one subset of compounds, e.g. alkoxyalkyl containing 4 carbon atoms.

Disclosed as certain examples are pharmaceutically acceptable base addition salt s of hydrophobic boronic acid inhibitors of thrombin. Such inhibitors may contain hydrophobic amino acids, and this class of amino acids includes those whose side chain is hydrocarbyl, hydrocarbyl containing an in-chain oxygen and/or linked to the remainder of the molecule by an in-chain oxygen or heteroaryl, or any of the aforesaid groups when substituted by hydroxy, halogen or trifluoromethyl. Representative hydrophobic side chains include alkyl, alkoxyalkyl, either of the aforesaid when substituted by at least one aryl or heteroaryl, aryl, heteroaryl, aryl substituted by at least one alkyl and heteroaryl substituted by at least one alkyl. Proline and other imino acids which are ring-substituted by nothing or by one of the moieties listed in the previous sentence are also hydrophobic.

Some hydrophobic side chains contain from 1 to 20 carbon atoms, e.g. non-cyclic moieties having 1, 2, 3 or 4 carbon atoms. Side chains comprising a cyclic group typically but not necessarily contain from 5 to 13 ring members and in many cases are phenyl or alkyl substituted by one or two phenyls.

Included are inhibitors which contain hydrophobic non-peptide moieties, which are typically based on moieties which may form a side chain of a hydrophobic amino acid, as described above.

Hydrophobic compounds may contain, for example, one amino group and/or one acid group (e.g. —COOH, —$B(OH)_2$). Generally, they do not contain multiple polar groups of any one type.

The disclosure comprises pharmaceutically acceptable base addition salt s of hydrophobic boronic acid inhibitors of thrombin, and therefore includes such salts of peptide boronic acids which have a partition coefficient between 1-n-octanol and water expressed as log P of greater than 1.0 at physiological pH and 25° C. Some peptide boronic acids useful in the invention have a partition coefficient of at least 1.5. A class of hydrophobic peptide boronic acids useful in the invention has a partition coefficient of no more than 5.

Some sub-classes of hydrophobic organoboronic acids are those described by Formulae (I) and (III) below, under the heading "Detailed Description of Several Examples".

Also disclosed as another embodiment is a pharmaceutically acceptable base addition salt of a peptide boronic acid of formula (II):

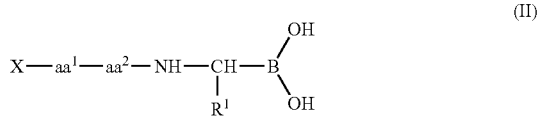

(II)

where:

X is a moiety bonded to the N-terminal amino group and may be H to form $NH_2$. The identity of X is not critical but may be a particular X moiety described above. In one example there may be mentioned benzyloxycarbonyl.

$aa^1$ is an amino acid having a hydrocarbyl side chain containing no more than 20 carbon atoms (e.g. up to 15 and optionally up to 13 C atoms) and comprising at least one cyclic group having up to 13 carbon atoms. In certain examples, the cyclic group(s) of $aa^1$ have/has 5 or 6 ring members. For instance, the cyclic group(s) of $aa^1$ may be aryl groups, particularly phenyl. Typically, there are one or two cyclic groups in the $aa^1$ side chain. Certain side chains comprise, or consist of, methyl substituted by one or two 5- or 6-membered rings.

More particularly, $aa^1$ is Phe, Dpa or a wholly or partially hydrogenated analogue thereof. The wholly hydrogenated analogues are Cha and Dcha.

$aa^2$ is an imino acid having from 4 to 6 ring members. Alternatively, $aa^2$ is Gly N-substituted by a $C_3$-$C_{13}$ hydrocarbyl group, e.g. a $C_3$-$C_8$ hydrocarbyl group comprising a $C_3$-$C_6$ hydrocarbyl ring; the hydrocarbyl group may be saturated, for example exemplary N-substituents are cyclopropyl, cyclobutyl, cyclopentyl and cyclohexyl. As a hydrocarbyl group containing one or more unsaturated bonds may be mentioned phenyl and methyl or ethyl substituted by phenyl, e.g. 2-phenylethyl, as well as β,β-dialkylphenylethyl.

There is a debate in the literature as to whether boronates in aqueous solution form the 'trigonal' $B(OH)_2$ or 'tetrahedral' $B(OH)_3^-$ boron species, but NMR evidence seems to indicate that at a pH below the first pKa of the boronic acid the main boron species is the neutral $B(OH)_2$. In the duodenum the pH is likely to be between 6 and 7, so the trigonal species is likely to be predominant here. In any event, the symbol —$B(OH)_2$ includes tetrahedral as well as trigonal boron species, and throughout this specification symbols indicating trigonal boron species embrace also tetrahedral species. The symbol may further include boronic groups in anhydride form.

The salts may be in the form of solvates, particularly hydrates.

The salts may comprise, or consist essentially of, acid salts in which the boronic acid is singly deprotonated. The disclosure therefore includes products having a metal/boronate stoichiometry consistent with the boronate groups in the product predominantly (more than 50 mol %) carrying a single negative charge.

Parenteral formulations of the salts are also provided herein. In particular, there are provided parenteral formulations comprising the salts in the solid phase, for example particulate salts for reconstitution as aqueous solutions prior to administration by injection or infusion. Such reconstituted solutions are also included in the disclosure.

According to a further aspect of the present disclosure, there is provided a method of treatment of a condition where anti-thrombotic activity is required which method comprises parenteral administration of a therapeutically effective amount of a pharmaceutically acceptable base addition salt of a boronic acid of formula (I) to a person suffering from, or at risk of suffering from, such a condition.

As described further hereinafter, there are provided also haemodialysis solutions comprising a salt of the disclosure.

The salts described herein include products obtainable by (having the characteristics of a product obtained by) reaction of the boronic acid with a strong base and the term "salt" herein is to be understood accordingly. The term "salt" in relation to the disclosed products, therefore, does not necessarily imply that the products contain discrete cations and anions and is to be understood as embracing products which are obtainable using a reaction of a boronic acid and a base. The disclosure embraces products which, to a greater or lesser extent, are in the form of a coordination compound. The disclosure thus provides also products obtainable by (having the characteristics of a product obtained by) reaction of a boronic acid (I) with a strong base a well as the therapeutic, including prophylactic, use of such products.

The present disclosure is not limited as to the method of preparation of the salts, provided that they contain a boronate species derived from boronic acid (I) and a counterion. Such boronate species may be boronate anions in any equilibrium form thereof. The term "equilibrium form" refers to differing forms of the same compounds which may be represented in an equilibrium equation (e.g. boronic acid in equilibrium with a boronic anhydride and in equilibrium with different boronate ions). Boronates in the solid phase may form anhydrides and the disclosed boronate salts when in the solid phase may comprise boronate anhydrides, as a boronic equilibrium species. It is not required that the salts be prepared by reaction of a base containing the counter-ion and the boronic acid (I). Further, the disclosure includes salt products which might be regarded as indirectly prepared by such an acid/base reaction as well as salts obtainable by (having the characteristics of products obtained by) such indirect preparation. As examples of possibly indirect preparation may be mentioned processes in which, after initial recovery of the salt, it is purified and/or treated to modify its physicochemical properties, for example to modify solid form or hydrate form, or both.

In some embodiments, the cations of the salts are monovalent.

In some embodiments the salts comprise anhydride species; in others they are essentially free of anhydride species.

The salts may be in isolated form. The salts may have a purity, e.g. as determined by the method of Example 34, of at least about 90%, e.g. of greater than or equal to about 95%. In the case of pharmaceutical formulations, such salt forms may be combined with pharmaceutically acceptable diluents, excipients or carriers.

The disclosure includes a method for preparing the salts from the corresponding boronic acid as an intermediate, as well as the intermediate boronic acid of Formula (I) and a method for preparing it.

Further aspects and embodiments of the disclosure are set forth in the following description and claims. Also included as such are the salts described herein.

Throughout the description and claims of this specification, the words "comprise" and "contain" and variations of the words, for example "comprising" and "comprises", mean "including but not limited to", and are not intended to (and do not) exclude other moieties, additives, components, integers or steps.

This patent application contains data indicating that the stability (resistance to deboronation) of organoboronic acids may be increased by providing them in the form of salts, e.g. metal salts. In single experiments, the ammonium salt of TRI 50c appeared to decompose on drying to yield ammonia, whilst the choline salt demonstrated rapid decomposition to a deboronated impurity. Although experiments have not been conducted to reproduce these unrepeated observations, there is provided a sub-class in which the ammonium and choline salts are excluded. The salt may be an acid salt. In any event, this stabilisation technique forms part of the disclosure and is applicable, inter alia, to organoboronic acids described under the heading "BACKGROUND" and to organoboronic acids described in publications mentioned under that heading.

DETAILED DESCRIPTION OF SEVERAL EXAMPLES

Glossary

Figure 1:
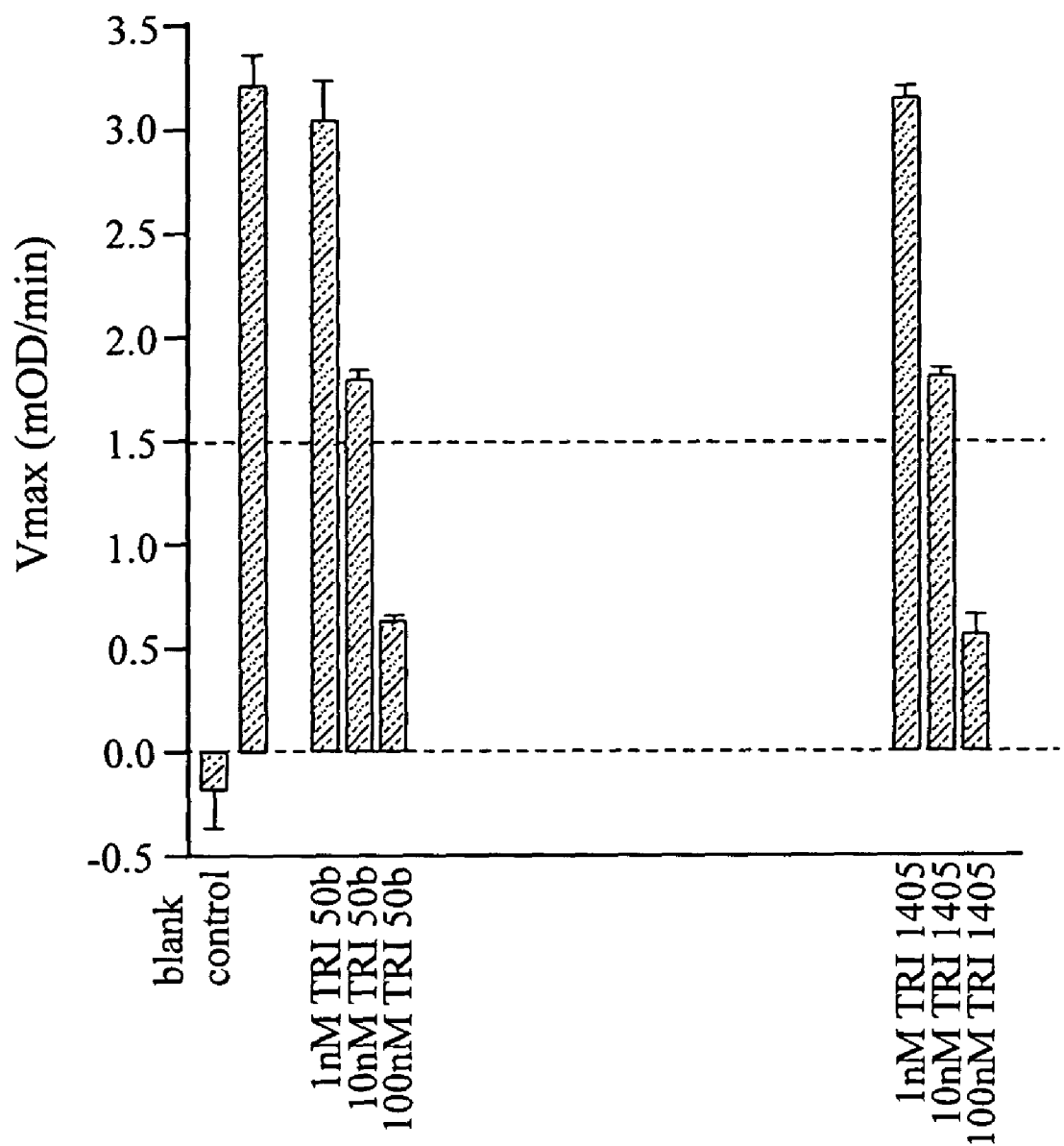
FIG. 1 is a chart referred to in Example 35, showing the results of a thrombin amidolytic assay of TRI 1405 (TRI 50c magnesium salt) and TRI 50b, where Vmax is the maximum rate of reaction measured by amidolytic assay.

The following terms and abbreviations are used in this specification:

The expression "acid salt" as applied to a salt of a boronic acid refers to salts of which a single —OH group of the trigonally-represented acid group —B(OH)$_2$ is deprotonated. Thus salts wherein the boronate group carries a single negative charge and may be represented as —B(OH)(O$^-$) or as [—B(OH)$_3$]$^-$ are acid salts. The expression encompasses salts of a cation having a valency n wherein the molar ratio of boronic acid to cation is approximately n to 1. In practical terms, the observed stoichiometry is unlikely to be exactly n:1 but will be consistent with a notional n:1 stoichiometry. For example, the observed mass of the cation might vary from the calculated mass for a n:1 stoichiometry by no more than about 10%, e.g. no more than about 7.5%; in some cases an observed mass of a cation might vary from the calculated mass by no more than about 1%. Calculated masses are suitably based on the trigonal form of the boronate. (At an atomic level, a salt stoichiometrically consistent with being an acid salt might contain boronates in a mix of protonation states, whose average approximates to single deprotonation and such "mixed" salts are included in the term "acid salt"). Examples of acid salts are monosodium salts and hemicalcium salts.

α-Aminoboronic acid or Boro(aa) refers to an amino acid in which the $CO_2$ group has been replaced by $BO_2$.

The term "amino-group protecting moiety" refers to any group used to derivatise an amino group, especially an N-terminal amino group of a peptide or amino add. Such groups include, without limitation, alkyl, acyl, alkoxycarbonyl, aminocarbonyl, and sulfonyl moieties. However, the term "amino-group protecting moiety" is not intended to be limited to those particular protecting groups that are commonly employed in organic synthesis, nor is it intended to be limited to groups that are readily cleavable.

The phrase "pharmaceutically acceptable" is employed herein to refer to those compounds, materials, compositions, and/or dosage forms which are, within the scope of sound medical judgment, suitable for use in contact with the tissues of human beings or animals without excessive toxicity, irritation, allergic response, or other problem or complication, commensurate with a reasonable benefit/risk ratio.

The expression "thrombin inhibitor" refers to a product which, within the scope of sound pharmacological judgement, is potentially or actually pharmaceutically useful as an inhibitor of thrombin, and includes reference to substance which comprises a pharmaceutically active species and is described, promoted or authorised as a thrombin inhibitor. Such thrombin inhibitors may be selective, that is they are regarded, within the scope of sound pharmacological judgement, as selective towards thrombin in contrast to other proteases; the term "selective thrombin inhibitor" includes reference to substance which comprises a pharmaceutically active species and is described, promoted or authorised as a selective thrombin inhibitor.

The term "heteroaryl" refers to a ring system which has at least one (e.g. 1, 2 or 3) in-ring heteroatoms and has a conjugated in-ring double bond system. The term "heteroatom" includes oxygen, sulfur and nitrogen, of which sulfur is sometimes less preferred.

"Natural amino acid" means an L-amino acid (or residue thereof) selected from the following group of neutral (hydrophobic or polar), positively charged and negatively charged amino acids:

Hydrophobic Amino Acids
A=Ala=alanine
V=Val=valine
I=Ile=isoleucine
L=Leu=leucine
M=Met=methionine
F=Phe=phenylalanine
P=Pro=proline
W=Trp=tryptophan
Polar (Neutral or Uncharged) Amino Acids
N=Asn=asparagine
C=Cys=cysteine
Q=Gin=glutamine
G=Gly=glycine
S=Ser=serine
T=Thr=threonine
Y=Tyr=tyrosine
Positively Charged (Basic) Amino Acids
R=Arg=arginine
H=His histidine
K=Lys=lysine
Negatively Charged Amino Acids
D=Asp=aspartic acid
E=Glu=glutamic acid.
ACN=acetonitrile Amino acid=α-amino acid
Base addition salt=a salt which is prepared from addition of an inorganic base or an organic base to a free acid (in this case the boronic acid).
Cbz=benzyloxycarbonyl
Cha=cyclohexylalanine (a hydrophobic unnatural amino acid)
Charged (as applied to drugs or fragments of drug molecules, e.g. amino acid residues)=carrying a charge at physiological pH, as in the case of an amino, amidino or carboxy group
Dcha=dicyclohexylalanine (a hydrophobic unnatural amino acid)
Dpa=diphenylalanine (a hydrophobic unnatural amino acid)
Drug=a pharmaceutically useful substance, whether the active in vivo principle or a prodrug
i.v.=intravenous
Mpg=3-methoxypropylglycine (a hydrophobic unnatural amino acid)
Multivalent=valency of at least two, for example two or three
Neutral (as applied to drugs or fragments of drug molecules, e.g. amino acid residues)=uncharged=not carrying a charge at physiological pH
Pinac=Pinacol=2,3-dimethyl-2,3-butanediol
Pinanediol=2,3-pinanediol=2,6,6-trimethylbicyclo[3.1.1]heptane-2,3-diol
Pip=pipecolinic acid
s.c.=subcutaneous
Strong base=a base having a sufficiently high pKb to react with a boronic acid. Suitably such bases have a pKb of 7 or more, e.g. 7.5 or more, for example about 8 or more
THF=tetrahydrofuran
Thr=thrombin The Compounds The products of the disclosure comprise salts of boronic acids which have a neutral aminoboronic acid residue capable of binding to the thrombin Si subsite linked through a peptide linkage to a hydrophobic moiety capable of binding to the thrombin S2 and S3 subsites. The disclosure includes salts of acids of formula (I):

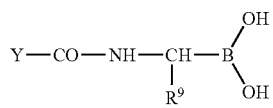

(I)

wherein

Y comprises a hydrophobic moiety which, together with the aminoboronic acid residue —NHCH($R^9$)—B(OH)$_2$, has affinity for the substrate binding site of thrombin; and $R^9$ is a straight chain alkyl group interrupted by one or more ether linkages and in which the total number of oxygen and carbon atoms is 3, 4, 5 or 6 (e.g. 5) or $R^9$ is —(CH$_2$)$_m$—W where m is from 2, 3, 4 or 5 (e.g. 4) and W is —OH or halogen (F, Cl, Br or I). As examples of straight chain alkyl interrupted by one or more ether linkages (—O—) may be mentioned alkoxyalkyl (one interruption) and alkoxyalkoxyalkyl (two interruptions). $R^9$ is an alkoxyalkyl group in one subset of compounds, e.g. alkoxyalkyl containing 4 carbon atoms.

Typically, YCO— comprises an amino acid residue (whether natural or unnatural) which binds to the S2 subsite of thrombin, the amino acid residue being N-terminally linked to a moiety which binds the S3 subsite of thrombin.

In one class of Formula (I) acids, YCO— is an optionally N-terminally protected dipeptide residue which binds to the S3 and S2 binding sites of thrombin and the peptide linkages in the acid are optionally and independently N-substituted by a $C_1$-$C_{13}$ hydrocarbyl group optionally containing in-chain and/or in-ring nitrogen, oxygen or sulfur and optionally substituted by a substituent selected from halo, hydroxy and trifluoromethyl. The N-terminal protecting group, when present, may be a group X as defined above (other than hydrogen). Normally, the acid contains no N-substituted peptide linkages; where there is an N-substituted peptide linkage, the substituent is often 1C to 6C hydrocarbyl, e.g. saturated hydrocarbyl; the N-substituent comprises a ring in some embodiments, e.g. cycloalkyl, and may be cyclopentyl, for example. One class of acids has an N-terminal protecting group (e.g. an X group) and unsubstituted peptide linkages.

Where YCO— is a dipeptide residue (whether or not N-terminally protected), the S3-binding amino acid residue may be of R configuration and/or the S2-binding residue may of S configuration. The fragment —NHCH($R^9$)—B(OH) may of R configuration. The disclosure is not restricted to chiral centres of these conformations, however.

In one class of compounds, the side chain of P3 (S3-binding) amino acid and/or the P2 (S2-binding) amino acid is a moiety other than hydrogen selected from a group of formula A or B:

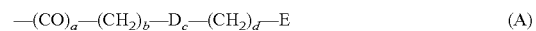

(A)

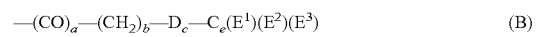

(B)

wherein a is 0 or 1;

e is 1;

b and d are independently 0 or an integer such that (b+d) is from 0 to 4 or, as the case may be, (b+e) is from 1 to 4;

c is 0 or 1;

D is O or S;

E is H, $C_1$-$C_6$ alkyl, or a saturated or unsaturated cyclic group which normally contains up to 14 members and particularly is a 5-6 membered ring (e.g. phenyl) or an 8-14 membered fused ring system (e.g. naphthyl), which alkyl or cyclic group is optionally substituted by up to 3 groups (e.g. 1 group) independently selected from $C_1$-$C_6$ trialkylsilyl, —CN, —$R^{13}$, —$R^{12}OR^{13}$, —$R^{12}COR^{13}$, —$R^{12}CO_2R^{13}$ and —$R^{12}O_2CR^{13}$, wherein $R^{12}$ is —(CH$_2$)$_f$— and $R^{13}$ is —(CH$_2$)gH or by a moiety whose non-hydrogen atoms consist of carbon atoms and in-ring heteroatoms and number from 5 to 14 and which contains a ring system (e.g. an aryl group) and optionally an alkyl and/or alkylene group, wherein f and g are each independently from 0 to 10, g particularly being at least 1 (although —OH may also be mentioned as a substituent), provided that (f+g) does not exceed 10, more particularly does not exceed 6 and most particularly is 1, 2, 3 or 4, and provided that there is only a single substituent if the substituent is a said moiety containing a ring system, or E is $C_1$-$C_6$ trialkylsilyl; and $E^1$, $E^2$ and $E^3$ are each independently selected from —$R^{15}$ and —J—$R^{15}$, where J is a 5-6 membered ring and $R^{15}$ is selected from $C_1$-$C_6$ trialkylsilyl, —CN, —$R^{13}$, —$R^{12}OR^{13}$, —$R^{12}COR^{13}$, —$R^{12}CO_2R^{13}$, —$R^{12}O_2CR^{13}$, and one or two halogens (e.g. in the latter case to form a —J—$R^{15}$ moiety which is dichlorophenyl), where $R^{12}$ and $R^{13}$ are, respectively, an $R^{12}$ moiety and an $R^{13}$ moiety as defined above (in some acids where $E^1$, $E^2$ and $E^3$ contain an $R^{13}$ group, g is 0 or 1);

in which moiety of Formula (A) or (B) any ring is carbocyclic or aromatic, or both, and any one or more hydrogen atoms bonded to a carbon atom is optionally replaced by halogen, especially F.

In certain examples, a is 0. If a is 1, c may be 0. In particular examples, (a+b+c+d) and (a+b+c+e) are no more than 4 and are more especially 1, 2 or 3. (a+b+c+d) may be 0.

Exemplary groups for E, $E^1$, $E^2$ and $E^3$ include aromatic rings such as phenyl, naphthyl, pyridyl, quinolinyl and furanyl, for example; non-aromatic unsaturated rings, for example cyclohexenyl; saturated rings such as cyclohexyl, for example. E may be a fused ring system containing both aromatic and non-aromatic rings, for example fluorenyl. One class of E, $E^1$, $E^2$ and $E^3$ groups are aromatic (including heteroaromatic) rings, especially 6-membered aromatic rings. In some compounds, $E^1$ is H whilst $E^2$ and $E^3$ are not H; in those compounds, examples of $E^2$ and $E^3$ groups are phenyl (substituted or unsubstituted) and $C_1$-$C_4$ alkyl, e.g. methyl.

In one class of embodiments, E contains a substituent which is $C_1$-$C_6$ alkyl, ($C_1$-$C_5$ alkyl)carbonyl, carboxy $C_1$-$C_5$ alkyl, aryl (including heteroaryl), especially 5-membered or preferably 6-membered aryl (e.g. phenyl or pyridyl), or arylalkyl (e.g. arylmethyl or arylethyl where aryl may be heterocyclic and is preferably 6-membered).

In another class of embodiments, E contains a substituent which is $OR^{13}$, wherein $R^{13}$ can be a 6-membered ring, which may be aromatic (e.g. phenyl) or is alkyl (e.g. methyl or ethyl) substituted by such a 6-membered ring.

A class of moieties of formula A or B are those in which E is a 6-membered aromatic ring optionally substituted, particularly at the 2-position or 4-position, by —$R^{13}$ or —$OR^{13}$.

The disclosure includes salts in which the P3 and/or P2 side chain comprises a cyclic group in which 1 or 2 hydrogens have been replaced by halogen, e.g. F or Cl.

The disclosure includes a class of salts in which the side chains of formula (A) or (B) are of the following formulae (C), (D) or (E):

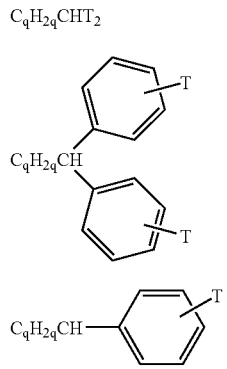

wherein q is from 0 to 5, e.g. is 0, 1 or 2, and each T is independently hydrogen, one or two halogens (e.g. F or Cl), —$SiMe_3$, —CN, —$R^{13}$, —$OR^{13}$, —$COR^{13}$, —$CO_2R^{13}$ or —$O_2CR^{13}$. In some embodiments of structures (D) and (E), T is at the 4-position of the phenyl group(s) and is —$R^{13}$, —$OR^{13}$, —$COR^{13}$, —$CO_2R^{13}$ or —$O_2CR^{13}$, and $R^{13}$ is $C_1$-$C_{10}$ alkyl and more particularly $C_1$-$C_6$ alkyl. In one sub-class, T is —$R^{13}$ or —$OR^{13}$, for example in which f and g are each independently 0, 1, 2 or 3; in some side chains groups of this sub-class, T is —$R^{12}OR^{13}$ and $R^{13}$ is H.

In one class of the moieties, the side chain is of formula (C) and each T is independently $R^{13}$ or $OR^{13}$ and $R^{13}$ is $C_1$-$C_4$ alkyl. In some of these compounds, $R^{13}$ is branched alkyl and in others it is straight chain. In some moieties, the number of carbon atoms is from 1 to 4.

In many dipeptide fragments YCO— (which dipeptides may be N-terminally protected or not), the P3 amino acid has a side chain of formula (A) or (B) as described above and the P2 residue is of an imino acid.

The disclosure therefore includes medicaments comprising salts, e.g. metal salts, of organoboronic acids which are thrombin inhibitors, particularly selective thrombin inhibitors, having a neutral P1 (S1-binding) moiety. For more information about moieties which bind to the S3, S2 and S1 sites of thrombin, see for example Tapparelli C et al, *Trends Pharmacol. Sci.* 14: 366-376, 1993; Sanderson P et al, *Current Medicinal Chemistry*, 5: 289-304, 1998; Rewinkel 3 et al, *Current Pharmaceutical Design*, 5:1043-1075, 1999; and Coburn C *Exp. Opin. Ther. Patents* 11(5): 721-738, 2001. The thrombin inhibitory salts of the disclosure are not limited to those having S3, S2 and S1 affinity groups described in the publications listed in the preceding sentence.

The boronic acids may have a Ki for thrombin of about 100 nM or less, e.g. about 20 nM or less.

A subset of the Formula (I) acids comprises the acids of Formula (III):

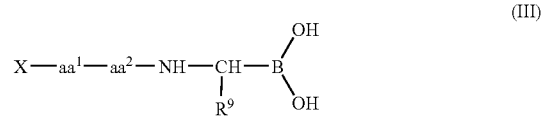

X is a moiety bonded to the N-terminal amino group and may be H to form $NH_2$. The identity of X is not critical but may be a particular X moiety described above. In one example there may be mentioned benzyloxycarbonyl.

In certain examples X is $R^6$—$(CH_2)_p$—C(O)—, $R^6$—$(CH_2)_p$—$S(O)_2$—, $R^6$—$(CH_2)$—NH—C(O)— or $R^6$—$(CH_2)_p$—O—C(O)— wherein p is 0, 1, 2, 3, 4, 5 or 6 (of which 0 and 1 are preferred) and $R^6$ is H or a 5 to 13-membered cyclic group optionally substituted by 1, 2 or 3 substituents selected from halogen, amino, nitro, hydroxy, a $C_5$-$C_6$ cyclic group, $C_1$-$C_4$ alkyl and $C_1$-$C_4$ alkyl containing, and/or linked to the 5 to 13-membered cyclic group through, an in-chain O, the aforesaid alkyl groups optionally being substituted by a substituent selected from halogen, amino, nitro, hydroxy and a $C_5$-$C_6$ cyclic group. More particularly X is $R^6$—$(CH_2)_p$—C(O)— or $R^6$—$(CH_2)_p$—O—C(O)— and p is 0 or 1. Said 5 to 13-membered cyclic group is often aromatic or heteroaromatic, for example is a 6-membered aromatic or heteroaromatic group. In many cases, the group is not substituted.

Exemplary X groups are (2-pyrazine) carbonyl, (2-pyrazine) sulfonyl and particularly benzyloxycarbonyl.

$aa^1$ is an amino acid residue having a hydrocarbyl side chain containing no more than 20 carbon atoms (e.g. up to 15 and optionally up to 13 C atoms) and comprising at least one cyclic group having up to 13 carbon atoms. In certain examples, the cyclic group(s) of aa¹ have/has 5 or 6 ring members. For instance, the cyclic group(s) of aa¹ may be aryl groups, particularly phenyl. Typically, there are one or two cyclic groups in the aa¹ side chain. Certain side chains comprise, or consist of, methyl substituted by one or two 5- or 6-membered rings.

More particularly, aa¹ is Phe, Dpa or a wholly or partially hydrogenated analogue thereof. The wholly hydrogenated analogues are Cha and Dcha.

aa² is an imino acid residue having from 4 to 6 ring members. Alternatively, aa² is Gly N-substituted by a $C_3$-$C_{13}$ hydrocarbyl group, e.g. a $C_3$-$C_8$ hydrocarbyl group comprising a $C_3$-$C_6$ hydrocarbyl ring; the hydrocarbyl group may be saturated, for example exemplary N-substituents are cyclopropyl, cyclobutyl, cyclopentyl and cyclohexyl. As a hydrocarbyl group containing one or more unsaturated bonds may be mentioned phenyl and methyl or ethyl substituted by phenyl, e.g. 2-phenylethyl, as well as β,β-dialkylphenylethyl.

An exemplary class of products comprises those in which aa² is a residue of an imino acid of formula (IV)

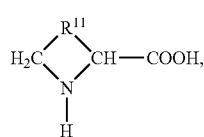

(IV)

where $R^{11}$ is —$CH_2$—, $CH_2$—$CH_2$—, —S—$CH_2$— or —$CH_2$—$CH_2$—$CH_2$—, which group when the ring is 5 or 6-membered is optionally substituted at one or more —$CH_2$— groups by from 1 to 3 $C_1$-$C_3$ alkyl groups, for example to form the $R^{11}$ group —S—$C(CH_3)_2$—. Of these imino acids, azetidine-2-carboxylic acid, especially (s)-azetidine-2-carboxylic acid, and more particularly proline are illustrative.

It will be appreciated from the above that a very preferred class of products consists of those in which aa¹-aa² is Phe-Pro. In another preferred class, aa¹-aa² is Dpa-Pro. In other products, aa¹-aa² is Cha-Pro or Dcha-Pro. Of course, also included are corresponding product classes in which Pro is replaced by (s)-azetidine-2-carboxylic acid.

$R^9$ is as defined previously and may be a moiety $R^1$ of the formula —$(CH_2)_s$—Z. Integer s is 2, 3 or 4 and W is —OH, —OMe, —OEt or halogen (F, Cl, I or, preferably, Br). Particularly illustrative Z groups are —OMe and —OEt, especially —OMe. In certain examples s is 3 for all Z groups and, indeed, for all compounds of the disclosure. Particular $R^1$ groups are 2-bromoethyl, 2-chloroethyl, 2-methoxyethyl, 4-bromobutyl, 4-chlorobutyl, 4-methoxybutyl and, especially, 3-bromopropyl, 3-chloropropyl and 3-methoxypropyl. Most preferably, $R^1$ is 3-methoxypropyl. 2-Ethoxyethyl is another preferred $R^1$ group.

Accordingly, a specific class of salts consists of those of acids of the formula X-Phe-Pro-Mpg-B(OH)$_2$, especially Cbz-Phe-Pro-Mpg-B(OH)$_2$; also included are analogues of these compounds in which Mpg is replaced by a residue with another of the $R^1$ groups and/or Phe is replaced by Dpa or another aa¹ residue.

The aa¹ moiety of the salt is preferably of (R)-configuration. The aa² moiety is preferably of (S)-configuration. Particularly preferred salts have aa¹ of (R)-configuration and aa² of (S)-configuration. The chiral centre —NH—CH ($R^1$)—B— is preferably of (R)-configuration. It is considered that commercial formulations will have the chiral centres in (R,S,R) arrangement, as for example in the case of salts of Cbz-Phe-Pro-BoroMpg-OH:

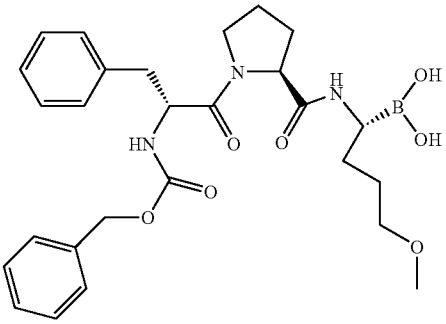

Cbz-(R)-Phe-(S)-Pro-(R)-boroMpg-OH

The disclosure includes salts of Cbz-(R)-Phe-(S)-Pro-(R)-boroMpg-OH (and of other compounds of the formula X-(R)-Phe-(S)-Pro-(R)-boroMpg-OH) which are at least 90% pure, e.g. at least 95% pure.

In broad terms, the salts described herein may be considered to correspond to reaction products of an organoboronic acid as described above with a strong base, e.g. a basic metal compound; the salts are however not limited to products resulting from such a reaction and may be obtained by alternative routes.

The salts are therefore obtainable by contacting an acid of formula (I) with a strong base. The disclosure thus contemplates products (compositions of matter) having the characteristics of a reaction product of an acid of formula (I) and a strong base. The base is pharmaceutically acceptable.

As suitable salts may be mentioned salts of metals, e.g. of monovalent or divalent metals, and stronger organic bases, for example:

1. Alkali metal salts;
2. Divalent, eg alkaline earth metal, salts;
3. Group III metals;
4. Salts of strongly basic organic nitrogen-containing compounds, including:
   4A. Salts of guanidines and their analogues;
   4B. Salts of strongly basic amine, examples of which include (i) aminosugars and (ii) other amines.

Of the above salts, particularly illustrative are alkali metals, especially Na and Li. Also illustrative are aminosugars.

Specific salts are of the acid boronate though in practice the acid salts may contain a very small proportion of the doubly deprotonated boronate. The term "acid boronate" refers to trigonal —B(OH)$_2$ groups in which one of the B—OH groups is deprotonated as well as to corresponding tetrahedral groups in equilibrium therewith. Acid boronates have a stoichiometry consistent with single deprotonation.

The disclosure includes therefore products (compositions of matter) which comprise salts which may be represented by formula (V):

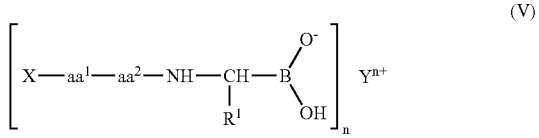

(V)

where $Y^{n+}$ is a pharmaceutically acceptable cation obtainable from a strong base, and $aa^1$, $aa^2$, X and $R^1$ are as defined above. Also included are products in which $R^1$ is replaced by another $R^9$ group.

One class of salts have a solubility of about 10 mM or more, e.g. of at least about 20 mM, when their solubility is determined as described in the examples at a dissolution of 25 mg/ml. More particularly yet they have a solubility of least 50 mM when their solubility is determined as described in the examples at a dissolution of 50 mg/ml.

The disclosure includes salts of boronic acids (I) having an observed stoichiometry consistent with the salt being of (being representable by) the formula "(boronate$^-$)$_n$ cation$^{n+}$". One class of such salts are represented by the formula:

[Cbz-(R)-Phe-(S)-Pro-(R)-Mpg-B(OH)(O$^-$)]M$^+$ where M$^+$ represents a monovalent cation, especially an alkali metal cation. It will be understood that the above representation is a notional representation of a product whose observed stoichiometry is unlikely to be literally and exactly 1:1. In any event, a particular salt is Cbz-(R)-Phe-(S)-Pro-(R)-Mpg-B(OH)$_2$ monosodium salt (TGN 255). In the above formula, the trigonally-represented boronate represents, as always, boronates which are trigonal, tetrahedral or mixed trigonal/tetrahedral.

Particularly exemplary are products which comprise:
(i) species selected from (a) acids of formula (VIII): X-(R)-Phe-(S)-Pro-(R)-Mpg-B(OH)$_2$ where X is H or an amino-protecting group, especially Cbz, (b) boronate anions thereof, and (c) any equilibrium form of the a foregoing (e.g. an anhydride); and
(ii) ions having a valency n in combination with said species, the species and said ions having an observed stoichiometry consistent with a notional species:ion stoichiometry of n:1. In one class of salts, n is 1.

Considering the counter-ions in turn:

1. Monovalent Metal, Especially Alkali Metal Salts

Suitable alkali metals include lithium, sodium and potassium. All of these are remarkably soluble. Lithium and sodium are illustrative because of their high solubility. The lithium and particularly sodium salts are of surprisingly high solubility in relation to potassium amongst others. Sodium is most used in many instances. Salts containing mixtures of alkali metals are contemplated by the disclosure.

The disclosure includes products comprising salts of the formula (VI)

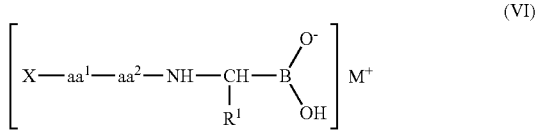

(VI)

where M$^+$ is an alkali metal ion and $aa^1$, $aa^2$, X and $R^1$ are as defined above, as well as salts in which both hydroxy groups of the boronate group are in salt form (preferably with another identical M$^+$ group) and mixtures of such salts. Included also are products wherein $R^1$ is replaced by another $R^9$ group.

2. Divalent, e.g. Alkaline Earth Metal (Group II Metal) Salts

One example of a divalent metal is calcium. Another suitable divalent metal is magnesium. Also contemplated is zinc. The divalent metals are usually used in a boronic acid:metal ratio of substantially 2:1, in order to achieve the preferred monovalent boronate moiety. Salts containing mixtures of divalent metals, e.g. mixtures of alkaline earth metals, are also contemplated.

Further disclosed are products (compositions of matter) which comprise salts which may be represented by the formula (VII):

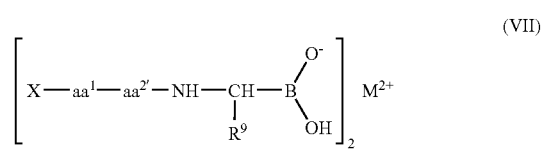

(VII)

where M$^{2+}$ is a divalent metal cation, e.g. an alkaline earth metal or zinc cation, and $aa^1$, $aa^{2'}$, X and $R^9$ are as defined above, as well as salts in which both hydroxy groups of the boronate group are deprotonated and mixtures of such salts. As previously indicated, the boronate may comprise a tetrahedral species.

3. Group III Metals

Suitable Group III metals include aluminium and gallium. Salts containing mixtures of Group III metals are also contemplated.

The disclosure includes products comprising salts of the formula (VIII):

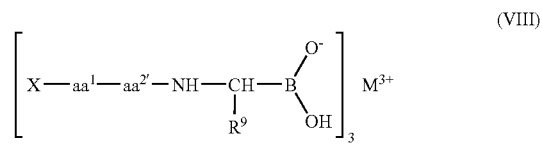

(VIII)

where M$^{3+}$ is a Group III metal ion and $aa^1$, $aa^{2'}$, X and $R^9$ are as defined above, as well as salts in which both hydroxy groups of the boronate group are in salt form and mixtures of such salts. As previously indicated, the boronate may comprise a tetrahedral species.

4. Strongly Basic Organic Nitrogen-containing Compounds

The disclosure includes products obtainable by (having the characteristics of a product obtained by) reaction of a peptide boronic acid as defined above and a strong organic base. Two illustrative classes of organic base are described in sections 4A and 4B below. Particularly preferred are acid salts (in which one of the two boronic —OH groups is deprotonated). Most commonly, the salts contain a single type of organic counter-ion (disregarding trace contaminants) but the disclosure contemplates salts containing mixtures of organic counter-ions; in one sub-class, the different counter-ions all fall within the section 4A family described below or, as the case may be, in the section 4B family below;

in another subclass, the salts comprise a mixture of organic counter-ions which are not all from the same family (4A or 4B).

Suitable organic bases include those with a pKb of 7 or more, e.g. 7.5 or more, for example in the region of 8 or more. Bases which are less lipophilic [e.g. have at least one polar functional group (e.g. 1, 2 or 3 such groups) for example hydroxy] are favoured; thus aminosugars are one favoured class of base.

4A. Guanidines and Their Analogues

The guanidino compound (guanidine) may in principle be any soluble and pharmaceutically acceptable compound having a guanidino or a substituted guanidino group, or a substituted or unsubstituted guanidine analogue. Suitable substituents include aryl (e.g. phenyl), alkyl or alkyl interrupted by an ether or thioether linkage and, in any event, typically contain from 1 to 6 and especially 1, 2, 3, or 4 carbon atoms, as in the case of methyl or ethyl. The guanidino group may have 1, 2, 3 or 4 substituent groups but more usually has 1 or 2 substituent groups, for instance on a terminal nitrogen. One class of guanidines is monoalkylated; another class is dialkylated. As guanidine analogues may be mentioned thioguanidines and 2-amino pyridines. Compounds having unsubstituted guanidino groups, for example guanidine and arginine, form one particular class.

Salts containing mixtures of guanidines are contemplated by the disclosure.

A particular guanidino compound is L-arginine or an L-arginine analogue, for example D-arginine, or the D- or, preferably, L-isomers of homoarginine or agmatine [(4-aminobutyl) guanidine]. Less preferred arginine analogues are NG-nitro-L-arginine methyl ester, for example, and constrained guanidine analogues, particularly 2-amino pyrimidines, for example 2,6-quinazolinediamines such as 5,6,7,8-tetrahydro-2,6-quinazolinediamine, for example. The guanidino compound may also be a peptide, for example a dipeptide, containing arginine; one such dipeptide is L-tyrosyl-L-arginine.

Some particular guanidino compounds are compounds of formula (VII):

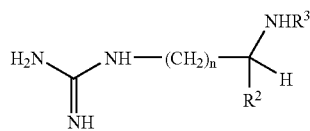
(VII)

where n is from 1 to 6 and for example at least 2, e.g. 3 or more, and in many instances no more than 5. Most particularly, n is 3, 4 or 5. $R^2$ is H or carboxylate or derivatised carboxylate, for example to form an ester (e.g. a $C_1$-$C_4$ alkyl ester) or amide. $R^3$ is H, $C_1$-$C_4$ alkyl or a residue of a natural or unnatural amino acid (e.g. tyrosine). The compounds of formula (IV) are usually of L-configuration. The compounds of formula (IV) are arginine (n=3; $R^2$=carboxyl; $R^3$=H) and arginine derivatives or analogues.

The disclosure includes products comprising salts of the formula (IX)

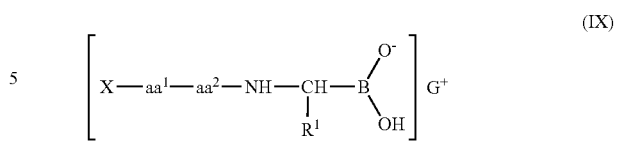
(IX)

where $aa^1$, $aa^2$, X and $R^1$ are as defined previously and $G^+$ is the protonated form of a pharmaceutically acceptable organic compound comprising a guanidino group or an analogue thereof, as well as salts in which both hydroxy groups of the boronate group are in salt form (preferably with another identical $G^+$ group) and mixtures of such salts. Also included are products wherein $R^1$ is replaced by another $R^9$ group.

4B. Strongly Basic Amines

The disclosure includes products obtainable by (having the characteristics of a product obtained by) reaction of a peptide boronic acid as defined above and a strong organic base which is an amine. The amine may in principle be any soluble and pharmaceutically acceptable amine.

It is envisaged that a desirable class of amine includes those having polar functional groups in addition to a single amine group, as such compounds will be more hydrophilic and thus more soluble than others. In certain salts, the or each additional functional group is hydroxy. Some amines have 1, 2, 3, 4, 5 or 6 additional functional groups, especially hydroxy groups. In one illustrative class of amines the ratio of (amino plus hydroxy groups):carbon atoms is from 1:2 to 1:1, the latter ratio being particularly preferred. These amines with one or more additional polar functional groups may be a hydrocarbon, especially an alkane, substituted by the amino group and the additional polar group(s). The amino group may be substituted or unsubstituted and, excluding amino substituents, the polar base may contain, for example, up to 10 carbon atoms; usually there are no less than three such carbon atoms, e.g. 4, 5 or 6. Aminosugars are included in this category of polar bases.

The disclosure includes products comprising salts of the formula (X)

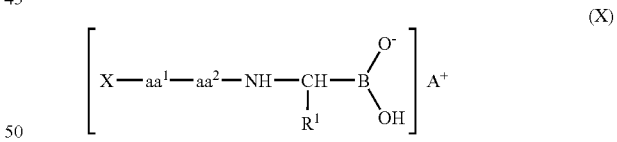
(X)

where $aa^1$, $aa^2$, X and $R^1$ are as defined previously and $A^+$ is the protonated form of a pharmaceutically acceptable amine, as well as salts in which both hydroxy groups of the boronate group are in salt form (preferably with another identical $A^+$ group) and mixtures of such salts. In one class of such products, $A^+$ is the protonated form of an amine described in section 4B(i) below; in another class $A^+$ is the protonated form of an amine described in 4B(ii) below. Also included are products in which $R^1$ is replaced by another $R^9$ group.

Two illustrative classes of amine base are described in sections 4B(i) and 4B(ii) below. Particularly preferred are acid salts (in which one of the two boronic —OH groups is deprotonated). Most commonly, the salts contain a single type of amine counter-ion (disregarding trace contaminants)

but the disclosure contemplates salts containing mixtures of amine counter-ions; in one sub-class, the different counter-ions all fall within the sub-section 4B(i) family described below or, as the case may be, in the sub-section 4B(ii) family below; in another subclass, the salts comprise a mixture of organic counter-ions which are not all from the same family (4B(i) or 4B(ii)).

4B(i) Aminosugars

The identity of the aminosugar is not critical. Preferred aminosugars include ring-opened sugars, especially glucamines. Cyclic aminosugars are also envisaged as useful. One class of the aminosugars is N-unsubstituted and another, preferred, class is N-substituted by one or two N-substituents (e.g. one). Suitable substituents are hydrocarbyl groups, for example and without limitation containing from 1 to 12 carbon atoms; the substituents may comprise alkyl or aryl moieties or both. Exemplary substituents are $C_1$, $C_2$, $C_3$, $C_4$, $C_5$, $C_6$, $C_7$ and $C_8$ alkyl groups, in particular methyl and ethyl, of which methyl is illustrative. Data indicate that aminosugars, especially N-methyl-D-glucamine, are of surprisingly high solubility.

A most preferred aminosugar is N-methyl-D-glucamine:

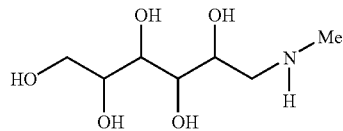

4B(ii) Other Amines

Other suitable amines include amino acids (whether naturally occurring or not) whose side chain is substituted by an amino group, especially lysine.

Some amines are compounds of formula (XI):

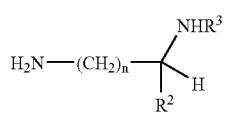

(XI)

where n, $R^2$ and $R^3$ are as defined in relation to formula (IV). The compounds of formula (VI) are usually of L-configuration. The compounds of formula (VI) are lysine (n=4; $R^2$=carboxyl; $R^3$=H) and lysine derivatives or analogues. A most preferred amine is L-lysine.

Other suitable amines are nitrogen-containing heterocycles. At least usually, such heterocyclic compounds are alicyclic; one class of the heterocyclic compounds is N-substituted and another, preferred, class is N-unsubstituted. The heterocycles may contain 6 ring-forming atoms, as in the cases of piperidine, piperazine and morpholine. One class of amines includes N-containing heterocycles substituted by polar substituents, especially hydroxy, e.g. 1, 2 or 3 times.

The disclosure therefore includes amines other than aminosugars which have one or more (e.g. 1, 2, 3, 4, 5 or 6) polar substituents, especially hydroxy, in addition to one amine group. Such compounds may have a ratio of (amino plus hydroxy groups):carbon atoms of 1:2 to 1:1, the latter ratio being particularly preferred.

The disclosure includes mixed salts, i.e. salts containing a mixture of boropeptide moieties and/or counterions but single salts are preferred.

The salts in solid form may contain a solvent, e.g. water. There are included a class of products in which the salts are essentially anhydrous. Also included is a class in which the salts are hydrates.

Use of the Products of the Disclosure

The salts of the disclosure are thrombin inhibitors. They are therefore useful for inhibiting thrombin. There are therefore provided compounds which have potential for controlling haemostasis and especially for inhibiting coagulation, for example in the treatment or prevention of secondary events after myocardial infarction. The medical use of the compounds may be prophylactic (including to treat thrombosis as well as to prevent occurrence of thrombosis) as well as therapeutic (including to prevent re-occurrence of thrombosis or secondary thrombotic events).

The salts may be employed when an anti-thrombogenic agent is needed. Further, it has been found that the salts, including those of boronic acids of Formula (III), are beneficial in that the class is useful for treating arterial thrombosis by therapy or prophylaxis. The disclosed salts are thus indicated in the treatment or prophylaxis of thrombosis and hypercoagulability in blood and tissues of animals including man. The term "thrombosis" includes inter alia atrophic thrombosis, arterial thrombosis, cardiac thrombosis, coronary thrombosis, creeping thrombosis, infective thrombosis, mesenteric thrombosis, placental thrombosis, propagating thrombosis, traumatic thrombosis and venous thrombosis.

It is known that hypercoagulability may lead to thromboembolic diseases.

Examples of venous thromboembolism which may be treated or prevented with compounds of the disclosure include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the disclosure are useful for maintaining patency of indwelling catheters.

Examples of cardiogenic thromboembolism which may be treated or prevented with compounds of the disclosure include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of conditions involving arterial thrombosis include unstable angina (severe constrictive pain in chest of coronary origin), myocardial infarction (heart muscle cell death resulting from insufficient blood supply), ischemic heart disease (local ischemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterio-venous (mixed) thrombosis, anti-thrombotic compounds of the disclosure are useful for maintaining patency in arteriovenous shunts.

Other conditions associated with hypercoagulability and thromboembolic diseases which may be mentioned inherited or acquired deficiencies in heparin cofactor II, circulating antiphospholipid antibodies (Lupus anticoagulant), homocysteinemia, heparin induced thrombocytopenia and defects in fibrinolysis.

Particular uses which may be mentioned include the therapeutic and/or prophylactic treatment of venous thrombosis and pulmonary embolism. Preferred indications envisaged for the products of the disclosure (notably the salts of TRI 50c) include:

- Prevention of venous thromboembolic events (e.g. deep vein thrombosis and/or pulmonary embolism). Examples include patients undergoing orthopaedic surgery such as total hip replacement, total knee replacement, major hip or knee surgery; patients undergoing general surgery at high risk for thrombosis, such as abdominal or pelvic surgery for cancer; and in patients bedridden for more than 3 days and with acute cardiac failure, acute respiratory failure, infection.
- Prevention of thrombosis in the haemodialysis circuit in patients, in patients with end stage renal disease.
- Prevention of cardiovascular events (death, myocardial infarction, etc) in patients with end stage renal disease, whether or not requiring haemodialysis sessions.
- Prevention of venous thromboembolic events in patients receiving chemotherapy through an indwelling catheter.
- Prevention of thromboembolic events in patients undergoing lower limb arterial reconstructive procedures (bypass, endarteriectomy, transluminal angioplasty, etc).
- Treatment of venous thromboembolic events.
- Prevention of cardiovascular events in acute coronary syndromes (e.g. unstable angina, non Q wave myocardial ischaemia/infarction), in combination with another cardiovascular agent, for example aspirin (acetylsalicylic acid; aspirin is a registered trade mark in Germany), thrombolytics (see below for examples), anti-platelet agents (see below for examples).
- Treatment of patients with acute myocardial infarction in combination with acetylsalicylic acid, thrombolytics (see below for examples).

The thrombin inhibitors of the disclosure are thus indicated both in the therapeutic and/or prophylactic treatment of all the aforesaid disorders.

In one method, the products of the disclosure are used for the treatment of patients by haemodialysis, by providing the product in the dialysis solution, as described in relation to other thrombin inhibitors in WO 00/41715. The disclosure therefore includes dialysing solutions and dialysing concentrates which comprise a product of the disclosure, as well as a method of treatment by dialysis of a patient in need of such treatment, which method comprises the use of a dialysing solution including a low molecular weight thrombin inhibitor. Also included is the use of an anti-thrombotic product of the disclosure for the manufacture of a medicament for the treatment by dialysis of a patient, in which the anti-thrombotic product of the disclosure is provided in the. dialysing solution.

In another method, the products of the disclosure are used to combat undesirable cell proliferation, as described in relation to other thrombin inhibitors in WO 01/41796. The undesirable cell proliferation is typically undesirable hyperplastic cell proliferation, for example proliferation of smooth muscle cells, especially vascular smooth muscle cells. The products of the disclosure particularly find application in the treatment of intimal hyperplasia, one component of which is proliferation of smooth muscle cells. Restenosis can be considered to be due to neointimal hyperplasia; accordingly intimal hyperplasia in the context of the disclosure includes restenosis.

The products of the disclosure are also contemplated for the treatment of ischemic disorders. More particularly, they may be used in the treatment (whether therapeutic or prophylactic) of an ischemic disorder in a patient having, or at risk of, non-valvular atrial fibrillation (NVAF) as described in relation to other thrombin inhibitors in WO 02/36157. Ischemic disorders are conditions whose results include a restriction in blood flow to a part of the body. The term will be understood to include thrombosis and hypercoagulability in blood, tissues and/or organs. Particular uses that may be mentioned include the prevention and/or treatment of ischemic heart disease, myocardial infarction, systemic embolic events in e.g. the kidneys or spleen, and more particularly of cerebral ischemia, including cerebral thrombosis, cerebral embolism and/or cerebral ischemia associated with non-cerebral thrombosis or embolism (in other words the treatment (whether therapeutic or prophylactic) of thrombotic or ischemic stroke and of transient ischemic attack), particularly in patients with, or at risk of, NVAF.

The products of the disclosure are also contemplated for the treatment of rheumatic/arthritic disorders, as described in relation to other thrombin inhibitors in WO 03/007984. Thus, the products of the disclosure may be used in the treatment of chronic arthritis, rheumatoid arthritis, osteoarthritis or ankylosing spondylitis Moreover, the products of the disclosure are expected to have utility in prophylaxis of re-occlusion (i.e. thrombosis) after thrombolysis, percutaneous trans-luminal angioplasty (PTA) and coronary bypass operations; the prevention of re-thrombosis after microsurgery and vascular surgery in general. Further indications include the therapeutic and/or prophylactic treatment of disseminated intravascular coagulation caused by bacteria, multiple trauma, intoxication or any other mechanism; anticoagulant treatment when blood is in contact with foreign surfaces in the body such as vascular grafts, vascular stents, vascular catheters, mechanical and biological prosthetic valves or any other medical device; and anticoagulant treatment when blood is in contact with medical devices outside the body such as during cardiovascular surgery using a heart-lung machine or in haemodialysis.

The products of the disclosure are further indicated in the treatment of conditions where there is an undesirable excess of thrombin without signs of hypercoagulability, for example in neurodegenerative diseases such as Alzheimer's disease. In addition to its effects on the coagulation process, thrombin is known to activate a large number of cells (such as neutrophils, fibroblasts, endothelial cells and smooth muscle cells). Therefore, the compounds of the disclosure may also be useful for the therapeutic and/or prophylactic treatment of idiopathic and adult respiratory distress syndrome, pulmonary fibrosis following treatment with radiation or chemotherapy, septic shock, septicaemia, inflammatory responses, which include, but are not limited to, edema, acute or chronic atherosclerosis such as coronary arterial disease, cerebral arterial disease, peripheral arterial disease, reperfusion damage, and restenosis after percutaneous trans-luminal angioplasty (PTA).

The salts may also be useful in the treatment of pancreatitis.

The salts described herein are further considered to be useful for inhibiting platelet procoagulant activity. The disclosure provides a method for inhibiting platelet pro-coagulant activity by administering a salt of a boronic acid described herein to a mammal at risk of, or suffering from, arterial thrombosis, particularly a human patient. Also provided is the use of such salts for the manufacture of medicaments for inhibiting platelet procoagulant activity.

The use of products of the disclosure as inhibitors of platelet pro-coagulant activity is predicated on the observation that the boronic acids described herein are indicated to be effective at inhibiting arterial thrombosis as well as venous thrombosis.

Indications involving arterial thrombosis include acute coronary syndromes (especially myocardial infarction and unstable angina), cerebrovascular thrombosis and peripheral arterial occlusion and arterial thrombosis occurring as a result of atrial fibrillation, valvular heart disease, artenio-venous shunts, indwelling catheters or coronary stents. Accordingly, in another aspect there is provided a method of treating a disease or condition selected from this group of indications, comprising administering to a mammal, especially a human patient, a salt of the disclosure. The disclosure includes products for use in an arterial environment, e.g. a coronary stent or other arterial implant, having a coating which comprises a salt according to the disclosure.

The salts of the disclosure may be used prophylactically to treat an individual believed to be at risk of suffering from arterial thrombosis or a condition or disease involving arterial thrombosis or therapeutically (including to prevent re-occurrence of thrombosis or secondary thrombotic events).

There is therefore included the use of selective thrombin inhibitors (organoboronic acid salts) described herein for treatment of the above disorders by prophylaxis or therapy as well as their use in pharmaceutical formulations and the manufacture of pharmaceutical formulations.

Administration and Pharmaceutical Formulations

The salts may be administered to a host, for example, in the case where the drug has anti-thrombogenic activity, to obtain an anti-thrombogenic effect. In the case of larger animals, such as humans, the compounds may be administered alone or in combination with pharmaceutically acceptable diluents, excipients or carriers. The term "pharmaceutically acceptable" includes acceptability for both human and veterinary purposes, of which acceptability for human pharmaceutical use is preferred.

The salts of the disclosure may be combined and/or co-administered with any cardiovascular treatment agent. There are large numbers of cardiovascular treatment agents available in commercial use, in clinical evaluation and in pre-clinical development, which could be selected for use with a product of the disclosure for the prevention of cardiovascular disorders by combination drug therapy. Such agent can be one or more agents selected from, but not limited to several major categories, namely, a lipid-lowering drug, including an IBAT (ileal $Na^+$/bile acid cotransporter) inhibitor, a fibrate, niacin, a statin, a CETP (cholesteryl ester transfer protein) inhibitor, and a bile acid sequestrant, an anti-oxidant, including vitamin E and probucol, a IIb/IIIa antagonist (e.g. abciximab, eptifibatide, tirofiban), an aldosterone inhibitor (e.g. spirolactone and epoxymexrenone), an adenosine A2 receptor antagonist (e.g. losartan), an adenosine A3 receptor agonist, a beta-blocker, acetylsalicylic acid, a loop diuretic and an ACE (angiotensin converting enzyme) inhibitor.

The salts of the disclosure may be combined and/or co-administered with any antithrombotic agent with a different mechanism of action, such as the antiplatelet agents acetylsalicylic acid, ticlopidine, clopidogrel, thromboxane receptor and/or synthetase inhibitors, prostacyclin mimetics and phosphodiesterase inhibitors and ADP-receptor ($P_2$ T) antagonists.

The products of the disclosure may further be combined and/or co-administered with thrombolytics such as tissue plasminogen activator (natural, recombinant or modified), streptokinase, urokinase, prourokinase, anisoylated plasminogen-streptokinase activator complex (APSAC), animal salivary gland plasminogen activators, and the like, in the treatment of thrombotic diseases, in particular myocardial infarction.

The salts of the disclosure may be combined and/or co-administered with a cardioprotectant, for example an adenosine A1 or A3 receptor agonist.

There is also provided a method for treating an inflammatory disease in a patient that comprises treating the patient with a product of the disclosure and an NSAID, e.g., a COX-2 inhibitor. Such diseases include but are not limited to nephritis, systemic lupus, erythematosus, rheumatoid arthritis, glomerulonephritis, vasculitis and sarcoidosis. Accordingly, the anti-thrombotic salts of the disclosure may be combined and/or co-administered with an NSAID.

Typically, therefore, the salts described herein may be administered to a host to obtain a thrombin-inhibitory effect, or in any other thrombin-inhibitory or anti-thrombotic context mentioned herein.

Actual dosage levels of active ingredients in the pharmaceutical compositions of this disclosure may be varied so as to obtain an amount of the active compound(s) that is effective to achieve the desired therapeutic response for a particular patient, composition, and mode of administration (referred to herein as a "therapeutically effective amount"). The selected dosage level will depend upon the activity of the particular compound, the severity of the condition being treated and the condition and prior medical history of the patient being treated. However, it is within the skill of the art to start doses of the compound at levels lower than required for to achieve the desired therapeutic effect and to gradually increase the dosage until the desired effect is achieved.

According to a further aspect there is provided a parenteral formulation including a salt as described herein. The formulation may consist of the salt alone or it may contain additional components, in particular the salt may be in combination with a pharmaceutically acceptable diluent, excipient or carrier, for example a tonicity agent for the purpose of making the formulation substantially isotonic with the body of the subject to receive the formulation, e.g. with human plasma. The formulation may be in ready-to-use form or in a form requiring reconstitution prior to administration.

It is currently contemplated that, in the case of parenteral administration, for example i.v. administration, of salts of TRI 50c, the salts might for instance be administered in an amount of from 0.5 to 2.5 mg/Kg e.g. over a maximum period of 72 hours, calculated as TRI 50c. Other salts might be administered in equivalent molar amounts. The disclosure is not limited to administration in such quantities or regimens and includes dosages and regimens outside those described in the previous sentence.

Parenteral preparations can be administered by one or more routes, such as intravenous, subcutaneous, intradermal and infusion; a particular example is intravenous. A formulation disclosed herein may be administered using a syringe, injector, plunger for solid formulations, pump, or any other device recognized in the art for parenteral administration.

Liquid dosage forms for parenteral administration may include solutions, suspensions, liposome formulations, or emulsions in oily or aqueous vehicles. In addition to the active compounds, the liquid dosage forms may contain other compounds. Tonicity agents (for the purpose of making the the formulations substantially isotonic with the subject's body, e.g. with human plasma) such as, for instance, sodium chloride, sodium sulfate, dextrose, mannitol and/or glycerol may be optionally added to the parenteral formulation. A pharmaceutically acceptable buffer may be added to control pH. Thickening or viscosity agents, for instance well known cellulose derivatives (e.g. methylcellulose, carboxymethylcellulose, hydroxyethylcellulose and hydroxypropylmethylcellulose), gelatin and/or acacia, may optionally be added to the parenteral formulation.

Solid dosage forms for parenteral administration may encompass solid and semi-solid forms and may include pellets, powders, granules, patches, and gels. In such solid dosage forms, the active compound is typically mixed with at least one inert, pharmaceutically acceptable excipient or carrier. The disclosed salts may be presented as solids in finely divided solid form, for example they may be milled or micronised.

The formulations may also include antioxidants and/or preservatives. As antioxidants may be mentioned thiol derivatives (e.g. thioglycerol, cysteine, acetylcysteine, cystine, dithioerythreitol, dithiothreitol, gluthathione), tocopherols, butylated hydroxyanisole, butylated hydroxytoluene, sulfurous acid salts (e.g. sodium sulfate, sodium bisulfite, acetone sodium bisulfite, sodium metabisulfite, sodium sulfite, sodium formaldehyde sulfoxylate, sodium thiosulfate) and nordihydroguaiareticacid. Suitable preservatives may for instance be phenol, chlorobutanol, benzylalcohol, methyl paraben, propyl paraben, benzalkonium chloride and cetylpyridinium chloride.

The parenteral formulations may be prepared as large volume parenterals (LVPs), e.g. larger than 100 ml, more particularly about 250 ml, of a liquid formulation of the active compound. Examples of LVPs are infusion bags. The parenteral formulations may alternatively be prepared as small volume parenterals (SVPs), e.g. about 100 ml or less of a liquid formulation of the active compound. Examples of SVPs are vials with solution, vials for reconstitution, pre-filled syringes for injection and dual chamber syringe devices.

The formulations of the disclosure include those in which the salt is an alkali metal salt, for example a lithium, sodium or potassium salt, of which sodium salts may be mentioned as particular salts. Another class of formulations contains aminosugar salts of the disclosed boronic acids, for example N-methyl-D-glucamine salts. The salts mentioned in this paragraph may be administered as solutions in water, typically containing one or more additives, for example isotonicity agent(s) and/or antioxidant(s). A suitable way to store the salts is in solid form, for example as dry powder, and to make them up into solutions for administration prior to administration.

One class of formulations disclosed herein is intravenous formulations. For intravenously administered formulations, the active compound or compounds can be present at varying concentrations, with a carrier acceptable for parenteral preparations making up the remainder. Particularly, the carrier is water, particularly pyrogen free water, or is aqueous based. Particularly, the carrier for such parenteral preparations is an aqueous solution comprising a tonicity agent, for example a sodium chloride solution.

By "aqueous based" is meant that formulation comprises a solvent which consists of water or of water and water-miscible organic solvent or solvents; as well as containing a salt of disclosure in dissolved form, the solvent may have dissolved therein one or more other substances, for example an antioxidant and/or an isotonicity agent. As organic cosolvents may be mentioned those water-miscible solvents commonly used in the art, for example propyleneglycol, polyethyleneglycol 300, polyethyleneglycol 400 and ethanol. Preferably, organic co-solvents are only used in cases where the active agent is not sufficiently soluble in water for a therapeutically effective amount to be provided in a single dosage form. As previously indicated, the disclosure includes formulations of alkali metal salts of the disclosed boronic acids, e.g. TRI 50c, having a solvent which consists of water.

The solubility of the active compound in the present formulations may be such that the turbidity of the formulation is lower than 50 NTU, e.g. lower than 20 NTU such as lower than 10 NTU. It is desirable that parenteral formulations are administered at or near physiological pH. It is believed that administration in a formulation at a high pH (i.e., greater than 8) or at a low pH (i.e., less than 5) is undesirable. In particular, it is contemplated that the formulations would be administered at a pH of between 6.0 and 7.0 such as a pH of 6.5.

The parenteral formulation may be purged of air when being packaged. The parenteral formulation may be packaged in a sterile container, e.g. vial, as a solution, suspension, gel, emulsion, solid or a powder. Such formulations may be stored either in ready-to-use form or in a form requiring reconstitution prior to administration.

Parenteral formulations according to the disclosure may be packaged in containers. Containers may be chosen which are made of material which is non-reactive or substantially non-reactive with the parenteral formulation. Glass containers or plastics containers, e.g. plastics infusion bags, may be used. A concern of container systems is the protection they afford a solution against UV degradation. If desired, amber glass employing iron oxide or an opaque cover fitted over the container may afford the appropriate UV protection.

Plastics containers such as plastics infusion bags are advantageous in that they are relatively light weight and non-breakable and thus more easily stored. This is particularly the case for Large Volume parenterals.

The intravenous preparations may be prepared by combining the active compound or compounds with the carrier. After the formulation is mixed, it may be sterilized, for example using known methods. Once the formulation has been sterilized, it is ready to be administered or packaged, particularly in dark packaging (e.g. bottles or plastics packaging), for storage. It is envisaged, however, that the disclosed salts might not be stored in solution but as dry solids, particularly a finely divided form such as, for example, a lyophilisate, in order to prolong shelf life; this would of course apply to other parenteral formulations, not only intravenous ones.

The intravenous preparations may take the form of large volume parenterals or of small volume parenterals, as decribed above.

In a specific embodiment, the present disclosure is directed to products, particularly kits, for producing a single-dose administration unit. The products (kits) may each contain both a first container having the active compound (optionally combined with additives, for example anti-oxidant, preservative and, in some instances, tonicity agent) and a second container having the carrier/diluent (for example water, optionally containing one or more additives, for example tonicity agent). As examples of such products may be mentioned single and multi-chambered (e.g. dual-chamber) pre-filled syringes; exemplary pre-filled syringes are available from Vetter GmbH, Ravensburg, Germany. Such dual chamber syringes or binary syringes will have in one chamber a dry preparation including or consisting of the active compound and in another chamber a suitable carrier or diluent such as described herein. The two chambers are joined in such a way that the solid and the liquid mix to form the final solution.

One class of formulations disclosed herein comprises subcutaneous or intradermal formulations (for example formulations for injection) in which the active salt (or active agent combination) is formulated into a parenteral preparation that can be injected subcutaneously or intradermally. The formulation for administration will comprise the active salt and a liquid carrier.

The carrier utilized in a parenteral preparation that will be injected subcutaneously or intradermally may be an aqueous carrier (for example water, typically containing an additive e.g. an antioxidant and/or an isotonicity agent) or a non-aqueous carrier (again one or more additives may be incorporated). As a non-aqueous carrier for such parenteral preparations may be mentioned highly purified olive oil.

The active compound and the carrier are typically combined, for example in a mixer. After the formulation is mixed, it is preferably sterilized, such as with U.V. radiation. Once the formulation has been sterilized, it is ready to be injected or packaged for storage. It is envisaged, however, that the disclosed salts will not be stored in liquid formulation but as dry solids, in order to prolong shelf life.

For making subcutaneous implants, the active salt may suitably be formulated together with one or more polymers that are gradually eroded or degraded when in use, e.g. silicone polymers, ethylene vinylacetate, polyethylene or polypropylene.

Transdermal formulations may be prepared in the form of matrices or membranes, or as fluid or viscous formulations in oil or hydrogels or as a compressed powder pellet. For transdermal patches, an adhesive which is compatible with the skin may be included, such as polyacrylate, a silicone adhesive or polyisobutylene, as well as a foil made of, e.g., polyethylene, polypropylene, ethylene vinylacetate, polyvinylchloride, polyvinylidene chloride or polyester, and a removable protective foil made from, e.g., polyester or paper coated with silicone or a fluoropolymer. For the preparation of transdermal solutions or gels, water or organic solvents or mixtures thereof may be used. Transdermal gels may furthermore contain one or more suitable gelling agents or thickeners such as silicone, tragacanth, starch or starch derivatives, cellulose or cellulose derivatives or polyacrylic acids or derivatives thereof. Transdermal formulations may also suitably contain one or more substances that enhance absorption though the skin, such as bile salts or derivatives thereof and/or phospholipids. Transdermal formulations may be prepared according to a method disclosed in, e.g., B W Barry, "Dermatological Formulations, Percutaneous Absorption", Marcel Dekker Inc., New York—Basel, 1983, or Y W Chien, "Transdermal Controlled Systemic Medications", Marcel Dekker Inc., New York--Basel, 1987.

It will be understood from the a foregoing that there are provided pharmaceutical products comprising an alkali metal salt, particularly sodium salt, of a boronic acid of Formula (I) in dry fine particle form, suitable for reconstitution into an aqueous read-to-use parenteral formulation. The alkali metal salt is suitably an acid salt. The alkali metal salt may be in a small volume parenteral unit dosage form. The alkali metal salt may be presented in a form, e.g. dry powder form, suitable for reconstituting as a large volume parenteral. One example is a sodium salt of a boronic acid of Formula (I), particularly TRI 50c, in dry powder form for reconstitution as a liquid intravenous formulation (solution) containing a tonicity agent, particularly sodium chloride. The dry powder form of a salt used in a parenteral formulation may be a lyophilisate. The reconstituted solution may be administered by injection or infusion.

Synthesis

1. Peotide/Peptidomimetic Synthesis

The synthesis of boropeptides, including, for example, Cbz—D—Phe—Pro—BoroMpg—OPinacol is familiar to those skilled in the art and described in the prior art mentioned above, including Claeson et al (U.S. Pat. No. 5,574,014 and others) and Kakkar et al (WO 92/07869 and family members including U.S. Pat. No. 5,648,338). It is described also by Elgendy et al *Adv. Exp. Med. Biol.* (*USA*) 340:173-178, 1993; Claeson,G. et al *Biochem.J.* 290:309-312, 1993; Deadman et al *J. Enzyme Inhibition* 9:29-41, 1995, and by Deadman et al *J. Med. Chem.* 38:1511-1522, 1995.

Stereoselective synthesis with S or R configuration at the chiral B-terminal carbon may be conducted using established methodology (Elgendy et al *Tetrahedron. Lett.* 33:4209-4212, 1992; WO 92/07869 and family members including U.S. Pat. No. 5,648,338) using (+) or (−)-pinanediol as the chiral director (Matteson et al *J. Am. Chem. Soc.* 108:810-819, 1986; Matteson et al *Organometallics*. 3:1284-1288, 1984). Another approach is to resolve the requisite aminoboronate intermediate (e.g. Mpg-BOPinacol) to selectively obtain the desired (R)-isomer and couple it to the dipeptide moiety (e.g. Cbz-(R)-Phe-(S)-Pro, which is the same as Cbz-D-Phe-L-Pro) which will form the remainder of the molecule.

The boropeptides may be synthesised initially in the form of boronic acid esters, particularly esters with diols. Such diol esters may be converted to the peptide boronic acid as described next.

2. Ester to Acid Conversion

A peptide boronate ester such as Cbz-(R)-Phe-Pro-BoroMpg-OPinacol may be hydrolysed to form the corresponding acid.

A novel technique for converting a diol ester of a peptide boronic acid of formula (I) into the acid comprises dissolving the diol ester in an ether and particularly a dialkyl ether, reacting the thus-dissolved diol with a diolamine, for example a dialkanolamine, to form a product precipitate, recovering the precipitate, dissolving it in a polar organic solvent and reacting the thus-dissolved product with an aqueous medium, e.g. an aqueous acid, to form the peptide boronic acid. The boronic acid may be recovered from the organic layer of the mixture resulting from the reaction, for example by removing the solvent, e.g. by evaporation under vacuum or distillation. The reaction between the diol ester and the diolamine may be carried out under reflux, for example.

The identity of the diol is not critical. As suitable diols may be mentioned aliphatic and aromatic compounds having hydroxy groups that are substituted on adjacent carbon atoms or on carbon atoms substituted by another carbon. That is to say, suitable diols include compounds having at least two hydroxy groups separated by at least two connecting carbon atoms in a chain or ring. One class of diols comprises hydrocarbons substituted by exactly two hydroxy groups. One such diol is pinacol and another is pinanediol; there may also be mentioned neopentylglycol, 1,2-ethanediol, 1,2-propanediol, 1,3-propanediol, 2,3-butanediol, 1,2-diisopropylethanediol, 5,6-decanediol and 1,2-dicyclohexylethanediol.

The alkyl groups of the dialkyl ether preferably have 1, 2, 3 or 4 carbon atoms and the alkyl groups may be the same or different. An exemplary ether is diethyl ether.

The alkyl groups of the dialkanolamine preferably have 1, 2, 3 or 4 carbon atoms and the alkyl groups may be the same or different. An exemplary dialkanolamine is diethanolamine. The diethanolamine/boronic acid reaction product hydrolyses in water at room temperature and the rate of hydrolysis may be accelerated by adding acid or base.

The polar organic solvent is preferably $CHCl_3$. Other examples are polyhalogenated alkanes generally and ethyl acetate. In principle, any polar organic solvent is acceptable other than alcohols.

The aqueous acid is suitably a strong inorganic acid at a pH in the region of 1 such as hydrochloric acid, for example.

After reaction with the acid, the reaction mixture is suitably washed with, for example, $NH_4Cl$ or another mild base.

An example of a specific procedure is as follows
1. The pinacol or pinanediol ester of the selected peptide boronic acid is dissolved in diethylether.
2. Diethanolamine is added and the mixture is refluxed at 40° C.
3. The precipitated product is removed (filtered), washed (usually several times) with diethyl ether or another polar organic solvent other than an alcohol, and dried (e.g. by evaporation under vacuum).
4. The dry product is dissolved in a polar organic solvent other than an alcohol, e.g. $CHCl_3$. Aqueous acid or base is added ,e.g. hydrochloric acid (pH 1), and the mixture is stirred for e.g. approximately 1 h at room temperature.
5. The organic layer is removed and washed with $NH_4Cl$ solution.
6. The organic solvent is distilled off and the residual solid product is dried.

The above process results in the formation of what may conveniently be referred to as a "diolamine adduct" of the peptide boronic acids of formula (I), especially such adducts with diethanolamine, and such adducts are themselves included in the disclosure. The molecular structure of such adducts is not known: they might comprise a compound in which the two oxygens and the nitrogen of the diolamine are all coordinated to the boron; they might comprise ions. The adducts are however considered to be esters. A particular novel product included in the disclosure is that obtainable by reacting a pinacol or pinanediol ester of a compound of Formula VIII, particularly (R,S,R)-TRI 50c, and diethanolamine, i.e. the novel product is an (R,S,R)-TRI 50c/diethanolamine "adduct" where the acid is (R,S,R)-TRI 50c.

The diolamine materials of the disclosure may be defined as a composition of matter comprising:
(i) a species of formula (XII)

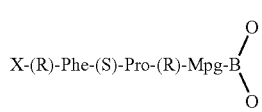

(XII)

wherein X is H or an amino protecting group, the boron atom is optionally coordinated additionally with a nitrogen atom, and the valency status of the terminal oxygens is open (they may be attached to a second covalent bond, be ionised as —O⁻, or have some other, for example intermediate, status); and, in bonding association therewith (ii) a species of formula (XIII)

(XIII)

wherein the valency status of the nitrogen atom and the two oxygen atoms is open. It will be appreciated that the terminal oxygen atoms of the species of formula (IX) and the oxygen atoms of the species of formula (X) may be the same oxygen atoms, in which case the species of formula (X) forms a diol ester with the species of formula (IX).

It will be appreciated that the a foregoing technique comprises an example of a method for recovering an organoboronic acid product, the method comprising providing in a solvent a dissolved mixture comprising the organoboronic acid in a soluble form and a compound having two hydroxy groups and an amino group (i.e. a diolamine), causing or allowing the organoboronic acid and the diolamine to react to form a precipitate, and recovering the precipitate. The soluble form of the organoboronic acid may be a diol ester, as discussed above. The solvent may be an ether, as discussed above. The organoboronic acid may be one of the organoboronic acids referred to in this specification, for example it may be of Formula (I) or (III). The method described in this paragraph is novel and forms an aspect of the disclosure. A recovery method is filtration.

The reaction between the diolamine and the soluble form of the organoboronic acid is suitable carried out at an elevated temperature, for example under reflux.

Another aspect of the disclosure is a method for recovering an organoboron species, comprising
providing, in a form soluble in an ether, an organoboronic acid, for example a drug such as, e.g., a compound of formula (III);
forming a solution of the soluble form in the ether;
combining the solution with a dialkanolamine and allowing or causing the dialkanolamine to react with the soluble form of the organoboronic acid to form an insoluble precipitate; and
recovering the precipitate.

The term "soluble" in the preceding paragraph refers to species which are substantially more soluble in the reaction medium than is the precipitated product. In variants of the method, the ether is replaced by toluene or another aromatic solvent.

The diethanolamine precipitation technique described above is an example of another novel method, which is a method for recovering from ether solution a pinacol or pinanediol ester of a peptide boronic acid, comprising dissolving diethanolamine in the solution, allowing or causing a precipitate to form and recovering the precipitate. The disclosure encompasses variants of this methods in which another diol than pinacol or pinanediol is used.

The precipitated material, i.e. the "adduct", may be converted into the free organoboronic acid, for example by contacting it with an acid. The acid may be an aqueous acid, for example an aqueous inorganic acid, e.g. as described above. The precipitate may be dissolved, for example in an organic solvent, prior to being contacted with the acid.

The disclosure therefore provides a method for making an organoboronic acid, comprising converting its diolamine reaction product to the acid.

The acid resulting from the methods described in the previous two paragraphs may be converted to a salt of the acid with a multivalent metal, which salt may in turn be formulated into a pharmaceutical composition in parenteral dosage form.

3. Salt Synthesis

In general, the salts may be prepared by contacting the relevant peptide boronic acid with a strong base appropriate to form the desired salt. In the case of metal salts, the metal hydroxides are suitable bases (alternatively, metal carbonates might be used, for example), whilst sometimes it is more convenient to contact the acid with a relevant metal alkoxide (eg methoxide), for which purpose the corresponding alkanol is a suitable solvent. Salts with organic bases may be prepared by contacting the peptide boronic acid with the organic base itself. Illustrative salts are acid salts (one —BOH proton replaced) and, to make acid salts with a monovalent cation, the acid and the base are suitably reacted in substantially equimolar quantities. Generally stated, therefore, the usual acid:base molar ratio is substantially n:1, where n is the valency of the cation of the base.

In one procedure, a solution of the peptide boronic acid in a water-miscible organic solvent, for example acetonitrile or an alcohol (e.g. ethanol, methanol, a propanol, for example iso-propanol, or another alkanol), is combined with an aqueous solution of the base. The acid and the base are allowed to react and the salt is recovered. The reaction is typically carried out at ambient temperature (e.g. at a temperature of from 15 to 30° C., e.g. 15 to 25° C.), but an elevated temperature may be used, for example up to the boiling point of the reaction mixture but more usually lower, e.g. a temperature of up to 40° C. or 50° C. The reaction mixture may be allowed to stand or be agitated (usually stirred).

The time during which the acid and the base are allowed to react is not critical but it has been found desirable to maintain the reaction mixture for at least one hour. A period of from one to two hours is usually suitable but longer reaction times may be employed.

The salt may be recovered from the reaction mixture by any suitable method, for example evaporation or precipitation. Precipitation may be carried out by adding an excess of a miscible solvent in which the salt has limited solubility. In one preferred technique, the salt is recovered by evacuating the reaction mixture to dryness. The salt is preferably thereafter purified, for example by redissolving the salt before filtering the resulting solution and drying it, for example by evacuating it to dryness. The redissolution may be performed using water, e.g. distilled water. The salt may then be further purified, for example in order to remove residual water by further redissolution in a suitable solvent, which is advantageously ethyl acetate or THF followed by evaporating to dryness. The purification procedure may be carried out at ambient temperature (say, 15 to 30° C., e.g. 15 to 25° C.), or at a modestly elevated temperature, such as e.g. a temperature not exceeding 40° C. or 50° C.; for example the salt may be dissolved in water and/or solvent by agitating with or without warming to, for example, 37° C.

Also included is a method for drying the salts of the disclosure and other peptide boronic acid salts, comprising dissolving them in an organic solvent, e.g. ethyl acetate or THF, and then evaporating to dryness, e.g. by evacuation.

Generally, preferred solvents for use in purifying the salts are ethyl acetate or THF, or perhaps another organic solvent.

A general procedure for synthesising salts of Cbz-Phe-Pro-BoroMpg-OH is as follows:

Cbz-Phe-Pro-BoroMpg-OH (20.00 g, 38.1 mM) is dissolved in acetonitrile (200 ml) with stirring at room temperature. To this solution is added the requisite base in solution in distilled water (190 ml); the base is added as a 0.2M solution for a monovalent cation. The resultant clear solution is allowed to react for example by being left to stand or being agitated, for a usual period, in either case, of from one to two hours. The reaction is typically carried out at ambient temperature (e.g. 15-30° C., e.g. 15 to 25° C.) but alternatively the temperature may be elevated (e.g. up to 30° C., 40° C. or 50° C.). The reaction mixture is then evacuated to dryness under vacuum with its temperature not exceeding 37° C., typically to yield a white brittle solid or an oil/tacky liquid. The oil/tacky liquid is redissolved in the minimum amount of distilled water necessary (200 ml to 4L), typically with warming (e.g. to 30-40° C.), usually for up to 2 hours. The solution is filtered, suitably through filter paper, and evacuated, to dryness, again with the temperature of the solution not exceeding 37° C., or freeze dried. The resultant product is dried under vacuum overnight to normally yield a white brittle solid. If the product is present as an oil or tacky solid then it is dissolved in ethyl acetate and evacuated to dryness to produce the product as a white solid. The white solid is typically a coarse, amorphous powder.

In variations of the a foregoing general procedure, the acetonitrile is replaced by another water-miscible organic solvent, notably an alcohol, as discussed above, especially ethanol, methanol, iso-propanol or another propanol.

Where a boronic acid salt is less soluble in a selected reaction medium for salt formation such that its direct preparation from the corresponding acid and base is inconvenient, the less soluble salt may be prepared from a salt more soluble in the reaction medium.

There is provided also the use of a boronic acid to make a salt of the disclosure. Included also is a method of preparing a product of the disclosure, comprising contacting a boronic acid, e.g. of formula (I), (II) or (III), with a base capable of making such a salt.

The peptide boronic acid of formula (I) used to prepare the pharmaceutical preparations is typically of GLP or GMP quality, or in compliance with GLP (good laboratory practice) or GMP (good manufacturing practice); such acids are included in the disclosure.

Similarly the acids are usually sterile and/or acceptable for pharmaceutical use, and one aspect of the disclosure reside in a composition of matter which is sterile or acceptable for pharmaceutical use, or both, and comprises a peptide boronic acid of formula (I). Such a composition of matter may be in particulate form or in the form of a liquid solution or dispersion.

The intermediate acid may be in isolated form and such isolated acids are included in the disclosure, especially isolated acids which are a peptide boronic acid of formula (VIII):

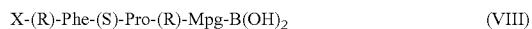

X-(R)-Phe-(S)-Pro-(R)-Mpg-B(OH)$_2$     (VIII)

wherein X is H (to form NH$_2$) or an amino-protecting group.

One typical way of providing the intermediate acids is as a particulate composition consisting predominantly of such a peptide boronic acid, and these compositions are included in the disclosure. The peptide boronic acid often forms at least 75% by weight of the composition and typically at least 85% by weight of the composition, e.g. at least 95% by weight of the composition.

Another typical way of providing the intermediate acids is as a liquid composition consisting of, or consisting essentially of, a peptide boronic acid of formula (II) and a liquid vehicle in which it is dissolved or suspended. The liquid vehicle may be an aqueous medium, e.g. water, or an alcohol, for example methanol, ethanol, isopropanol, or another propanol, another alkanol or a mixture of the a foregoing.

The compositions of the intermediate acids are generally sterile. The compositions may contain the peptide boronic acid in finely divided form, to facilitate further processing.

Separation of Stereoisomers

The stereoisomers of a peptide boronic ester or a synthetic intermediate aminoboronate may be resolved in, for example, any known way. In particular, stereoisomers of boronic esters may be resolved by HPLC.

EXAMPLES

Examples 1 to 4

Introductory Remarks

Apparatus

Throughout the following procedures of Examples 1 to 4, standard laboratory glassware and, where appropriate, specialised apparatus for handling and transferring of air sensitive reagents are used.

All glassware is heated at 140-160° C. for at least 4 hours before use and then cooled either in a desiccator or by assembling hot and purging with a stream of dry nitrogen.

Solvents

The organic solvents used in the procedures of Examples 1 to 4 are all dry. Suitably, they are dried over sodium wire before use.

Dryness

In the drying procedures of Example 1 to 4, products are tested for dryness (including dryness in terms of organic solvent) by observing weight loss on drying. The following procedure was followed to determine loss on drying: a sample was placed in a vacuum drier and dried at 40° C. at 100 mbar for 2 hours. Products are considered dry when the decrease in weight upon drying is less than 0.5% of the total weight of the starting material.

Examples 1 to 4 describe performance of the following reaction scheme and conversion of the resultant TRI 50c to sodium and calcium salts thereof:

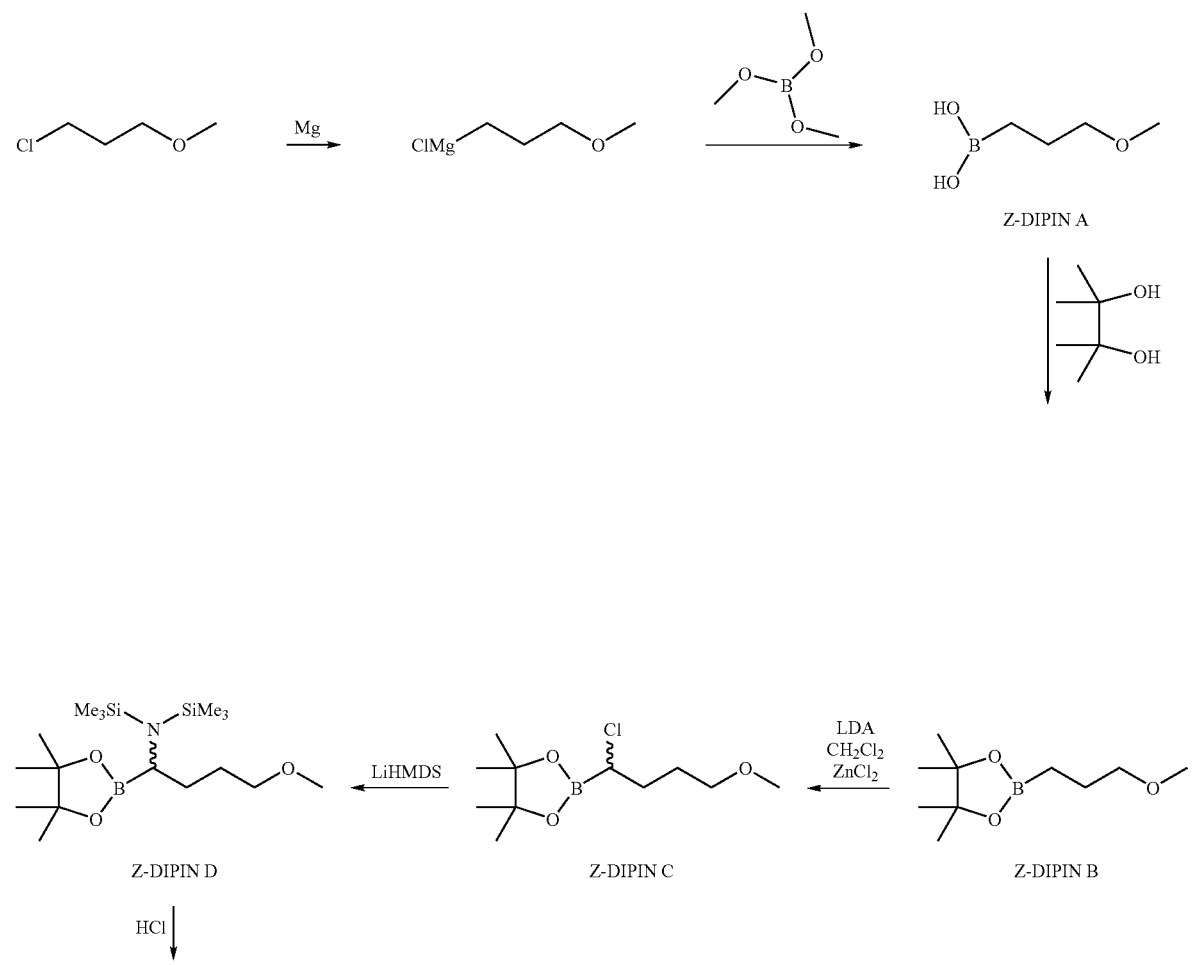

41
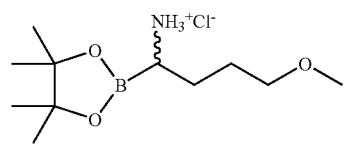
Z-DIPIN E
+
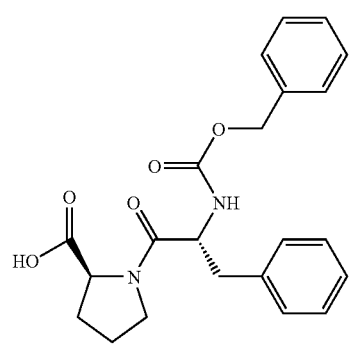
Z-DIPIN-H
-continued
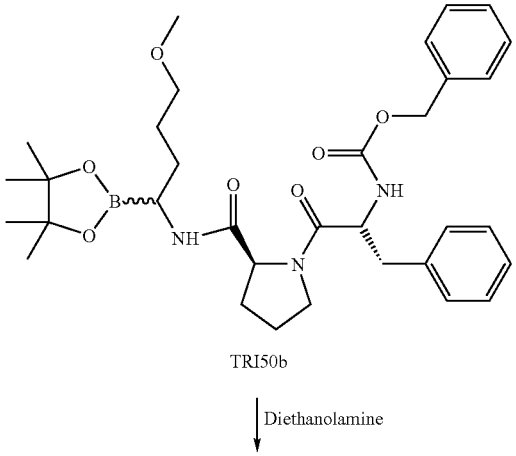
TRI50b
↓ Diethanolamine
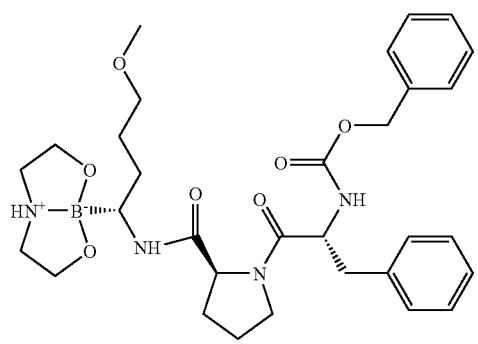
TRI50d
Acid ↙
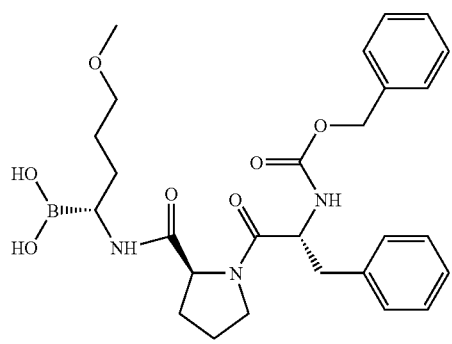
TRI50c
LDA = lithium diisopropylamide
LiHMDS = lithium hexamethyldisilazane, also known as lithium bis(trimethylsilyl)amide

Example 1

Synthesis of TRI 50D

Step 1: Z-DIPIN B

Procedure A 17.8 g (732.5 mmole) magnesium turnings, 0.1 g (0.4 mmole) iodine and 127 ml dry tetrahydrofuran are charged and heated to reflux. Then 15 ml of a solution of 66 g (608 mmole) 1-chloro-3-methoxypropane in 185 ml dry tetrahydrofuran are added and stirred under reflux until the vigorous reaction starts. After the initial exotherm ceases, the solution of 1-chloro-3-methoxypropane is added slowly to maintain gentle reflux until all the magnesium is consumed. After the reaction is finished, the reaction mixture is cooled to ambient temperature and slowly added to a solution of 64.4 g (620 mmole) trimethylborate in 95 ml dry tetrahydrofuran; the latter solution is cooled to below 0° C. and, if it warms up during the course of the reaction, the reaction mixture must be added to it sufficiently slowly to maintain the temperature of this solution below 65° C. Upon complete addition, the reaction mixture is allowed to warm to about 0° C. and stirred for another 60 minutes. Then a solution of 22.4 ml sulfuric acid in 400 ml water is added slowly so as to maintain the temperature below 20° C. The layers are allowed to settle and the phases are separated. The aqueous layer is rewashed three times with 200 ml tert.-butylmethylether. The combined organic layers are allowed to settle and additional water separated from this solution is removed. The organic layer is dried over magnesium sulfate, filtered and evaporated to dryness. The evaporation residue is filtered from the precipitated solid and the filtrate dissolved in 175 ml toluene. 34.8 g (292 mmole) pinacol is charged to the solution followed by stirring at ambient temperature for not less than 10 hours. The solution is evaporated to dryness, dissolved in 475 ml n-heptane and washed three times with 290 ml saturated aqueous solution of sodium hydrogen carbonate. The n-heptane solution is evaporated to dryness and the evaporation residue distilled and the fraction with Bp 40-50° C. at 0.1-0.5 mbar recovered.

Boiling point: 40-50° C./0.1-0.5 mbar

Yield: 40.9 g (70%) Z-DIPIN B (oil)

Procedure B 17.8 g (732.5 mmole) magnesium turnings, 0.1 g (0.4 mmole) iodine and 127 ml dry tetrahydrofuran are charged and heated to reflux. Then 15 ml of a solution of 66 g (608 mmole) 1-chloro-3-methoxypropane in 185 ml dry tetrahydrofuran are added and stirred under reflux until the vigorous reaction starts. After the initial exotherm ceases, the solution of 1-chloro-3-methoxypropane is added slowly to maintain gentle reflux. After the reaction is finished, the reaction mixture is cooled to ambient temperature and slowly added to a solution of 64.4 g (620 mmole) trimethylborate in 95 ml dry tetrahydrofuran, maintaining the temperature of this solution below minus 65° C. Upon complete addition, the reaction mixture is allowed to warm to about 0° C. and stirred for another 60 minutes. Then a solution of 22.4 ml sulfuric acid in 400 ml water is added slowly so as to maintain the temperature below 20° C. The organic solvent is removed by distillation under vacuum. 300 ml n-heptane is charged to the aqueous solution of the evaporation residue followed by addition of 34.8 g (292 mmole) pinacol. The two-phase-mixture is stirred at ambient temperature for not less than 2 hours. After allowing the layers to settle, the aqueous phase is separated. 300 ml n-heptane is charged to the aqueous solution and the two-phase-mixture is stirred at ambient temperature for not less than 2 hours. After allowing the layers to settle, the aqueous phase is separated. The organic layers are combined and washed once with 200 ml water, followed by 200 ml saturated sodium hydrogen carbonate solution and two further washes with 200 ml water each. The n-heptane solution is evaporated to dryness and the evaporation residue distilled and the fraction with Bp 40-50° C. at 0.1-0.5 mbar recovered.

Boiling point: 40-50° C./0.1-0.5 mbar

Yield: 40.9 g (70-85%) Z-DIPIN B (oil)

Step 2: Z-DIPIN C 16.6 g (164 mmole) diisopropylamine and 220 ml tetrahydrofuran are charged and cooled to −30 to -40° C. To this solution 41.8 g (163 mmole) n-butyl lithium, 25% in n-heptane is added, followed by stirring at 0 to −5° C. for one hour. This freshly prepared solution of lithium diisopropylamide is cooled to −30° C. and then added to a solution of 27.9 g (139 mmole) Z-DIPIN B in 120 ml tetrahydrofuran and 35.5 g (418 mmole) dichloromethane at a temperature between −60 and −75° C. The solution is stirred at that temperature for half an hour followed by addition of 480 ml (240 mmole) 0.5N anhydrous Zinc(II)-chloride in tetrahydrofuran or 32.5 g (240 mmole) anhydrous solid Zinc(II)-chloride. After stirring at −-65° C. for one hour, the reaction mixture is allowed to warm to ambient temperature and stirred for another 16-18 hours. The reaction mixture is evaporated to dryness (i.e. until solvent is removed) and followed by addition of 385 ml n-heptane. The reaction mixture is washed with 150 ml 5% sulfuric acid, with 190 ml saturated sodium hydrogen carbonate solution, and 180 ml saturated sodium chloride solution. The organic layer is dried over magnesium sulfate, filtered and evaporated to dryness (i.e. until solvent is removed). The oily residue is transferred into the next step without further purification.

Yield: 19 g (55%) Z-DIPIN C

Step 3: Z-DIPIN D

To a solution of 23.8 g (148 mmole) hexamethyldisilazane in 400 ml tetrahydrofuran at −15° C. is added 34.7 g (136 mmole) n-butyl lithium, 25% in n-heptane and stirred for one hour. The solution is cooled to −55° C. followed by the addition of 30.6 g (123 mmole) Z-DIPIN C dissolved in 290 ml tetrahydrofuran and 35 ml tetrahydrofuran to this freshly prepared solution of LiHMDS. The solution is allowed to warm to ambient temperature and stirred for 12 hours. The reaction mixture is evaporated to dryness, the evaporation residue dissolved in 174 ml n-heptane, washed with 170 ml water and 75 ml saturated sodium chloride solution. The organic phase is dried over magnesium sulfate, filtered and evaporated to complete dryness (i.e. until solvent is removed). The oily residue is dissolved in 100 g n-heptane. This solution is carried over into the next step without further purification.

Yield: 32.2 g (70%) Z-DIPIN D

Step 4: Z-DIPIN (TRI5Ob, crude)

A solution of 26.6 g (71 mmole) Z-DIPIN D in 82.6 g n-heptane is diluted with 60 ml n-heptane and cooled to −60° C. followed by introduction of 10.5 g (285 mmole) hydrogen chloride. The reaction mixture is subsequently evacuated and flushed with nitrogen, while the temperature is increased in increments of about 20° C. to ambient temperature. The solvent is removed from the oily precipitate and replaced several times by 60 ml fresh n-heptane. The oily residue is dissolved in 60 ml tetrahydrofuran (Solution A).

To a different flask 130 ml tetrahydrofuran, 24.5 g (61.5 mmole) Z-D-Phe-Pro-OH and 6.22 g (61.5 mmole) N-methylmorpholine are charged and cooled to −20° C. To this solution a solution of 8.4 g (61.5 mmole) isobutylchloroformate in 20 ml tetrahydrofuran is added and stirred for 30 minutes, followed by addition of Solution A at −25° C. Upon complete addition, up to 16 ml (115 mmole) triethylamine is added to adjust the pH to 9-10, measured using a pH stick. The reaction mixture is allowed to warm to ambient temperature and stirred for 3 hours, still under nitrogen. The solvent is evaporated to dryness and the evaporation residue dissolved in 340 ml tert.-butylmethylether (t-BME). The solution of Z-DIPIN in t-BME is washed twice with 175 ml 1.5% hydrochloric acid. The combined acidic washes are given a rewash with 175 ml t-BME. The combined organic layers are washed with 175 ml water, with 175 ml saturated sodium hydrogen carbonate solution, with 175 ml 25% sodium chloride solution, dried over magnesium sulfate and filtered. This solution is carried over into the next step without further purification.

Yield: 29.9 g (80%) Z-DIPIN

Example 2

Synthesis of TRI 50D (Diethanolamine Adduct of TRI 50C)

The starting material used in this Example is the solution of TRI 50b ("Z-DIPIN") obtained in Example 1. The solution is carried forward to the synthesis of TRI 50d without further purification. The solution of Z-DIPIN in t-BME (containing 7.0 g (11.5 mmole) (R,S,R) TRI50b, calculated based on HPLC results of Z-DIPIN) is evaporated to dryness and the evaporation residue dissolved in 80 ml diethylether. 1.51 g (14.4 mmole) diethanolamine is added and the mixture heated at reflux for at least 10 hours, during which process the product precipitates. The suspension is cooled to 5-10° C., filtered and the filter residue washed with diethylether.

To improve chiral and chemical purity the wet filter cake (7 g) is dissolved in 7 ml dichloromethane, cooled to 0-5° C. and the product precipitated by addition of 42 ml diethylether and filtered. The isolated wet product is dried at 35° C. in vacuum or at least 4 hours, until day.

Yield: 5.5 g (80%) Tri50d
Melting Point: 140-145° C.

Example 3

Preparation of Sodium Salt of TRI50C 1.5 kg (2.5 mole) TRI50d from Example 2 is dissolved in 10.5 L dichloromethane. 11 L 2% hydrochloric acid is added and the mixture is stirred for at most 30 minutes (optimally about 20 minutes) at room temperature. A precipitate forms in the organic phase. After stirring, the layers are allowed to settle and separated. The aqueous layer is rewashed twice with 2.2 L dichloromethane. The combined organic layers are washed with a solution of 625 g ammonium chloride in 2.25 L water. (The ammonium chloride buffers the pH of the aqueous extractions to be within a range of from about pH 1-2 to about pH 4-5, as strongly acidic conditions might cleave peptide bonds). The organic phase is dried over magnesium sulfate, filtered and the filtrate evaporated to dryness. An assay of the free boronic acid is performed (by the RP HPLC method of Example ___ for at most 30 mins (optionally about 20 min) at room temperature) and the amounts of the solvents and base for conversion of the acid to the salt are calculated. If 2.5 mol of the free acid is obtained, the evaporation residue is dissolved in 5 L acetonitrile followed by addition of a solution of 100 g (2.5 mole) sodium hydroxide as a 5% solution in 2.2 L water. The solution is stirred for two hours at ambient temperature (e.g. 15-30° C., optimally room temperature) and then evaporated in vacuum (of ca. 10 mmHg) at a temperature not exceeding 35° C. The evaporation residue is repeatedly dissolved in 3.5 L fresh acetonitrile and evaporated to dryness to remove traces of water. If the evaporation residue is dry, it is dissolved in 3 L acetonitrile (or alternatively in 6 L THF) and slowly added to a mixture of 32 L n-heptane and 32 L diethylether. The addition is performed slowly enough to avoid lumping or sticking of the product and is carried out over a period of not less than 30 minutes. The precipitated product is filtered off, washed with n-heptane and dried under vacuum at a temperature initially of about 10° C. and then increasing to a limit of about 35° C., until dry.

Yield: 1.0 kg (70%) Tri50c sodium salt.

Example 4

Preparation of Calcium Salt of TRI50C 1.5 kg (2.5 mole) TRI50d from Example 2 is dissolved in 10.5 L dichloromethane. 11 L 2% hydrochloric acid is added and the mixture is stirred for at most 30 minutes (optimally about 20 minutes) at room temperature. After stirring the layers are allowed to settle and separated. The aqueous layer is given a rewashed twice with 2.2 L dichloromethane. The combined organic layers are washed with a solution of 625 g ammonium chloride in 2.25 L water. The organic phase is dried over magnesium sulfate, filtered and the filtrate evaporated to dryness. An assay of the free boronic acid is performed and the amounts of the solvents and base for conversion of the acid to the salt are calculated. If 2.5 mol of the free acid is obtained, the evaporation residue is dissolved in 5 L acetonitrile followed by addition of a suspension of 93 g (1.25 mole) calcium hydroxide in 1 L water. The solution is stirred for two hours at ambient temperature (e.g. 15-30° C., optimally room temperature) and then evaporated under vacuum (of ca. 10 mmHg) at a temperature initially of about 10° C. and then increasing to a limit of about 35° C. The evaporation residue is repeatedly dissolved in 3.5 L fresh acetonitrile and evaporated to dryness to remove traces of water. If the evaporation residue is dry, it is dissolved in 6 L tetrahydrofuran and slowly added to a mixture of 32 L n-heptane and 32 L diethylether. The addition is performed slowly enough to avoid lumping or sticking of the product and is carried out over a period of not less than 30 minutes. The precipitated product is filtered off, washed with n-heptane and dried under vacuum (of ca. 10 mmHg) at a temperature below 35° C. until dry.

Yield: 0.98 kg (70%) Tri50c calcium salt.

The procedures of Examples 1 to 4 may be scaled up and, if operated carefully, will produce highly pure salts. In the diethanolamine precipitation step it is important to use 1.25 equivalents of diethanolamine per equivalent of (R,S,R) TRI 50b. In the hydrolysis of the diethanolamine ester, it is important to avoid excessively long contact with the aqueous acid. Likewise the TRI 50b should be synthesised via the Grignard reaction to Z-DIPIN A.

Example 5

Alternative Conversion of TRI 50B to TRI 50C

The synthetic procedures described in this and subsequent synthetic examples were generally performed under nitrogen and using dry solvents as supplied from commercial sources.
1. Approximately 300 g of TRI 50b, obtained by the HPLC purification of racemic TRI 50b) were dissolved in approximately 2.5 L diethylether. It is estimated that different batches of TRI 50b had isomeric purities ranging from 85% R,S,R to in excess of 95% R,S,R.
2. Approximately 54 ml diethanolamine were added (1:1 stoichiometry with total TRI 50b content), and the mixture was refluxed at 40° C.
3. The precipitated product was removed, washed several times with diethylether and dried.
4. The dry product was dissolved in $CHCl_3$. Hydrochloric acid (pH 1) was added and the mixture was stirred approximately 1 h at room temperature.
5. The organic layer was removed and washed with $NH_4Cl$ solution.
6. The organic solvent was distilled off and the residual solid product was dried.

Typical yield: Approximately 230 g

Example 6

Preparation of Lithium Salt of TRI50C

Cbz-Phe-Pro-BoroMpg-OH obtained by the method of Example 5 (20.00 g, 38.1 mM) is dissolved in acetonitrile (200 ml) with stirring at room temperature. To this solution is added LIOH as a 0.2M solution in distilled water (190 ml). The resultant clear solution is stirred for 2 hours at room temperature and then evacuated to dryness under vacuum with its temperature not exceeding 37° C. The resultant oil/tacky liquid is redissolved in 500 ml distilled water necessary with light warming for about 20 minutes. The solution is filtered through filter paper and evacuated to dryness, again with the temperature of the solution not exceeding 37° C. The resultant product is dried under vacuum overnight to normally yield a white brittle solid.

The salt was then dried under vacuum over silica to constant weight (72 h).

Yield 17.89 g.

Microanalysis:

| C % Found (Calc.) | H % Found (Calc.) | N % Found (Calc.) | B % Found (Calc.) | Metal % Found (Calc.) |
|---|---|---|---|---|
| 57.14 (61.03) | 6.60 (6.64) | 7.34 (7.90) | 2.07 (2.03) | Li 1.26 (1.31) |

Example 7

UV/Visible Spectra of Lithium Salt of TRI50C

UV/Visible spectra of the salt resulting from the procedure of Example 6 were recorded in distilled water at 20° C. from 190 nm to 400 nm. The salt gave $\lambda_{max}$ at 210 and 258 nm. The weight of the dried salt was then measured for the purposes of calculating the extinction coefficient. The $\lambda_{max}$ at 258 nm was used. The extinction coefficient was calculated using the formula:

$A = \epsilon c l$ where A is the absorbance

C is the concentration

I the path length of the UV cell and $\epsilon$ is the extinction coefficient.

Extinction coeffiident: 451

Example 8

Aqueous Solubility of Lithium Salt of TRI50C

The salt used in this Example was made using a modification of the process described in Example 6. The modified process differs from that described in that 100 mg of TRI 50c was used as starting material, the product of the redissolution in water was dried by freeze drying and the filtration was carried out through a 0.2 μm filter. The salt is believed to contain about 85% of R,S,R isomer.

To determine maximum aqueous solubility 25 mg of the dried salt were shaken in water at 37° C., the sample filtered and the UV spectrum measured. The salt left a white residue of undissolved material. The lithium salt was comparatively soluble and so was redissolved at 50 mg/ml in the same manner previously described.

Solubility when dissolved at 25 mg/ml: 43 mM (23 mg/ml).

Solubility when dissolved at 50 mg/ml: 8 lmM (43 mg/ml).

Example 9

Preparation of Sodium Salt of TRI50C

Cbz-Phe-Pro-BoroMpg-OH obtained by the method of Example 5 (20.00 g, 38.1 mM) is dissolved in acetonitrile (200 ml) with stirring at room temperature. To this solution is added NaOH as a 0.2M solution in distilled water (190 ml). The resultant clear solution is stirred for 2 hours at room temperature and then evacuated to dryness under vacuum with its temperature not exceeding 37° C. The resultant oil/tacky liquid is redissolved in 500 ml distilled water with light warming for about 15-20 minutes. The solution is filtered through filter paper and evacuated to dryness, again with the temperature of the solution not exceeding 37° C. The resultant product is dried under vacuum overnight to normally yield a white brittle solid. The product may be present as an oil or tacky solid due to residual water, in which case it is dissolved in ethyl acetate and evacuated to dryness to produce the product as a white solid.

The salt was then dried under vacuum over silica to constant weight (72 h).

Yield: Over 50%.

Microanalysis:

| C % Found (Calc.) | H % Found (Calc.) | N % Found (Calc.) | B % Found (Calc.) | Metal % Found (Calc.) |
|---|---|---|---|---|
| 59.93 (59.24) | 6.47 (6.44) | 7.31 (7.67) | 1.91 (1.98) | Na 3.81 (4.20) |

Example 10

UV/Visible Spectra of Sodium Salt of TRI50C

UV/Visible spectra of the sodium salt resulting from the procedure of Example 9 were recorded in distilled water at 20° C. from 190 nm to 400 nm. The salt gave $\lambda_{max}$ at 210 and 258 nm. The weight of the dried salt was then measured for the purposes of calculating the extinction coefficient. The $\lambda_{max}$ at 258 nm was used. The extinction coefficient was calculated using the formula:

A=εcl where A is the absorbance

C is the concentration l the path length of the UV cell and ε is the extinction coefficient.

Extinction coefficient: 415.

Example 11

Aqueous Solubility of Sodium Salt of TRI50C

The salt used in this Example was made using a modification of the process described in Example 9. The modified process differs from that described in that 100 mg of TRI 50c was used as starting material, the product of the redissolution in water was dried by freeze drying and the filtration was carried out through a 0.2 µm filter. The salt is believed to contain about 85% of R,S,R isomer.

To determine maximum aqueous solubility 25 mg of the dried salt were shaken in water at 37° C., the sample filtered and the UV spectrum measured. The salt left a white residue of undissolved material. The sodium salt was comparatively soluble and so was redissolved at 50 mg/ml in the same manner previously described.

Solubility when dissolved at 25 mg/ml: 44 mM (25 mg/ml).

Solubility when dissolved at 50 mg/ml: 90 mM (50 mg/ml).

Example 12

Preparation of Potassium Salt of TRI50C

Cbz-Phe-Pro-BoroMpg-OH obtained by the method of Example 5 (20.00 g, 38.1 mM) is dissolved in acetonitrile (200 ml) with stirring at room temperature. To this solution is added KOH as a 0.2M solution in distilled water (190 ml). The resultant clear solution is stirred for 2 hours at room temperature and then evacuated to dryness under vacuum with its temperature not exceeding 37° C. The resultant oil/tacky liquid is redissolved in 1L distilled water with warming to 37° C. for about 2 hours. The solution is filtered through filter paper and evacuated to dryness, again with the temperature of the solution not exceeding 37° C. The resultant product is dried under vacuum overnight to normally yield a white brittle solid.

Yield: 14.45 mg.

The salt was then dried under vacuum over silica to constant weight (72 h).

Microanalysis:

| C % Found (Calc.) | H % Found (Calc.) | N % Found (Calc.) | B % Found (Calc.) | Metal % Found (Calc.) |
|---|---|---|---|---|
| 54.84 (57.55) | 6.25 (6.26) | 7.02 (7.45) | 2.01 (1.92) | K 4.29 (6.94) |

Example 13

UV/Visible Spectra of Potassium Salt of TRI50C

UV/Visible spectra of the potassium salt resulting from the procedure of Example 12 were recorded in distilled water at 20° C. from 190 nm to 400 nm. TRI50C and the salt gave $\lambda_{max}$ at 210 and 258 nm. The weight of the dried salt was then measured for the purposes of calculating the extinction coefficient. The $\lambda_{max}$ at 258 nm was used. The extinction coefficient was calculated using the formula:-

A=εcl where A is the absorbance

C is the concentration l the path length of the UV cell and ε is the extinction coefficient.

Extinction coefficient: 438.

Example 14

Aqueous Solubility of Potassium Salt of TRI50C

The salt used in this Example was made using a modification of the process described in Example 12. The modified process differs from that described in that 100 mg of TRI 50c was used as starting material, the product of the redissolution in water was dried by freeze drying and the filtration was carried out through a 0.2 µm filter. The salt is believed to contain about 85% of R,S,R isomer.

To determine maximum aqueous solubility 25 mg of the dried salt were shaken in water at 37° C., the sample filtered and the UV spectrum measured. The salt left a white residue of undissolved material.

Solubility when dissolved at 25 mg/ml: 29 mM (16 mg/ml).

Example 15

Preparation of Zinc Salt of TRI 50C

The relative solubility of zinc hydroxide is such that, if the hydroxide had been used to prepare the corresponding TRI 50c salt using the procedure of Example 6, they would not have resulted in homogeneous salt formation. A new method was therefore developed to prepare the zinc salt, as described in this and the next examples.

TRI 50c sodium salt (2.24 g, 4.10 mM) was dissolved in distilled water (100 ml) at room temperature and zinc chloride in THF (4.27 ml, 0.5M) was carefully added with stirring. A white precipitate that immediately formed was filtered off and washed with distilled water. This solid was dissolved in ethyl acetate and washed with distilled water (2×50 ml). The organic solution was evacuated to dryness and the white solid produced dried over silica in a desiccator for 3 days before microanalysis. Yield 1.20 g.

$^1$H NMR 400 MHz, $\delta_H$(CD$_3$OD) 7.23-7.33 (20H, m, ArH), 5.14 (4H, m, PhCH$_2$), 4.52 (4H, m, $\alpha$CH), 3.65 (2H, m), 3.31 (12H, m), 3.23 (6H, s, OCH$_3$), 2.96 (4H, d, J7.8 Hz), 2.78 (2H, m), 2.58 (2H, m), 1.86 (6H, m), 1.40 (10H, m).

$^{13}$C NMR 75 MHz $\delta_C$(CD$_3$OD) 178.50, 159.00, 138.05, 137.66, 130.54, 129.62, 129.50, 129.07, 128.79, 128.22, 73.90, 67.90, 58.64, 58.18, 56.02, 38.81, 30.06, 28.57, 28.36, 25.29.

FTIR (KBr disc) $\nu_{max}$ (cm$^{-1}$) 3291.1, 3062.7, 3031.1, 2932.9, 2875.7, 2346.0, 1956.2, 1711.8, 1647.6, 1536.0, 1498.2, 1452.1, 1392.4, 1343.1, 1253.8, 1116.8, 1084.3, 1027.7, 916.0, 887.6, 748.6, 699.4, 595.5, 506.5.

Example 16

Preparation of Arginine Salt of TRI50C

Cbz-Phe-Pro-BoroMpg-OH obtained by the method of Example 5 (20.00 g, 38.1 mM) is dissolved in acetonitrile (200 ml) with stirring at room temperature. To this solution is added arginine as a 0.2M solution in distilled water (190 ml). The resultant clear solution is stirred for 2 hours at room temperature and then evacuated to dryness under vacuum with its temperature not exceeding 37° C. The resultant oil/tacky liquid is redissolved in 2L distilled water with warming to 37° C. for 2 hours. The solution is filtered through filter paper and evacuated to dryness, again with the temperature of the solution not exceeding 37° C. The resultant product is dried under vacuum overnight to normally yield a white brittle solid.

The salt was then dried under vacuum over silica to constant weight (72 h).

Yield: 10.54 g.

Microanalysis:

| C % Found (Calc.) | H % Found (Calc.) | N % Found (Calc.) | B % Found (Calc.) |
|---|---|---|---|
| 52.47 (56.65) | 7.12 (7.20) | 15.25 (14.01) | 1.52 (1.54) |

Example 17

UV/Visible Spectra of Arginine Salt of TRI50C

UV/Visible spectra of the salt resulting from the procedure of Example 15 were recorded in distilled water at 20° C. from 190 nm to 400 nm. TRI50C and the salt gave $\lambda_{max}$ at 210 and 258 nm. The weight of the dried salt was then measured for the purposes of calculating the extinction coefficient. The $\lambda_{max}$ at 258 nm was used. The extinction coefficient was calculated using the formula:-

A=$\epsilon$cl where A is the absorbance

C is the concentration l the path length of the UV cell and $\epsilon$ is the extinction coefficient.

Extinction coefficient: 406.

Example 18

Aqueous Solubility of Arginine Salt of TRI50C

The salt used in this Example was made using a modification of the process described in Example 16. The modified process differs from that described in that 100 mg of TRI 50c was used as starting material, the product of the redissolution in water was dried by freeze drying and the filtration was carried out through a 0.2 µm filter. The salt is believed to contain about 85% of R,S,R isomer.

To determine maximum aqueous solubility 25 mg of the dried salt were shaken in water at 37° C., the sample filtered and the UV spectrum measured. The salt left a white residue of undissolved material.

Solubility when dissolved at 25 mg/ml: 14 mM (10 mg/ml).

Example 19

Preparation of Lysine Salt of TRI50C

Cbz-Phe-Pro-BoroMpg-OH obtained by the method of Example 5 (20.00 g, 38.1 mM) is dissolved in acetonitrile (200 ml) with stirring at room temperature. To this solution is added L-lysine as a 0.2M solution in distilled water (190 ml). The resultant clear solution is stirred for 2 hours at room temperature and then evacuated to dryness under vacuum with its temperature not exceeding 37° C. The resultant oil/tacky liquid is redissolved in 3L distilled water with warming to 37° C. for 2 hours. The solution is filtered through filter paper and evacuated to dryness, again with the temperature of the solution not exceeding 37° C. The resultant product is dried under vacuum overnight to normally yield a white brittle solid. The product may be present as an oil or tacky solid (due to residual water), in which case it is then dissolved in ethyl acetate and evacuated to dryness to produce the product as a white solid.

The salt was then dried under vacuum over silica to constant weight (72 h).

Yield: 17.89.

Microanalysis:

| C % Found (Calc.) | H % Found (Calc.) | N % Found (Calc.) | B % Found (Calc.) |
|---|---|---|---|
| 57.03 (59.11) | 7.43 (7.36) | 10.50 (10.44) | 1.72 (1.61) |

Example 20

UV/Visible Spectra of Lysine Salt of TRI50C

UV/Visible spectra of the salt resulting from the procedure of Example 19 were recorded in distilled water at 20° C. from 190 nm to 400 nm. TRI50C and the salt gave $\lambda_{max}$ at 210 and 258 nm. The weight of the dried salt was then measured for the purposes of calculating the extinction coefficient. The $\lambda_{max}$ at 258 nm was used. The extinction coefficient was calculated using the formula:-

A=$\epsilon$cl where A is the absorbance

C is the concentration l the path length of the UV cell and $\epsilon$ is the extinction coefficient.

Extinction coefficient: 437.

Example 21

Aqueous Solubility of Lysine Salt of TRI50C

The salt used in this Example was made using a modification of the process described in Example 19. The modified process differs from that described in that 100 mg of TRI 50c was used as starting material, the product of the redissolution in water was dried by freeze drying and the filtration was carried out through a 0.2 μm filter. The salt is believed to contain about 85% of R,S,R isomer.

To determine maximum aqueous solubility 25 mg of the dried salt were shaken in water at 37° C., the sample filtered and the UV spectrum measured. The salt left a white residue of undissolved material.

Solubility when dissolved at 25 mg/ml: 13 mM (8.6 mg/ml).

Example 22

Preparation of N-Methyl-D-Glucamine Salt of TRI50C

Cbz-Phe-Pro-BoroMpg-OH obtained by the method of Example 5 (20.00 g, 38.1 mM) is dissolved in acetonitrile (200 ml) with stirring at room temperature. To this solution is added N-methyl-d-glucamine as a 0.2M solution in distilled water (190 ml). The resultant clear solution is stirred for 2 hours at room temperature and then evacuated to dryness under vacuum with its temperature not exceeding 37° C. The resultant oil/tacky liquid is redissolved in 500 ml distilled water with light warming for about 20 minutes. The solution is filtered through filer paper and evacuated to dryness, again with the temperature of the solution not exceeding 37° C., or freeze dried. The resultant product is dried under vacuum overnight to normally yield a white brittle solid.

The salt was then dried under vacuum over silica to constant weight (72 h).

Yield: 21.31 g.
Microanalysis:

| C % Found (Calc.) | H % Found (Calc.) | N % Found (Calc.) | B % Found (Calc.) |
| --- | --- | --- | --- |
| 56.67 (56.67) | 7.28 (7.41) | 7.74 (7.77) | 1.63 (1.50) |

Example 23

UV/Visible Spectra of N-Methyl-D-Glucamine Salt of TRI50C

UV/Visible spectra of the salt resulting from the procedure of Example 22 were recorded in distilled water at 20° C. from 190 nm to 400 nm. TRI50C and the salt gave $\lambda_{max}$ at 210 and 258 nm. The weight of the dried salt was then measured for the purposes of calculating the extinction coefficient. The $\lambda_{max}$ at 258 nm was used. The extinction coefficient was calculated using the formula:-

$A = \epsilon c l$ where A is the absorbance

C is the concentration
l the path length of the UV cell
and $\epsilon$ is the extinction coefficient.
Extinction coefficient: 433.

Example 24

Aqueous Solubility of N-Methyl-D-Glucamine Salt of TRI50C

The salt used in this Example was made using a modification of the process described in Example 22. The modified process differs from that described in that 100 mg of TRI 50c was used as starting material, the product of the redissolution in water was dried by freeze drying and the filtration was carried out through a 0.2 μm filter. The salt is believed to contain about 85% of R,S,R isomer.

To determine maximum aqueous solubility 25 mg of the dried salt were shaken in water at 37° C., the sample filtered and the UV spectrum measured. The salt was observed to fully dissolve. The salt was comparatively soluble and so was redissolved at 50 mg/ml in the same manner previously described.

Solubility when dissolved at 25 mg/ml: 35 mM (25 mg/ml).

Solubility when dissolved at 50 mg/ml: 70 mM (50 mg/ml).

Example 25

Alternative Preparation of Arginine Salt of TRI50C

The arginine salt is formed simply by adding a slight molar excess of L-arginine to a solution of 0.2-0.3 mmol of TRI50c in 10 ml of ethyl acetate. The solvent is evaporated after one hour, and the residue is triturated twice with hexane to remove excess arginine.

Example 26

First Preparation of Calcium Salt of TRI 50C

Cbz-Phe-Pro-BoroMpg-OH (20.00 g, 38.1 mM) obtained by the method of Example 5 is dissolved in acetonitrile (200 ml) with stirring at room temperature. To this solution is added $Ca(OH)_2$ as a 0.1M solution in distilled water (190 ml). The resultant clear solution is stirred for 2 hours at room temperature and then evacuated to dryness under vacuum with its temperature not exceeding 37° C. The resultant product is a white brittle solid.

The salt was then dried under vacuum over silica to constant weight (72 h).

Yield: 17.69 g.

Example 27

Second Alternative Preparation of Calcium Salt of TRI 50C 50.0 g TRI 50c (95.2 mmol) were dissolved under stirring in 250 ml acetonitrile at room temperature and then cooled with an ice bath. To this ice cooled solution 100 ml of an aqueous suspension of 3.5 g (47.6 mmol) calcium hydroxide was added dropwise, stirred for 2.5 hours at room temperature, filtered and the resulting mixture evaporated to dryness, the temperature not exceeding 35° C. The clear yellowish oily residue was redissolved in 200 ml acetone and evaporated to dryness. The procedure of redissolving in acetone was repeated one more time to obtain colourless foam.

This foam was redissolved in 100 ml acetone, filtered and added dropwise to an ice cooled solution of 1100 ml petrol ether 40/60 and 1100 ml diethylether. The resulting colourless precipitate was filtered, washed two times with petrol ether 40/60 and dried under high vacuum, yielding 49.48 g of a colourless solid (92%), with a purity of 99.4% according to an HPLC measurement.

Example 28

UV/Visible Spectra of Calcium Salt of TRI 50C

UV/Visible spectra of the salt resulting from the procedure of Example 26 were recorded in distilled water at 20° C. from 190 nm to 400 nm. TRI 50C and the salt gave $\lambda_{max}$ at 210 and 258 nm. The weight of the dried salt was then measured for the purposes of calculating the extinction coefficient. The $\lambda_{max}$ at 258 nm was used. The extinction coefficient was calculated using the formula:-

A=$\epsilon$cl where A is the absorbance

C is the concentration
I the path length of the UV cell
and $\epsilon$ is the extinction coefficient.
Extinction coefficient: 955.

Example 29

Aqueous Solubility of Calcium Salt of TRI 50C

The salt used in this Example was made using a modification of the process described in Example 27. The modified process differs from that described in that 100 mg of TRI 50c was used as starting material, the product of the redissolution in water was dried by freeze drying and the filtration was carried out through a 0.2 μm filter. The salt is believed to contain about 85% of R,S,R isomer.

To determine maximum aqueous solubility 25 mg of the dried salt were shaken in water at 37° C., the sample filtered and the UV spectrum measured. The salt left a white residue of undissolved material.

Solubility when dissolved at 25 mg/ml: 5 mM (5 mg/ml).

Example 30

In Vitro Activity of Calcium Salt of TRI 50C

TRI 50c calcium salt was assayed as an inhibitor of human α-thrombin by an amidolytic assay (J. Deadman et al, *J. Med. Chem.* 38:15111-1522, 1995, which reports a Ki value of 7 nM for TRI 50b).

The inhibition of human α-thrombin therefore, was determined by the inhibition of the enzyme catalysed hydrolysis of three different concentrations of the chromogenic substrate S-2238.

200 μl of sample or buffer and 50 μl of S-2238 were incubated at 37° C. for 1 minute and 50 μl of human α-thrombin (0.25 NIHμ/ml) was added. The initial rate of inhibited and uninhibited reactions were recorded at 4.5 nm. The increase in optical density was plotted according to the method of Lineweaver and Burke. The Km and apparent Km were determined and Ki was calculated using the relationship.

$$V = \frac{V\max}{1 + \frac{Km}{[S]} \cdot \left(1 + \frac{[I]}{Ki}\right)}$$

The buffer used contained 0.1M sodium phosphate, 0.2M NaCl, 0.5% PEG and 0.02% sodium azide, adjusted to pH 7.5 with orthophosphoric acid.

The samples consist of the compound dissolved in DMSO.

The reader is referred to Dixon, M and Webb, E.C., "Enzymes". third edition, 1979, Academic Press, the disclosure of which is incorporated herein by reference, for a further description of the measurement of Ki.

TRI 50c calcium salt was observed to have a Ki of 10 nM.

Example 31

Preparation of Magnesium Salt of TRI 50C

TRI 50c (1.00 g, 1.90 mM) was dissolved in methanol (10 ml) and stirred at room temperature. To this solution was added magnesium methoxide (Mg(CH$_3$O)$_2$) in methanol (1.05 ml, 7.84 wt %). This solution was stirred for 2 hours at room temperature filtered and evacuated to 5 ml. Water (25 ml) was then added and the solution evacuated down to dryness to yield a white solid. This was dried over silica for 72 hours before being sent for microanalysis. Yield 760 mg.

$^1$H NMR 300 MHz, $\delta_H$(CD$_3$C(O)CD$_3$) 7.14-7.22 (20H, m), 6.90 (2H, m), 4.89 (4H, m, PhCH$_2$O, 4.38 (2H, m), 3.40 (2H, br s), 2.73-3.17 (20H, broad unresolved multiplets), 1.05-2.10 (16H, broad unresolved multiplets).

$^{13}$C NMR 75MHz $\delta_C$(CD$_3$C(O)CD$_3$) 206.56, 138.30, 130.76, 129.64, 129.31, 129.19, 129.09, 128.20, 128.04, 74.23, 73.55, 67.78, 58.76, 56.37, 56.03, 48.38, 47.87, 39.00, 25.42, 25.29.

FTIR (KBr disc) $v_{max}$ (cm$^{-1}$) 3331.3, 3031.4, 2935.3, 2876.9, 2341.9, 1956.1, 1711.6, 1639.9, 1534.3, 1498.1, 1453.0, 1255.3, 1115.3, 1084.6, 1027.6, 917.3, 748.9, 699.6, 594.9, 504.5, 467.8.

Example 32

Solubility of TRI50C

The UV/visible spectra of TRI50c resulting from the procedure of Example 5 and its solubility were obtained as described above in relation to the salts. The solubility of TRI50c when dissolved at 50 mg/ml was 8 mM (4 mg/ml).

Example 33

Analysis of Sodium. Calcium. Magnesium and Zinc Salts of (R.S.R) TRI 50C

The following salts were prepared using a boronate:metal stoichiometry of n:1, where n is the valency of the metal, using (R,S,R) TRI 50c of higher chiral purity than that used to prepare the salts described in Examples 8, 11, 14, 18, 21, 24 and 29.

A. Sodium Salt (Product of Example 9)

| Analytical data |
|---|
| HPLC or LC/MS: HPLC betabasic C18 Column, CH$_3$CN, Water<br>Estimated Purity: >95% by UV ($\lambda_{215\ nm}$) |

-continued

| Micro analysis: | | |
|---|---|---|
| | Calcd. | Found. |
| C: | 59.24 | 59.93 |
| H: | 6.44 | 6.47 |
| N: | 7.67 | 7.31 |
| Other: | | |
| B: | 1.98 | 1.91 |
| Na: | 4.20 | 3.81 |

| Physical Properties |
|---|
| Form: Amorphous solid |
| Colour: White |
| Melting Point: N/A |
| Solubility: Soluble in aqueous media |
| ca~50 mg/ml |
| $M_w$: 547.40 |

B. Calcium Salt (Product of Example 26)

| Analytical data |
|---|
| HPLC or LC/MS: HPLC betabasic C18 Column, $CH_3CN$, Water |
| Estimated Purity: >95% by UV ($\lambda_{215\ nm}$) |

| Micro analysis: | | |
|---|---|---|
| | Calcd. | Found. |
| C: | 59.27 | 55.08 |
| H: | 6.48 | 6.43 |
| N: | 7.71 | 7.08 |
| Other: | | |
| B: | 1.99 | 2.01 |
| Ca: | 3.68 | 3.65 |

| Physical Properties |
|---|
| Form: Amorphous solid |
| Colour: White |
| Melting Point: N/A |
| Solubility: Soluble in aqueous media |
| ca~4 mg/ml |
| $M_w$: 1088.89 |

C. Magnesium Salt (Product of Example 31)

| Analytical data |
|---|
| HPLC or LC/MS: HPLC betabasic C18 Column, $CH_3CN$, Water |
| Estimated Purity: >90% by UV ($\lambda_{215\ nm}$) |

| Micro analysis: | | |
|---|---|---|
| | Calcd. | Found. |
| C: | 60.44 | 57.25 |
| H: | 6.57 | 6.71 |
| N: | 7.83 | 7.45 |
| Other: | | |
| B: | 2.01 | 2.02 |
| Mg: | 2.26 | 2.12 |

-continued

| Physical Properties |
|---|
| Form: Amorphous solid |
| Colour: White |
| Melting Point: N/A |
| Solubility: Soluble in aqueous media |
| ca~7 mg/ml |
| $M_w$: 1073.12 |

D. Zinc Salt (Product of Example 15)

| Analytical data |
|---|
| HPLC or LC/MS: HPLC betabasic C18 Column, $CH_3CN$, Water |
| Estimated Purity: >95% by UV ($\lambda_{215\ nm}$) |

| Micro analysis: | | |
|---|---|---|
| | Calcd. | Found. |
| C: | 58.21 | 56.20 |
| H: | 6.33 | 6.33 |
| N: | 7.54 | 7.18 |
| Other: | | |
| B: | 1.94 | 1.84 |
| Zn: | 5.87 | 7.26 |

| Physical Properties |
|---|
| Form: Amorphous solid |
| Colour: White |
| Melting Point: N/A |
| Solubility: Soluble in aqueous media |
| ca~2 mg/ml |
| $M_w$: 1114.18 |

Notes:
The trigonal formula of the acid boronate is used in the calculated microanalyses. It is believed that a lower sodium salt solubility is reported in example 11 because the salt tested in example 11 had lower chiral purity.

Conclusion

The zinc, calcium and magnesium salts have all been prepared with a stoichiometry of one metal ion to two molecules of TRI 50c. The values found for the calcium and magnesium salts are close to and thus consistent with those calculated for this 1:2 stoichiometry. For the zinc salt an excess of zinc was found; nonetheless, the zinc salt comprises a significant proportion of acid boronate. The sodium salt has been prepared with a stoichiometry of one metal ion to one molecule of TRI 50c. The value found for the sodium salt is close to and thus consistent with that calculated for this 1:1 stoichiometry.

Example 34

Stability

An assay of TRI 50c and its sodium and lysine salts before and after drying.

1. Tabulated Results

TABLE 1

| Compound | Amount [µg/mL] | Purity (% area) |
| --- | --- | --- |
| TRI 50c dry | 1000.0 | 82.00 |
| TRI 50c non-dried | 947.3 | 85.54 |
| TRI 50c Na salt dry | 1024 | 98.81 |
| TRI 50c Na salt non-dried | 1005.8 | 98.61 |
| TRI 50c Lys salt dry | 813.3 | 90.17 |
| TRI 50c Lys salt non-dried | 809.8 | 92.25 |

The purity of the acid was lowered by the drying process but the purity of the salts was less affected; the purity of the sodium salt was not significantly reduced. Large differences in response factors will reduce the actual impurity levels, however.

2. Analytical Procedure

2.1 Sample Preparation

TRI 50c and its Na, Li and Lys salts were weighed into HPLC vials and stored in a desiccator over phosphorus pentoxide for 1 week. For sample analysis, 5 mg of dried and non-dried material was weighed in a 5 mL volumetric flask and dissolved in 1 mL acetonitrile and filled up with demineralised water to 5 mL.

3. Data Evaluation

The quantitative evaluation was performed using an HPLC-PDA method.

4. Analytical Parameters

| 4.1 Equipment and software | |
| --- | --- |
| Autosampler | Waters Alliance 2795 |
| Pump | Waters Alliance 2795 |
| Column oven | Waters Alliance 2795 |
| Detection | Waters 996 diode array, MS-ZQ 2000 single quad |
| Software version | Waters Millennium Release 4.0 |
| 4.2 Stationary phase | |
| Analytical Column ID | S71 |
| Material | X-Terra™ MS $C_{18}$, 5 µm |
| Supplier | Waters, Eschborn, Germany |
| Dimensions | 150 mm × 2.1 mm (length, internal diameter) |
| 4.3 Mobile phase | |
| Aqueous phase: | A: $H_2O$ + 0.1% |
| Organic phase: | C: ACN |

| Gradient conditions: | | | |
| --- | --- | --- | --- |
| Time | Flow | % A | % C |
| 0.00 | 0.5 | 90 | 10 |
| 27.0 | 0.5 | 10 | 90 |
| 27.1 | 0.5 | 90 | 10 |
| 30.0 | 0.5 | 90 | 10 |

This example indicates that the salts of the disclosure, particularly the metal salts, e.g. alkali metal salts, are more stable than the acids, notably TRI 50c.

Example 35

In-Vitro Assay as Thrombin Inhibitor of Magnesium Salt of TRI 50C

Thrombin Amidolytic Assay

TRI 50c magnesium salt (TRI 1405) was tested in a thrombin amidolytic assay.

Reagents:

Assay Buffer:
100 mM Na phosphate
200 mM NaCl (11.688 g/l)
0.5% PEG 6000 (5 g/l)
0.02% Na azide
pH 7.5

Chromogenic substrate S2238 dissolved to 4 mM (25 mg+10 ml) in water. Diluted to 50 µM with assay buffer for use in assay at 5 µM. (S2238 is H-D-Phe-Pip-Arg-pNA).

Thrombin obtained from HTI, via Cambridge Bioscience, and aliquoted at 1 mg/ml with assay buffer. Dilute to 100 ng/ml with assay buffer and then a further 1 in 3 for use in the assay.

Assay:
110 µl assay buffer
50 µl 5 µg/ml thrombin
20 µl vehicle or compound solution
5 min at 37° C.
20 µl 50 µM S2238
Read at 405 nm at 37° C. for 10 minutes and record Vmax Results:
The results are presented in FIG. 1.

Discussion:
In this assay the magnesium salt of TRI 50c shows the same activity as TRI 50b as an external control.

Example 36

TRI 50B Inhibition of Platelet Procoagulant Activity

Platelet pro-coagulant activity may be observed as the increase, in rate of activation of prothrombin by factor Xa in the presence of factor Va upon the addition of platelets pretreated with thrombin, caused by thrombin alone, collagen alone or a mixture of thrombin and collagen. This property is due to an increase in anionic phospholipid on the surface of the platelet with concomitant release of microvesicle from the surface. This is an essential physiological reaction and people whose platelets have reduced ability to generate procoagulant activity (Scott syndrome) show an increased tendency for bleeding.

Method:

Washed platelets were treated with either 1.15 nM thrombin, 23 µg/ml collagen or a mixture of both at the same concentration at 37° C. TRI 50b was added either for 1 minute prior to the addition of activator or immediately after the incubation with activator. Platelet procoagulant activity was determined as described previously (Goodwin C A et al, *Biochem J.* 1995 8, 308: 15-21). TRI 50b proved to be a potent inhibitor of platelet procoagulant activity with $IC_{50}$'s as summarised below:

Table 2: Influence of TRI 50b on the induction of platelet procoagulant activity by various agonists:

TABLE 2

| Agonist | Fold acceleration without TRI 50b | IC50 plus pre-incubation (nM) | IC50 without incubation (nM) |
|---|---|---|---|
| Thrombin | 30 | 8 | 3000 |
| Collagen | 45 | 200 | 300 |
| Thrombin/Collagen | 110 | 3 | 80 |

Table 2 records, for example, that when platelets were treated with thrombin they caused a 30-fold acceleration of the rate of activation of prothrombin in comparison with control platelets. Treatment with TRI 50 reduced such acceleration by half at the various TRI 50 concentration levels given. The significant potency of TRI 50 is evidenced by the fact that the $IC_{50}$ values are in the nanomolar range.

TRI 50b does not have an effect on ADP, collagen or epinephrine induced aggregation of washed platelets.

Example 37

Rabbit Extracorporeal Shunt Model

Introduction

The technique describes an animal model in which a platelet rich thrombus is produced. The activity of TRI 50b and heparin are compared.

The carotid artery and jugular vein of anaesthetised rabbits were used to create an extracorporeal circuit containing a suspended foreign surface (silk thread). Thrombus deposition is initiated by creation of high sheer stress turbulent arterial blood flow, platelet activation, followed by coagulation in the presence of thrombogenic surfaces. Histopathological studies have shown that the thrombus is platelet rich.

Materials and Methods

Animals:

NZW rabbits (males 2.5-3.5 kg) were used. The animals were allowed food and water up to the induction of anaesthesia.

Anaesthesia:

Animals were premedicated with fontanel/fluanisone (Hypnorm) 0.15 ml total by intramuscular injection. General anaesthesia was induced with methohexitone (10 mg/ml) to effect, followed by endotracheal intubation. Anaesthesia was maintained with isoflurane (1-2.0%) carried in oxygen/nitrous oxide.

Surgical Preparation:

The animals were placed in dorsal recumbency and the ventral cervical region prepared for surgery. The left carotid artery and right jugular vein were exposed. The artery was cannulated with a large Portex® catheter (yellow gauge), cut to a suitable length. The vein was cannulated with a Silastic® catheter. The shunt comprised of a 5 cm length of 'auto analyser' line (purple/white gauge). Joins to the shunt on the arterial side were made with intermediate size Silastic® tubing. The shunt was filled with saline before exposure to the circulation. The right femoral artery was cannulated for the measurement of blood pressure.

Thread Preparation and Insertion:

The central section of the shunt contained a thread 3 centimetres in length. This consisted of 000 gauge Gutterman sewing silk so as to give four strands with a single knot at the end. (The knot section was outside the shunt).

Blood Flow

Blood flow velocity was determined by use of 'Doppler' probes (Crystal Biotech). A silastic probe was positioned over the carotid artery at the point of insertion of the arterial catheter. Flow was recorded on a chart recorder using heat sensitive paper.

TABLE 3

| TREATMENT | DOSE | THROMBUS WEIGHT AFTER 20 minute run | ANTITHROMBOTIC ACTIVITY |
|---|---|---|---|
| Control | N/A | 22.4 ± 2.2 mg (n = 5) | |
| TRI 50b | 10 mg/kg iv | 9.78 ± 1.9 mg (n = 5) | Active |
| | 3.0 mg/kg iv | 15.3 ± 2.2 mg (n = 5) | Active |
| HEPARIN | 100 u/kg iv | 22.9 ± 1.65 mg (n = 4) | Inactive |
| | 300 u/kg iv | 10.5 ± 1.4 mg (n = 4) | Active (Severe bleeding) |

Discussion

Table 3 shows that, under high arterial shear conditions, a TRI 50b dose of 3 mg/kg to 10 mg/kg iv significantly inhibits thrombus formation without bleeding, whereas a heparin dose within the normal clinical range for treating venous thrombosis (100 u/kg iv heparin) was ineffective. The higher dose of heparin, though active, caused severe bleeding. These results, which show TRI 50b effectively inhibiting arterial thrombosis without causing bleeding, are consistent with TRI 50b inhibiting platelet procoagulant activity. In contrast, the thrombin inhibitor heparin, when administered at an approximately equi-effective dose (in terms of inhibition of arterial thrombosis), produced the severe bleeding normal when thrombin inhibitors are used to treat arterial thrombosis.

Example 38

Comparison of Bleeding Times

The aim of the study was to compare the bleeding times of heparin with TRI 50b in a suitable model. It is accepted that heparin is a poor inhibitor of platelet procoagulant activity (*J. Biol. Chem.* Oct. 10, 1978; 253(19):6908-16; Miletich J P, Jackson C M, Majerus PW1: *J. Clin. Invest.* 1983 May; 71(5):1383-91).

Bleeding times were determined in a rat tail bleeding model following intravenous administration of heparin and TRI 50b. The doses employed were chosen on the basis of their efficacy in the rat Wessler and dynamic models and were as follows:

TRI 50b: 5 and 10 mg/kg

Heparin: 100 units/kg

Materials and Methods

Anaesthesia

Rats were anaesthetised with sodium pentabarbitone at 60 mg/kg (2.0 ml/kg of 30 mg/ml solution by ip. injection). Supplemental anaesthetic was given ip. as required.

Surgical Preparation

A jugular vein was cannulated for the administration of test compound. The trachea was also cannulated with a suitable cannula and the animals allowed to breathe 'room air' spontaneously.

Compound administration

These were given in the appropriate vehicle at 1.0 ml/kg intravenously. Heparin was administered in saline, whilst TRI 50b was dissolved in ethanol, and then the resultant solution added to water for injection (1 part ethanol to 5 parts water).

Technique

Two minutes following compound administration the distal 2 mm of the animal's tail was sectioned with a new scalpel blade and the tail immersed in warm saline (37° C.) contained in a standard 'universal' container, so that the blood stream was clearly visible. The bleeding time recording was started immediately following transection until the cessation of blood flow from the tip of the tail. A period of 30 seconds was allowed after the blood flow from the tail had stopped to ensure that bleeding did not re-commence, if bleeding did start again the recording time was continued for up to a maximum of 45 minutes.

Results

Table 4 gives a summary of the bleeding results and shows the increases above base line values.

TABLE 4

Summary table of bleeding results

| Treatment | Bleeding time min (±SEM[†]) |
|---|---|
| Saline | 5.1 ± 0.6 |
| Heparin 100 u/kg iv | >40* |
| TRI 50b 5 mg/kg iv | 11.3 ± 1.2 |
| TRI 50b 10 mg/kg iv | 30.4 ± 5.2 |

*Severe bleeding in all animals, with no cessation after 40 minutes.
[†]SEM = standard error of the mean Discussion The results show that TRI 50b was superior to heparin (produced less bleeding) at all doses. It should be noted that when 100 u/kg heparin is compared with 5 mg/kg TRI 50b, heparin-treated animals bled more extensively than those receiving TRI 50b; it was previously established (Example 25) that heparin at a dose of 100 u/kg is a less effective inhibitor of arterial thrombosis than TRI 50b at a dose of 3.0 mg/kg. Heparin is primarily a thrombin inhibitor and a poor inhibitor of platelet procoagulant activity; the results are therefore consistent with TRI 50b exerting anti-coagulant activity by inhibition of platelet coagulant activity in addition to thrombin inhibiting activity.

Example 39

TRI 50B as a Prodrug for TRI 50C: Pharmacokinetics and Absorption

Materials and Methods

Animals

Rats, body weight circa 250-300 g were used. The animals were fasted only on the day of use for the iv stage.

TABLE 5

| | iv phase | |
|---|---|---|
| Treatment | Dose mg/kg iv | n |
| TRI 50b | 1.0 mg/kg | 3 |
| TRI 50c | 1.0 mg/kg | 3 |

Dose

Formulation (TRI 50b/TRI 50c)

These were dosed in a formulation prepared as follows: 48 mg/ml of TRI 50b is dissolved in ethanol: PEG 300 (2:3 vol: vol). Just before administration, 5 volumes of this solution is mixed with 3 volumes of 5% kollidon 17 8F.

i.v. Phase

Both compounds were given at a dose of 1.0 mg/kg iv.

The compounds were dosed in a PEG/ethanol/kollidon formulation which was prepared immediately before, as described immediately under the heading "Dose": Stock 15.0 mg/ml. This was dosed at 1.33 ml/kg (equivalent to 30 mg/kg).

Blood Sampling

A pre dose sample was taken followed by: 0, 2, 5, 10, 20, 30, 40, 60 and 90 minutes post dose.

Plasma

This was obtained by centrifugation (3000 RPM for 10 min) and stored at −20° C. prior to analysis.

Results

Pharmacokinetic Analysis

TABLE 6

| i.v. pharmacokinetic data | | |
|---|---|---|
| | TRI 50b | TRI 50c |
| Elimination half life: minutes | 35 minutes | 36.6 minutes |
| Area under curve | 1.68 | 1.48 |
| Mean Residence Time | 46 minutes | 45 minutes |
| Clearance: ml/min/kg | 10 | 11.3 |
| Volume Distribution Liters/kg | 0.5 | 0.59 |
| Max Plasma Concentration (observed) | 2.24 | 2.35 |

Figure 2:
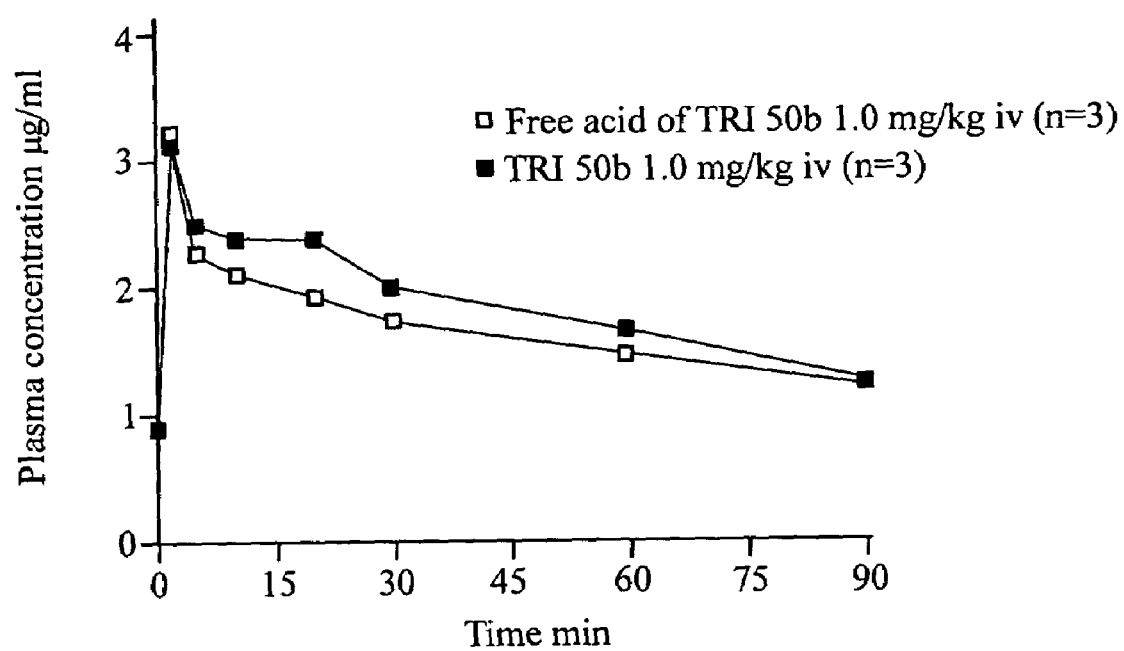
FIG. 2 is a plot referred to in Example 39, showing intravenous phase clearance and kinetics following a single dose of TRI 50b or TRI 50c.

The following results are represented in FIG. 2:

FIG. 2: intravenous phase clearance and kinetics following a single dose of TRI 50b or its free acid (TRI 50c). The figure shows the observed assay data.

Conclusion

The i.v. kinetics were similar for both TRI 50b and TRI 50c. The data are consistent with TRI 50b being rapidly hydrolysed in plasma to TRI 50c and with TRI 50c being the active principle.

The results of examples 36 to 39 indicate that administration of TRI 50c as a salt will provide a way to treat arterial thrombosis and/or venous thrombosis.

Example 40

Intravenous Administration of TRI 50C Sodium Salt

The pharmacokinetics (PK) and pharmacodynamics (PD) of TRI 50c sodium salt were studied in beagle dogs following intravenous administration.

The PD was measured as thrombin time and APTT using an automated coagulometer. Plasma concentrations were measured using an LCMS /MS method. TRI 50c monosodium salt (108.8 g) was dissolved in 0.9% sodium chloride (100 ml) and dosed i.v. at 1.0 mg/kg (1.0 ml/kg over 30 seconds). Blood samples were taken into 3.8% tri-sodium citrate (1+8) at pre dose, 2, 5, 10, 20, 30, minutes post dose and then at 1, 2, 3, 4, 6, 8, 12 and 24 hours post dose. Plasma was prepared by centrifugation and frozen at minus 20° C. pending analysis.

Results

The sodium salt was tolerated well with no adverse events for the total duration of the study.

Male and female dogs responded similarly with a pharmacodynamic C max: at 2 minutes (thrombin time of 154 seconds raised from a base line of 14.3 seconds). Thrombin time was 26 seconds at one hour post dose.

There was an exceptionally good therapeutic ratio between the APTT and thrombin clotting time in dogs receiving the sodium salt at a dose of 1.0 mg/kg i.v. Thrombin clotting time was elevated 10.8 times above base line (154.4 seconds from 14.3 seconds) two minutes following dosing, compared to only 1.3 times elevation in the APTT (19 seconds to 25 seconds post dose).

Example 41

Human Clinical Studies

In human clinical volunteer studies with doses of up to 2.5 mg/kg i.v. (dosages which significantly prolong the thrombin clotting time), TRI 50b had no effect on Simplate bleeding time (i.e. bleeding time measured using a Simplate® bleeding time device).

It will be appreciated from the foregoing that the disclosure provides boronic acid salts useful for pharmaceutical purposes and which feature one or more of the following attributes: (1) improved hydrolytic stability; (2) improved stability against deboronation; and (3), in any event, not suggested by the prior art.

The selection of active ingredient for a pharmaceutical composition is a complex task, which requires consideration not only of biological properties (including bioavailability) but also of physicochemical properties desirable for processing, formulation and storage. Bioavailability itself is dependent on various factors, often including in vivo stability, solvation properties and absorption properties, each in turn potentially dependent on multiple physical, chemical and/or biological behaviours.

The present disclosure includes the subject matter of the following paragraphs:

1. A parenteral pharmaceutical formulation comprising a pharmaceutically acceptable base addition salt of a boronic acid of formula (I):

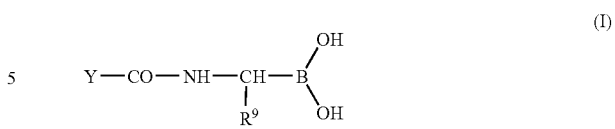

wherein
Y comprises a hydrophobic moiety which, together with the aminoboronic acid residue —NHCH($R^9$)—B(OH)$_2$, has affinity for the substrate binding site of thrombin; and $R^9$ is a straight chain alkyl group interrupted by one or more ether linkages and in which the total number of oxygen and carbon atoms is 3, 4, 5 or 6 or $R^9$ is —(CH$_2$)$_m$—W where m is from 2, 3, 4 or 5 and W is —OH or halogen (F, Cl, Br or I).

2. A formulation of paragraph 1 wherein $R^9$ is an alkoxyalkyl group.

3. A formulation of paragraph 1 or paragraph 2 wherein YCO— comprises an amino acid which binds to the S2 subsite of thrombin, the amino acid being N-terminally linked to a moiety which binds the S3 subsite of thrombin.

4. A formulation of paragraph 1 or paragraph 2 wherein Y is an optionally N-terminally protected dipeptide which binds to the S3 and S2 binding sites of thrombin and the peptide linkages in the acid are optionally and independently N-substituted by a $C_1$-$C_{13}$ hydrocarbyl optionally containing in-chain or in-ring nitrogen, oxygen or sulfur and optionally substituted by a substituent selected from halo, hydroxy and trifluoromethyl.

5. A formulation of paragraph 4 wherein said dipeptide is N-terminally protected and all the peptide linkages in the acid are unsubstituted.

6. A formulation of paragraph 4 or paragraph 5 wherein the S3-binding amino acid residue is of R configuration, the S2-binding residue is of S configuration, and the fragment —NHCH($R^9$)—B(OH) is of R configuration.

7. A formulation of any of paragraphs 1 to 6 wherein the boronic add has a Ki for thrombin of about 100 nM or less.

8. A formulation of paragraph 7 wherein the boronic acid has a Ki for thrombin of about 20 nM or less.

9. A formulation in parenteral dosage form of a pharmaceutically acceptable base addition salt of a boronic acid of formula (II):

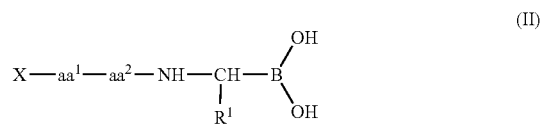

where:
X is H (to form NH$_2$) or an amino-protecting group;
aa$^1$ is an amino acid having a hydrocarbyl side chain containing no more than 20 carbon atoms and comprising at least one cyclic group having up to 13 carbon atoms;
aa$^2$ is an imino acid having from 4 to 6 ring members;
$R^1$ is a group of the formula —(CH$_2$)$_s$-Z, where s is 2, 3 or 4 and Z is —OH, —OMe, —OEt or halogen (F, Cl, Br or I).

10. A formulation of paragraph 9 wherein $aa^1$ is selected from Phe, Dpa and wholly or partially hydrogenated analogues thereof.

11. A formulation of paragraph 9 wherein $aa^1$ is selected from Dpa, Phe, Dcha and Cha.

12. A formulation of any of paragraphs 9 to 11 wherein $aa^1$ is of R-configuration.

13. A formulation of paragraph 9 wherein $aa^1$ is (R)-Phe or (R)-Dpa.

14. A formulation of paragraph 9 wherein $aa^1$ is (R)-Phe.

15. A formulation of any of paragraphs 9 to 15 wherein $aa^2$ is a residue of an imino acid of formula (IV)

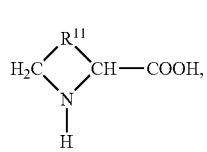

(IV)

where $R^{11}$ is —$CH_2$—, —$CH_2$—$CH_2$—, —S—$CH_2$—, —S—$C(CH_3)_2$— or —$CH_2$—$CH_2$—$CH_2$—, which group, when the ring is 5- or 6- membered, is optionally substituted at one or more —$CH_2$— groups by from 1 to 3 $C_1$-$C_3$ alkyl groups.

16. A formulation of paragraph 15 wherein $aa^2$ is of S-configuration.

17. A formulation of paragraph 15 wherein $aa^2$ is an (S)-proline residue.

18. A formulation of paragraph 9, wherein $aa^1$-$aa^2$ is (R)-Phe-(S)-Pro.

19. A formulation of any of paragraphs 9 to 18 wherein $R^1$ is 2-bromoethyl, 2-chloroethyl, 2-methoxyethyl, 3-bromopropyl, 3-chloropropyl or 3-methoxypropyl.

20. A formulation of any of paragraphs 9 to 18 wherein $R^1$ is 3-methoxypropyl.

21. A formulation of any of paragraphs 9 to 20 where X is $R^6$—$(CH_2)_p$—C(O)—, $R^6$—$(CH_2)_p$—$S(O)_2$—, $R^6$—$(CH_2)_p$—NH—C(O)— or $R^6$—$(CH_2)_p$—O—C(O)— wherein p is 0, 1, 2, 3, 4, 5 or 6 and $R^6$ is H or a 5 to 13-membered cyclic group optionally substituted by 1, 2 or 3 substituents selected from halogen, amino, nitro, hydroxy, a $C_5$-$C_6$ cyclic group, $C_1$-$C_4$ alkyl and $C_{1-C4}$ alkyl containing, and/or linked to the cyclic group through, an in-chain O, the aforesaid alkyl groups optionally being substituted by a substituent selected from halogen, amino, nitro, hydroxy and a $C_5$-$C_6$ cyclic group.

22. A formulation of paragraph 21 wherein said 5 to 13-membered cyclic group is aromatic or heteroaromatic.

23. A formulation of paragraph 21 wherein said 5 to 13-membered cyclic group is phenyl or a 6-membered heteroaromatic group.

24. A formulation of any of paragraphs 9 to 20 wherein X is $R^6$—$(CH_2)_p$—C(O)— or $R^6$—$(CH_2)_p$—O—C(O)— and p is 0 or 1.

25. A formulation of any of paragraphs 9 to 20 wherein X is benzyloxycarbonyl.

26. A formulation of paragraph 9 wherein the boronic acid is of formula (VIII):

X-(R)-Phe-(S)-Pro-(R)Mpg-B(OH)$_2$   (VIII).

27. A formulation of any of paragraphs 1 to 26 wherein the salt comprises boronate ions derived from the boronic acid and monovalent counter-ions.

28. A formulation of any of paragraphs 1 to 26 which comprises a salt of the peptide boronic acid with an alkali metal or a strongly basic organic nitrogen-containing compound.

29. A formulation of paragraph 28 wherein the strongly basic organic nitrogen-containing compound is a guanidine, a guanidine analogue or an amine.

30. A formulation of any of paragraphs 1 to 27 wherein the salt is a salt of the boronic acid with a metal.

31. A formulation of any of paragraphs 1 to 26 which comprises a salt of the boronic acid with an alkali metal, an aminosugar, a guanidine or an amine of formula (XI):

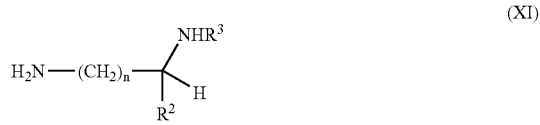

(XI)

where n is from 1 to 6, $R^2$ is H, carboxylate or derivatised carboxylate, $R^3$ is H, $C_1$-$C_4$ alkyl or a residue of a natural or unnatural amino acid.

32. A formulation of any of paragraphs 1 to 26 which comprises a salt of the boronic acid with a guanidine or with an amine of formula (IX):

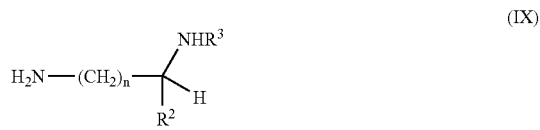

(IX)

where n is from 1 to 6, $R^2$ is H, carboxylate or derivatised carboxylate, $R^3$ is H, $C_1$-$C_4$ alkyl or a residue of a natural or unnatural amino acid.

33. A formulation of paragraph 32 which comprises a guanidine salt of the boronic acid.

34. A formulation of paragraph 33 which comprises a salt of the boronic acid with L-arginine or an L-arginine analogue.

35. A formulation of paragraph 34 wherein the L-arginine analogue is D-arginine, or the D- or L-isomers of homoarginine, agmatine [(4-aminobutyl) guanidine], NG-nitro-L-arginine methyl ester, or a 2-amino pyrimidines.

36. A formulation of paragraph 33 which comprises a salt of the boronic acid with a guanidine of formula (VII)

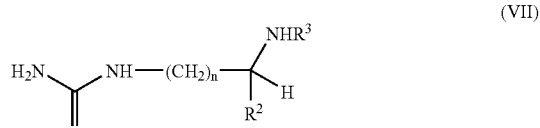

(VII)

where n is from 1 to 6, $R^2$ is H, carboxylate or derivatised carboxylate, $R^3$ is H, $C_1$-$C_4$ alkyl or a residue of a natural or unnatural amino acid.

37. A formulation of paragraph 36, wherein n is 2, 3 or 4.

38. A formulation of paragraph 36 or paragraph 37 where the derivatised carboxylate forms a $C_1$-$C_4$ alkyl ester or amide.

39. A formulation of any of paragraphs 36 to 38 wherein the compound of formula (VII) is of L-configuration.

40. A formulation of paragraph 33 which comprises an L-arginine salt of the peptide boronic acid.

41. A formulation of paragraph 32 which comprises a salt of the boronic acid with an amine of formula (IX).

42. A formulation of paragraph 41, wherein n is 2, 3 or 4.

43. A formulation of paragraph 41 or paragraph 42 where the derivatised carboxylate forms a $C_1$-$C_4$ alkyl ester or amide.

44. A formulation of any of paragraphs 41 to 43 wherein the amine of formula (IX) is of L-configuration.

45. A formulation of paragraph 41 which comprises an L-lysine salt of the boronic acid.

46. A formulation of any of paragraphs 1 to 26 which comprises an alkali metal salt of the boronic add.

47. A formulation of paragraph 46 wherein the alkali metal is potassium.

48. A formulation of paragraph 46 wherein the alkali metal is sodium.

49. A formulation of paragraph 46 wherein the alkali metal is lithium.

50. A formulation of any of paragraphs 1 to 26 which comprises an aminosugar salt of the boronic acid.

51. A formulation of paragraph 50 wherein the aminosugar is a ring-opened sugar.

52. A formulation of paragraph 51 wherein the aminosugar is a glucamine.

53. A formulation of paragraph 50 wherein the aminosugar is a cyclic aminosugar.

54. A formulation of any of paragraphs 50 to 53 wherein the aminosugar is N-unsubstituted.

55. A formulation of any of paragraphs 50 to 53 wherein the aminosugar is N-substituted by one or two substituents.

56. A formulation of paragraph 55 wherein the or each substituent is a hydrocarbyl group.

57. A formulation of paragraph 55 wherein the or each substituent is selected from the group consisting of alkyl and aryl moieties.

58. A formulation of paragraph 57 wherein the or each substituent is selected from the group consisting of $C_1$, $C_2$, $C_3$, $C_4$, $C_5$, $C_6$, $C_7$ and $C_8$ alkyl groups 59. A formulation of any of paragraphs 55 to 58 wherein there is a single N-substituent.

60. A formulation of paragraph 50 wherein the glucamine is N-methyl-D-glucamine.

61. A formulation of any of paragraphs 1 to 60 which comprises boronate ions derived from the peptide boronic add and has a stoichiometry consistent with the boronate ions carrying a single negative charge.

62. A formulation of any of paragraphs 1 to 60 wherein the salt consists essentially of acid salt (that is, wherein one B—OH group remains protonated).

63. A formulation of any of paragraphs 1 to 62 wherein the salt comprises a boronate ion derived from the peptide boronic acid and a counter-ion and wherein the salt consists essentially of a salt having a single type of counter-ion.

64. A product for use as a parenteral pharmaceutical, comprising a salt of any of paragraphs 1 to 63.

65. A pharmaceutical formulation in parenteral dosage form comprising a salt of any of paragraphs 1 to 63 and a pharmaceutically acceptable diluent, excipient or carrier.

66. A pharmaceutical formulation of paragraph 65 which is adapted for intravenous administration.

67. A pharmaceutical formulation of paragraph 65 which is adapted for subcutaneous administration.

68. A method of inhibiting thrombin in the treatment of disease comprising parenterally administering to a mammal a therapeutically effective amount of an active agent selected from the group consisting of a salt as defined in any of paragraphs 1 to 63.

69. The use of a salt as defined in any of paragraphs 1 to 63 for the manufacture of a parenteral medicament for treating thrombosis.

70. A method of treating venous and/or arterial thrombosis by prophylaxis or therapy, comprising parenterally administering to a mammal suffering from, or at risk of suffering from, arterial thrombosis a therapeutically effective amount of a product selected form the salts defined any of paragraphs 1 to 63.

71. A method of paragraph 70 wherein the disease is an acute coronary syndrome.

72. A method of paragraph 70 wherein the disease is acute myocardial infarction.

73. A method of paragraph 70 wherein the disease is a venous thromboembolic event, selected from the group consisting of deep vein thrombosis and pulmonary embolism.

74. A method for preventing thrombosis in a haemodialysis circuit of a patient, comprising parenterally administering to the patient a therapeutically effective amount of a product selected from the salts defined any of paragraphs 1 to 63.

75. A method for preventing a cardiovascular event in a patient with end stage renal disease, comprising parenterally administering to the patient a therapeutically effective amount of a product selected from the salts defined any of paragraphs 1 to 63.

76. A method for preventing venous thromboembolic events in a patient receiving chemotherapy through an indwelling catheter, comprising administering to the patient a therapeutically effective amount of a product selected from the salts defined any of paragraphs 1 to 63.

77. A method for preventing thromboembolic events in a patient undergoing a lower limb arterial reconstructive procedure, comprising parenterally administering to the patient a therapeutically effective amount of a product selected from the salts defined any of paragraphs 1 to 63.

78. A method of inhibiting platelet procoagulant activity, comprising parenterally administering to a mammal at risk of, or suffering from, arterial thrombosis a therapeutically effective amount of a product selected from the salts defined any of paragraphs 1 to 63.

79. A method of paragraph 78 wherein the disease is an acute coronary syndrome.

80. A method of treating by way of therapy or prophylaxis an arterial disease selected from acute coronary syndromes, cerebrovascular thrombosis, peripheral arterial occlusion and arterial thrombosis resulting from atrial fibrillation, valvular heart disease, arterio-venous shunts, indwelling catheters or coronary stents, comprising parenterally administering to a mammal a therapeutically effective amount of a product selected from the salts defined any of paragraphs 1 to 63.

81. A method of paragraph 80wherein the disease is an acute coronary syndrome.

82. The use of a salt of any of paragraphs 1 to 63 for the manufacture of a parenteral medicament for a treatment recited in any of paragraphs 76 to 81.

83. A parenteral pharmaceutical formulation comprising a combination of (i) a salt of any of paragraphs 1 to 63 and (ii) a further pharmaceutically active agent.

84. A parenteral pharmaceutical formulation comprising a combination of (i) a salt of any of paragraphs 1 to 63 and (ii) another cardiovascular treatment agent.

85. A formulation of paragraph 84 wherein the other cardiovascular treatment agent comprises a lipid-lowering drug, a fibrate, niacin, a statin, a CETP inhibitor, a bile acid sequestrant, an anti-oxidant, a IIb/IIIa antagonist, an aldosterone inhibitor, an A2 antagonist, an A3 agonist, a beta-blocker, acetylsalicylic acid, a loop diuretic, an ace inhibitor, an antithrombotic agent with a different mechanism of action, an antiplatelet agent, a thromboxane receptor and/or synthetase inhibitor, a fibrinogen receptor antagonist, a prostacyclin mimetic, a phosphodiesterase inhibitor, an ADP-receptor ($P_2T$) antagonist, a thrombolytic, a cardio-protectant or a COX-2 inhibitor.

86. The use of a salt of any of paragraphs 1 to 63 for the manufacture of a parenteral medicament for treating, for example preventing, a cardiovascular disorder in co-administration with another cardiovascular treatment agent.

87. A method for recovering from ether solution an ester of a boronic acid as defined in any of paragraphs 1 to 26, comprising dissolving diethanolamine in the solution, allowing or causing a precipitate to form and recovering the precipitate.

88. A method of paragraph 79 wherein the ester is a pinacol ester.

89. The method of paragraph 79 or paragraph 80 which further comprises converting, suitably hydrolysing, the precipitated material into the free organoboronic acid.

90. The method of paragraph 89, wherein the conversion comprises contacting the precipitated material with an aqueous acid or base.

91. The method of paragraph 90, wherein the precipitated material is contacted with a concentrated strong inorganic add.

92. A method for making a boronic add as defined in any of paragraphs 1 to 26, comprising converting a diolamine reaction product thereof to the add, suitably hydrolysing the diolamine reaction product to form the acid.

93. The method of paragraph 92, wherein the conversion is carried out as recited in paragraph 82 or paragraph 83.

94. The method of any of paragraphs 87 to 93, which further comprises converting the organoboronic acid to a salt thereof.

95. The method of paragraph 94, wherein the salt is as defined in any of paragraphs 2 to 63.

96. The method of paragraph 94 or paragraph 95, which further comprises formulating the salt into a pharmaceutical composition.

97. A product obtainable by (having the characteristics of a product obtained by) reacting in diethylether solution a pinacol ester of a compound of Formula (VIII) as defined in paragraph 26 and diethanolamine.

98. A composition of matter comprising:
(i) a species of formula (XII)

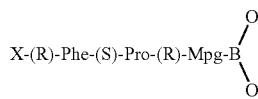

(XII)

wherein X is H or an amino protecting group, the boron atom is optionally coordinated additionally with a nitrogen atom, and the valency status of the terminal oxygens is open (they may be attached to a second covalent bond, be ionised as —O—, or have some other, for example intermediate, status); and, in bonding association therewith
(ii) a species of formula (XIII)

wherein the valency status of the nitrogen atom and the two oxygen atoms is open.

99. A composition of paragraph 98, wherein the terminal oxygen atoms of the species of formula (XII) and the oxygen atoms of the species of formula (XIII) are the same oxygen atoms, i.e. the species of formula (XIII) forms a diol ester with the species of formula (XII).

100. The use of a boronic add as defined in any of paragraphs 1 to 26 as an intermediate to make a salt of any of paragraphs 1 to 63.

101. A method of preparing a salt of any of paragraphs 1 to 63, comprising contacting a boronic acid as defined in any of paragraphs 1 to 26 with a base capable of making such a salt.

102. A peptide boronic add of formula (II) as defined in any of paragraphs 9 to 26 when of GLP or GMP quality, or when in compliance with GLP (good laboratory practice) or GMP (good manufacturing practice).

103. A composition of matter which is sterile or acceptable for pharmaceutical use, or both, and comprises a peptide boronic acid of formula (II) as defined in any of paragraphs 9 to 26.

104. A composition of matter of paragraph 103 which is in particulate form.

105. A composition of paragraph 103 which is in the form of a liquid, solution or dispersion.

106. An isolated compound which is a peptide boronic acid of formula (VIII):

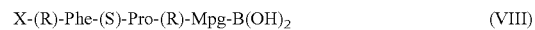

wherein X is H (to form $NH_2$) or an amino-protecting group.

107. A compound of paragraph 106 wherein X is benzyloxycarbonyl.

108. A particulate composition comprising a peptide boronic acid of formula (VIII) as defined in paragraph 106 or paragraph 107.

109. A composition of paragraph 108 consisting predominantly of the peptide boronic acid.

110. A composition of paragraph 109 wherein the peptide boronic acid forms at least 75% by weight of the composition.

111. A composition of paragraph 110 wherein the peptide boronic acid forms at least 85% by weight of the composition.

112. A composition of paragraph 111 wherein the peptide boronic acid forms at least 95% by weight of the composition.

113. A composition of any of paragraphs 108 to 112 which is sterile.

114. A composition of any of paragraphs 108 to 113 wherein the peptide boronic add is in finely divided form.

115. A liquid composition consisting of, or consisting essentially of, a peptide boronic acid of formula (II) as defined in any of paragraphs 9 to 26 and liquid vehicle in which it is dissolved or suspended.

116. A liquid composition of paragraph 115 wherein the liquid vehicle is an aqueous medium, e.g. water.

117. A liquid composition of paragraph 115 wherein the liquid vehicle is an alcohol, for example methanol, ethanol, isopropanol or another propanol, another alkanol or a mixture of the aforegoing.

118. A liquid composition of any of paragraphs 115 to 117 which is sterile.

119. A parenteral medicament comprising a salt of a boronic acid which is a selective thrombin inhibitor and has a neutral aminoboronic acid residue capable of binding to the thrombin S1 subsite linked through a peptide linkage to a hydrophobic moiety capable of binding to the thrombin S2 and S3 subsites, the salt comprising a cation having a valency n and having an observed stoichiometry consistent with a notional stoichiometry (boronic acid:cation) of n:1.

120. A medicament of paragraph 119 wherein the boronic acid has a Ki for thrombin of about 100 nM or less.

121. A medicament of paragraph 119 wherein the boronic acid has a Ki for thrombin of about 20 nM or less.

122. A parenteral medicament comprising a sodium salt of Cbz-(R)-Phe-(S)-Pro-(R)-Mpg-B(OH)$_2$.

123. A method of stabilising an organoboronic acid, comprising providing it in the form of a salt thereof.

124. A method of formulating an organoboronic acid drug to increase the stability of the drug species, comprising formulating the acid in the form of an acid salt thereof.

125. A pharmaceutical product comprising a sealed container containing in the form of a finely divided solid, ready for reconstitution to form a liquid parenteral formulation, a therapeutically effective amount of a boronate salt which consists essentially of a single pharmaceutically acceptable base addition salt of a boronic acid formula (II):

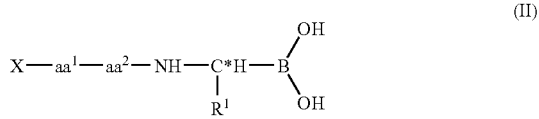

(II)

where:
  X is H (to form NH$_2$) or an amino-protecting group;
  aa$^1$ is an amino acid of R-configuration having a hydrocarbyl side chain containing no more than 20 carbon atoms and comprising at least one cyclic group having up to 13 carbon atoms;
  aa$^2$ is an imino acid of S-configuration having from 4 to 6 ring members;
  C* is a chiral centre of R-configuration; and
  R$^1$ is a group of the formula —CH$_2$)$_s$-Z, where s is 2, 3 or 4 and Z is —OH, —OMe, —OEt or halogen (F, Cl, Br or I).

126. The product of paragraph 125 wherein:
  X is R$^6$—(CH$_2$)$_p$—C(O)—, R$^6$—(CH$_2$)$_p$—S(0)$_2$—, R$^6$—(CH$_2$)$_p$—NH—C(O)— or R$^6$—(CH$_2$)$_p$—O—C(O)— wherein p is 0, 1, 2, 3, 4, 5 or 6 and R$^6$ is H or a 5 to 13-membered cyclic group optionally substituted by 1, 2 or 3 substituents selected from halogen, amino, nitro, hydroxy, a C$_5$-C$_6$ cyclic group, C$_1$-C$_4$ alkyl and C$_1$-C$_4$ alkyl and C$_1$-C$_4$ alkyl containing, and/or linked to the cyclic group through, an in-chain O, the aforesaid alkyl groups optionally being substituted by a substituent selected from halogen, amino, nitro, hydroxy and a C$_5$-C$_6$ cyclic group;
  aa$^1$ is selected from (R)-Phe, (R)-Dpa, (R)-Cha and (R)-Dcha;
  aa$^2$ is Pro; and
  R$^1$ is 2-ethoxyethyl or 3-methoxypropyl.

127. A pharmaceutical formulation adapted for parenteral administration, whether directly or after combining with a liquid, and comprising
  a) a first species selected from (a) boronic acids of formula (I), (b) boronate anions thereof, and (c) any equilibrium form of the aforegoing (e.g. an anhydride):

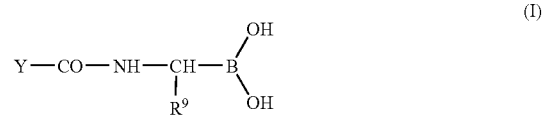

(I)

wherein
  Y comprises a hydrophobic moiety which, together with the aminoboronic acid residue —NHCH(R$^9$)—B (OH)$_2$, has affinity for the substrate binding site of thrombin; and
  R$^9$ is a straight chain alkyl group interrupted by one or more ether linkages and in which the total number of oxygen and carbon atoms is 3, 4, 5 or 6 or R$^9$ is —(CH$_2$)$_m$—W where m is from 2, 3, 4 or 5 and W is —OH or halogen (F, Cl, Br or I); and
  (b) a second species selected from the group consisting of pharmaceutically acceptable metal ions, said metal ions having a valency of n, lysine, arginine and aminosugars, wherein the formulation has an observed stoichiometry of first to second species essentially consistent with a notional stoichiometry of 1:1 except where the second species is a metal ion having a valency of greater than 1, in which case the observed stoichiometry is essentially consistent with a notional stoichiometry of n:1.

128. The formulation of paragraph 127 which has the characteristic that, after the formulation if not in an aqueous carrier is placed in one, it has a Ki for thrombin of about 20 nM or less.

129. The formulation of paragraph 127 or 128 in which R$^9$ is 3-methoxypropyl and the second species is sodium ions, lithium ions or lysine.

130. The formulation of any of paragraphs 127 to 129 which is in the form of fine particles for combining with a liquid to form a liquid formulation.

131. A diethanolamine ester of a boronic add of formula (VIII)

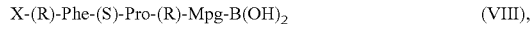

X-(R)-Phe-(S)-Pro-(R)-Mpg-B(OH)$_2$     (VIII), where X is H or an amino protecting group.

132. A product comprising, in the form of a finely divided solid, a salt consisting essentially of a monosodium or monolithium salt of an acid of the formula Cbz-(R)-Phe-(S)-Pro-(R)-Mpg-B(OH)$_2$, the salt containing no more than small amounts of other epimers of said acid, the salt optionally being in admixture with one or more anti-oxidants, preservatives or other additives.

133. The product of paragraph 132 in which the salt is in unit dosage form.

134. The product of paragraph 132 wherein the unit dosage form is small volume parenteral form for injection as an aqueous solution after reconstitution or is large volume parenteral form for infusion as an aqueous solution after reconstitution.

135. The product of any of paragraphs 132 to 134 which further includes an isotonicity agent.

136. The product of paragraph 132 which further includes water, optionally having dissolved therein one or more isotonicity agents and/or other additives, the water being in an amount suitable for dissolving said salt to form a liquid unit dosage form.

137. A product comprising, in the form of an isotonic aqueous solution, a salt consisting essentially of a monosodium or monolithium salt of an acid of the formula Cbz-(R)-Phe-(S)-Pro-(R)-Mpg-B(OH)$_2$, the salt containing no more than small amounts of other epimers of said acid, the product optionally further containing one or more anti-oxidants, preservatives or other additives.

138. The product of paragraph 137 which is in unit dosage form for administration by injection or infusion.

139. A method of presenting an acid of the formula Cbz-(R)-Phe-(S)-Pro-(R)-Mpg-B(OH)$_2$ in stabilised form for pharmaceutical use, comprising providing the acid in the form of a monosodium, monolithium or monolysine salt thereof and for administration after reconstitution as an aqueous parenteral solution.

The invention claimed is:

1. A parenteral pharmaceutical formulation comprising a pharmaceutically acceptable base addition salt of a boronic acid of formula (VIII):

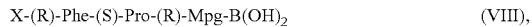

X-(R)-Phe-(S)-Pro-(R)-Mpg-B(OH)$_2$     (VIII), wherein X is R$^6$—(CH$_2$)$_p$—C(O)—, R$^6$—(CH$_2$)$_p$—S(O)$_2$—, R$^6$—(CH$_2$)$_p$—NH—C(O)— or R$^6$—(CH$_2$)$_p$—O—C(O)—, wherein p is 0, 1, 2, 3, 4, 5 or 6 and R$^6$ is H or a 5 to 13-membered cyclic group which is unsubstituted or substituted by 1, 2 or 3 substituents selected from halogen; amino; nitro; hydroxy; a C$_5$-C$_6$ cyclic group; C$_1$-C$_4$ alkyl and C$_1$-C$_4$ alkyl containing, or linked to the cyclic group through, an in-chain O atom, the aforesaid alkyl groups optionally being substituted by a substituent selected from halogen, amino, nitro, hydroxy and a C$_5$-C$_6$ cyclic group, wherein the salt in the parenteral pharmaceutical formulation is a salt of the boronic acid with an alkali metal, an aminosugar, a guanidine or an amine of formula (XI):

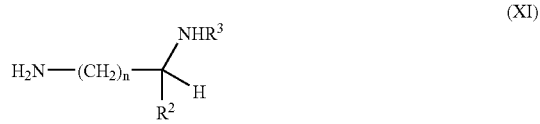

where n is from 1 to 6, R$^2$ is H, carboxylate or derivatised carboxylate, R$^3$ is H, C$_1$-C$_4$ alkyl or a residue of a natural or unnatural amino acid.

2. The parenteral pharmaceutical formulation of claim 1, wherein X is R$^6$—(CH$_2$)$_p$—O—C(O)— and p is 0 or 1.

3. The parenteral pharmaceutical formulation of claim 1, wherein R$^6$ is a 6-membered cyclic group that is unsubstituted and p is 1.

4. The parenteral pharmaceutical formulation of claim 1, wherein the salt is an alkali metal salt.

5. The parenteral pharmaceutical formulation of claim 4, wherein the alkali metal salt is a sodium salt.

6. The parenteral pharmaceutical formulation of claim 1, wherein the formulation comprises a salt of the boronic acid with an aminosugar.

7. The parenteral pharmaceutical formulation of claim 1, wherein the formulation comprises a salt of the boronic acid with a guanidine.

8. The parenteral pharmaceutical formulation of claim 1, wherein the formulation comprises a salt of the boronic acid with an amine of formula (XI):

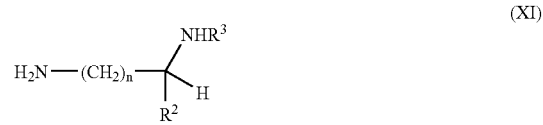

where n is from 1 to 6, R$^2$ is H, carboxylate or derivatised carboxylate, R$^3$ is H, C$_1$-C$_4$ alkyl or a residue of a natural or unnatural amino acid.

9. The parenteral pharmaceutical formulation of claim 1, wherein the formulation is an aqueous solution comprising the salt.

10. The parenteral pharmaceutical formulation of claim 9, wherein the aqueous solution further comprises a tonicity agent.

11. The parenteral pharmaceutical formulation of claim 1, which comprises the boronic acid in the form of an anhydride.

12. The parenteral pharmaceutical formulation of claim 1, wherein the boronic acid is of the formula Cbz-(R)-Phe-(S)-Pro-(R)-boroMpg-OH, boroMpg-OH being a residue of an aminoboronic acid of the formula H$_2$N—CH((CH$_2$)$_3$OMe)B(OH)$_2$, and wherein the formulation comprises anhydride species of the acid.

13. The parenteral pharmaceutical formulation of claim 1 wherein the boronic acid is of the formula Cbz-(R)-Phe-(S)-Pro-(R)-Mpg-B(OH)$_2$.

14. The parenteral pharmaceutical formulation of claim 1, wherein the salt is an alkali metal salt of Cbz-(R)-Phe-(S)-Pro-(R)-Mpg-B(OH)$_2$.

15. The parenteral pharmaceutical formulation of claim 14, wherein the salt is a sodium salt of Cbz-(R)-Phe-(S)-Pro-(R)-Mpg-B(OH)$_2$.

16. The parenteral pharmaceutical formulation of claim 1, further comprising at least one cardiovascular treatment agent selected from the group consisting of a lipid-lowering drug, an anti-oxidant, a GP IIb/IIIa antagonist, an aldosterone inhibitor, an adenosine A2 antagonist, an adenosine A3 agonist, a beta-blocker, acetylsalicylic acid, a loop diuretic, an ACE inhibitor, an antithrombotic agent with a different mechanism of action from the salt of formula (VIII), an antiplatelet agent, a thromboxane receptor inhibitor, a synthetase inhibitor, a fibrinogen receptor antagonist, a prostacyclin mimetic, a phosphodiesterase inhibitor, an ADP-receptor (P$_2$T) antagonist, a thrombolytic, and a COX-2 inhibitor, and combinations thereof.

17. The parenteral pharmaceutical formulation of claim 1, wherein the salt is a sodium salt of a boronic acid of the formula Cbz-(R)-Phe-(S)-Pro-(R)-Mpg-B(OH)$_2$, and wherein the salt is in an aqueous solution.

18. The parenteral pharmaceutical formulation of claim 15 wherein the salt is the monosodium salt and the formulation either is an aqueous solution or is in solid form for making up into an aqueous solution for administration.

19. A pharmaceutical product comprising a sealed container containing in the form of a finely divided solid, ready for reconstitution to form a liquid parenteral formulation, a pharmaceutically acceptable base addition salt of a boronic acid of formula (VIII), wherein the boronic acid is pharmaceutically active:

X-(R)-Phe-(S)-Pro-(R)-Mpg-B(OH)$_2$     (VIII), wherein X is $R^6$—$(CH_2)_p$—C(O)—, $R^6$—$(CH_2)_p$—S(O)$_2$—, $R^6$—$(CH_2)_p$—NH—C(O)— or $R^6$—$(CH_2)_p$—O—C(O)—, wherein p is 0, 1, 2, 3, 4, 5 or 6 and $R^6$ is H or a 5 to 13-membered cyclic group which is unsubstituted or substituted by 1, 2 or 3 substituents selected from halogen; amino; nitro; hydroxy; a $C_5$-$C_6$ cyclic group; $C_1$-$C_4$ alkyl and $C_1$-$C_4$ alkyl containing, or linked to the cyclic group through, an in-chain O atom, the aforesaid alkyl groups optionally being substituted by a substituent selected from halogen, amino, nitro, hydroxy and a $C_5$-$C_6$ cyclic group, wherein the salt in the pharmaceutical product is a salt of the boronic acid with an alkali metal, an aminosugar, a guanidine or an amine of formula (XI):

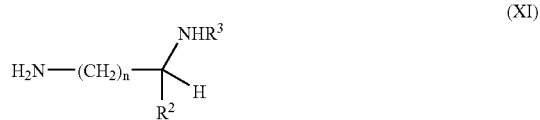

where n is from 1 to 6, $R^2$ is H, carboxylate or derivatised carboxylate, $R^3$ is H, $C_1$-$C_4$ alkyl or a residue of a natural or unnatural amino acid.

20. The pharmaceutical product of claim 19, wherein X is $R^6$—$(CH_2)_p$—O—C(O)— and p is 0 or 1.

21. The pharmaceutical product of claim 19, wherein $R^6$ is a 6-membered cyclic group that is unsubstituted and p is 1.

22. The pharmaceutical product of claim 21, wherein the salt is an alkali metal salt.

23. The pharmaceutical product of claim 22, wherein the alkali metal salt is a sodium salt.

24. The pharmaceutical product of claim 19, wherein the boronic acid is of the formula Cbz-(R)-Phe-(S)-Pro-(R)-Mpg-B(OH)$_2$.

25. The pharmaceutical product of claim 19, wherein the salt is an alkali metal salt of Cbz-(R)-Phe-(S)-Pro-(R)-Mpg-B(OH)$_2$.

26. The pharmaceutical product of claim 25, wherein the salt is a sodium salt of Cbz-(R)-Phe-(S)-Pro-(R)-Mpg-B(OH)$_2$.

27. The pharmaceutical product of claim 26 wherein the salt is a monosodium salt.

28. A method of treating thrombosis, comprising parenterally administering to a mammal suffering from, or at risk of suffering from, thrombosis a therapeutically effective amount of a composition comprising a pharmaceutically acceptable base addition salt of a boronic acid of formula (VIII):

X-(R)-Phe-(S)-Pro-(R)-Mpg-B(OH)$_2$     (VIII), wherein X is $R^6$—$(CH_2)_p$—C(O)—, $R^6$—$(CH_2)_p$—S(O)$_2$—, $R^6$—$(CH_2)_p$—NH—C(O)— or $R^6$—$(CH_2)_p$—O—C(O)—, wherein p is 0, 1, 2, 3, 4, 5 or 6 and $R^6$ is H or a 5 to 13-membered cyclic group which is unsubstituted or substituted by 1, 2 or 3 substituents selected from halogen; amino; nitro; hydroxy; a $C_5$-$C_6$ cyclic group; $C_1$-$C_4$ alkyl and $C_1$-$C_4$ alkyl containing, or linked to the cyclic group through, an in-chain O atom, the aforesaid alkyl groups optionally being substituted by a substituent selected from halogen, amino, nitro, hydroxy and a $C_5$-$C_6$ cyclic group, wherein the salt is a salt of the boronic acid with an alkali metal, an aminosugar, a guanidine or an amine of formula (XI):

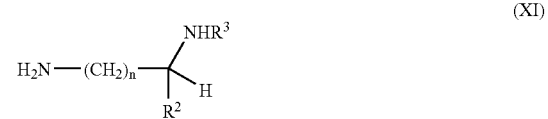

where n is from 1 to 6, $R^2$ is H, carboxylate or derivatised carboxylate, $R^3$ is H, $C_1$-$C_4$ alkyl or a residue of a natural or unnatural amino acid.

29. The method of claim 28, wherein X is $R^6$—$(CH_2)_p$—O—C(O)— and p is 0 or 1.

30. The method of claim 28, wherein $R^6$ is a 6-membered cyclic group that is unsubstituted and p is 1.

31. The method of claim 28, wherein the salt is an alkali metal salt.

32. The method of claim 28, wherein the alkali metal salt is a sodium salt.

33. The method of claim 28, wherein the boronic acid is of the formula Cbz-(R)-Phe-(S)-Pro-(R)- Mpg-B(OH)$_2$.

34. The method of claim 28, wherein the salt is an alkali metal salt of Cbz-(R)-Phe-(S)-Pro-(R)-Mpg-B(OH)$_2$.

35. The method of claim 34, wherein a salt is the sodium salt of Cbz-(R)-Phe-(S)-Pro-(R)-Mpg-B(OH)$_2$.

36. The method of claim 28, wherein the formulation is administered intravenously.

37. The method of claim 28, further comprising co-administering at least one additional cardiovascular treatment agent selected from the group consisting of a lipid-lowering drug, an anti-oxidant, a GP IIb/IIIa antagonist, an aldosterone inhibitor, an adenosine A2 antagonist, an adenosine A3 agonist, a beta-blocker, acetylsalicylic acid, a loop diuretic, an ACE inhibitor, an antithrombotic agent with a different mechanism of action from the salt of formula (VIII), an antiplatelet agent, a thromboxane receptor inhibitor, a synthetase inhibitor, a fibrinogen receptor antagonist, a prostacyclin mimetic, a phosphodiesterase inhibitor, an ADP-receptor (P$_2$T) antagonist, a thrombolytic, and a COX-2 inhibitor, and combinations thereof.

38. The method of claim 35 wherein the composition comprises an aqueous solution of the salt.

39. A pharmaceutical formulation adapted for parenteral administration, whether directly or after combining with a liquid, and the pharmaceutical formulation comprising:

a) a first component selected from the group consisting of (i) a boronic acid of formula (VIII) below, (ii) boronate ions of the boronic acid of formula (VIII) below, and (iii) an equilibrium form of the boronic acid of formula (VIII) below and boronate ions of the boronic acid of formula (VIII) below, and (iv) combinations thereof:

X-(R)-Phe-(S)-Pro-(R)-Mpg-B(OH)$_2$     (VIII), wherein X is $R^6$—$(CH_2)_p$—C(O)—, $R^6$—$(CH_2)_p$—S(O)$_2$—, $R^6$—$(CH_2)_p$—NH—C(O)— or $R^6$—$(CH_2)_p$—O—C(O)—, wherein p is 0, 1, 2, 3, 4, 5 or 6 and $R^6$ is H or a 5 to 13-membered cyclic group which is unsubstituted or substituted by 1, 2 or 3 substituents selected from halogen; amino; nitro; hydroxy; a $C_5$-$C_6$ cyclic group; $C_1$-$C_4$ alkyl and $C_1$-$C_4$ alkyl containing, or linked to the cyclic group through, an in-chain O atom, the aforesaid alkyl groups optionally being substituted by a substituent selected from halogen, amino, nitro, hydroxy and a $C_5$-$C_6$ cyclic group; and (b) a second, pharmaceutically acceptable, component selected from the group consisting of alkali metal ions, aminosugars, guanidines and amines of formula (XI):

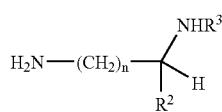

where n is from 1 to 6, $R^2$ is H, carboxylate or derivatised carboxylate, $R^3$ is H, $C_1$-$C_4$ alkyl or a residue of a natural or unnatural amino acid.

40. The pharmaceutical formulation of claim 39 wherein X is $R^6$—$(CH_2)_p$—$C(O)$—, $R_6$ is a 6-membered cyclic group that is unsubstituted and p is 1.

41. The pharmaceutical formulation of claim 40 wherein the second component is N-methyl-D-glucamine.

42. The pharmaceutical formulation of claim 40 wherein the second component is L-lysine.

43. The pharmaceutical formulation of claim 40 wherein the second component is L-arginine.

44. The pharmaceutical formulation of claim 40 wherein the second component is lithium.

45. The pharmaceutical formulation of claim 40 wherein the second component is potassium.

46. The pharmaceutical formulation of claim 40 wherein the second component is sodium.

47. The pharmaceutical formulation of claim 39 wherein the boronic acid is of the formula Cbz-(R)-Phe-(S)-Pro-(R)-Mpg-B(OH)2.

48. The pharmaceutical formulation of claim 46 wherein the boronic acid is of the formula Cbz-(R)-Phe-(S)-Pro-(R)-Mpg-B(OH)$_2$.

* * * * *